(12) United States Patent
Godbout et al.

(10) Patent No.: US 12,358,910 B2
(45) Date of Patent: Jul. 15, 2025

(54) HETEROAROMATIC COMPOUNDS AS VANIN INHIBITORS

(71) Applicant: Boehringer Ingelheim International GmbH, Ingelheim am Rhein (DE)

(72) Inventors: Cedrickx Godbout, Attenweiler (DE); Martin Thomas Fleck, Munich (DE); Hannes Fiepko Koolman, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1010 days.

(21) Appl. No.: 17/299,164

(22) PCT Filed: Dec. 2, 2019

(86) PCT No.: PCT/EP2019/083262
§ 371 (c)(1),
(2) Date: Jun. 2, 2021

(87) PCT Pub. No.: WO2020/114949
PCT Pub. Date: Jun. 11, 2020

(65) Prior Publication Data
US 2022/0041592 A1    Feb. 10, 2022

(30) Foreign Application Priority Data

Dec. 3, 2018   (EP) .................................. 18209727

(51) Int. Cl.
| | |
|---|---|
| *C07D 471/04* | (2006.01) |
| *A61K 31/4365* | (2006.01) |
| *A61K 31/437* | (2006.01) |
| *A61K 31/4439* | (2006.01) |
| *A61K 31/444* | (2006.01) |
| *A61K 31/4709* | (2006.01) |
| *A61K 31/519* | (2006.01) |
| *A61K 45/06* | (2006.01) |
| *C07D 401/12* | (2006.01) |
| *C07D 401/14* | (2006.01) |
| *C07D 403/14* | (2006.01) |
| *C07D 409/14* | (2006.01) |
| *C07D 413/14* | (2006.01) |
| *C07D 495/04* | (2006.01) |

(52) U.S. Cl.
CPC ........ *C07D 471/04* (2013.01); *A61K 31/4365* (2013.01); *A61K 31/437* (2013.01); *A61K 31/4439* (2013.01); *A61K 31/444* (2013.01); *A61K 31/4709* (2013.01); *A61K 31/519* (2013.01); *A61K 45/06* (2013.01); *C07D 401/12* (2013.01); *C07D 401/14* (2013.01); *C07D 403/14* (2013.01); *C07D 409/14* (2013.01); *C07D 413/14* (2013.01); *C07D 495/04* (2013.01)

(58) Field of Classification Search
CPC .. C07D 471/04; C07D 495/04; C07D 401/14; C07D 403/14; C07D 409/14
See application file for complete search history.

(56) References Cited

U.S. PATENT DOCUMENTS

| | | |
|---|---|---|
| 9,585,891 B2 | 3/2017 | Muzerelle et al. |
| 9,975,882 B2 | 5/2018 | Bosanac et al. |
| 10,308,615 B2 | 6/2019 | Casimiro-Garcia et al. |
| 10,364,255 B2 | 7/2019 | Bosanac et al. |
| 11,078,182 B2 | 8/2021 | Fleck et al. |
| 2003/0195192 A1 | 10/2003 | Haviv et al. |
| 2014/0357612 A1 | 12/2014 | Zhang et al. |
| 2015/0250792 A1 | 9/2015 | Muzerelle et al. |
| 2018/0148420 A1 | 5/2018 | Casimiro-Garcia et al. |
| 2018/0354968 A1 | 12/2018 | Bosanac et al. |
| 2019/0263828 A1 | 8/2019 | Bosanac et al. |
| 2020/0069663 A1 | 3/2020 | Godbout et al. |

(Continued)

FOREIGN PATENT DOCUMENTS

| | | |
|---|---|---|
| WO | 2005035524 A1 | 4/2005 |
| WO | 2014048547 A1 | 4/2014 |
| WO | 2016193844 A1 | 12/2016 |

(Continued)

OTHER PUBLICATIONS

Barluenga, Jose et al. "Arylation of a-Chiral Ketones by Palladium-Catalyzed Cross-Coupling Reactions of Tosylhydrazones with Aryl Halides" (2010) Angew. Chem. Int. Ed., 49, 6856-6859.

(Continued)

*Primary Examiner* — Jeffrey H Murray
*Assistant Examiner* — Madeline E Braun
(74) *Attorney, Agent, or Firm* — David L. Kershner

(57) ABSTRACT

The present invention encompasses compounds of the formula I

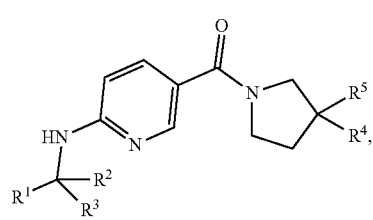

which are suitable for the treatment of diseases related to Vanin, and processes for making these compounds, pharmaceutical preparations containing these compounds, and their methods of use.

14 Claims, No Drawings

(56) References Cited

U.S. PATENT DOCUMENTS

| | | |
|---|---|---|
| 2020/0172508 A1 | 6/2020 | Fleck et al. |
| 2023/0295112 A1 | 9/2023 | Fleck et al. |

FOREIGN PATENT DOCUMENTS

| | | | | |
|---|---|---|---|---|
| WO | WO-2018011681 A1 * | 1/2018 | ........... | A61K 31/506 |
| WO | 2018228934 A1 | 12/2018 | | |

OTHER PUBLICATIONS

Berge, Stephen M et al. "Journal of Pharmaceutical Salts" Jan. 1977, vol. 66, No. 1, 1-19.
Berruyer, C. et al. "Vanin-1 −/− Mice Exhibit a Glutathione-Mediated Tissue Resistance to Oxidative Stress" (2004) Molecular and Cellular Biology, vol. 24, No. 16, 7214-7224.
Berruyer, Carole et al. "Vanin-1 licenses inflammatory mediator production by gut epithelial cells and controls colitis by antagonizing peroxisome proliferator-activated receptor y activity" (2006) The Journal of Experimental Medicine, vol. 203, No. 13, 2817-2827.
CAS Registry No. 2128587-10-8, Sep. 19, 2017, 1 pg.
CAS Registry No. 2130646-08-9, Sep. 25, 2017, 1 pg.
CAS Registry No. 2175416-99-4, Feb. 18, 2018, 1 pg.
Chai, Chi-Young et al. "VNN1 overexpression is associated with poor response to preoperative chemoradiotherapy and adverse prognosis in patients with rectal cancers" (2016) Am J Transl Res, 8(10): 4455-4463.
Gensollen, Thomas et al. "Functional Polymorphisms in the Regulatory Regions of the VNN1 Gene are associated with Susceptibility to Inflammatory Bowel Diseases" (2013) Inflammatory Bowel Diseases, vol. 19, No. 11, 2315-2325.
He, Ling et al. "Protective Effect and Mechanism of Vanin on Iselt NIT Cells" (2011) China Journal Prevention Contr Chronic Disease, vol. 19, No. 3, 275-277 (English abstract).
International Search Report PCT/EP2018/065140 mailed Jul. 31, 2018.
International Search Report PCT/EP2019/072699 mailed on Nov. 12, 2019.
International Search Report PCT/EP2019/083252 mailed Feb. 17, 2020.
International Search Report PCT/EP2019/083262 mailed Mar. 5, 2020.
Jansen, Patrick A.M. et al. "Expression of the Vanin Gene Family in Normal and Inflamed Human Skin: Induction by Proinflammatory Cytokines" (2009) The Journal of Investigative Dermatology, vol. 129, No. 9, 2167-2174.
Kang, Muxing et al. "VNN1, a potential biomarker for pancreatic cancer-associated new-onset diabetes, aggravates paraneoplastic islet dysfunction by increasing oxidative stress" (2016) Cancer Letters, 373, 241-250.
Kavian, Niloufar et al. "Imbalance of the Vanin-1 Pathway in Systemic Sclerosis" (2016) The Journal of Immunology, vol. 197, 3326-3335.
Khor, Bernard et al. "Genetics and pathogenesis of inflammatory bowel disease" (2011) Nature, vol. 474, 307-317.
Lipinski, Boguslaw "Pathophysiology of oxidative stress in diabetes mellitus" (2001) Journal of Diabetes and its Complications, vol. 15, 203-210.
Martin, Florent et al. "Vanin genes are clustered (human 6q22-24 and mouse 10A2B1) and encode isoforms of pantetheinase ectoenzymes" (2001) Immunogenetics, 53: 296-306.
Martin, Florent et al. "Vanin-1 −/− mice show decreased NSAID- and Schistosoma-induced intestinal inflammation assoicated with higher glutathione stores" (2004) The Journal of Clinical Investigation, vol. 113, No. 4, 591-597.
Naquet, Philippe et al. "Role of the Vnn1 pantetheinase in tissue tolerance to stress" (2014) Biochemical Society Transactions, vol. 42, part 4, 1094-1100.
Pouyet, Laurent et al. "Epithelial vanin-1 controls inflammation-driven carcinogenesis in the colitis-associated colon cancer model" (2010) Inflammatory Bowel Diseases, vol. 16, No. 1, 96-104.
Sosa, Venus et al. "Oxidative stress and cancer: An overview" (2013) Ageing Research Reviews, vol. 12, 376-390.
Zhang, Bing et al. "The role of vanin-1 and oxidative stress-related pathways in distinguishing acute and chronic pediatric ITP" (2011) Blood, vol. 117, No. 17, 4569-4579.

* cited by examiner

HETEROAROMATIC COMPOUNDS AS VANIN INHIBITORS

BACKGROUND OF THE INVENTION

1. Technical Field

The present invention relates to novel compounds which inhibit Vanin, pharmaceutical compositions containing the same and their use as medicaments.

2. Background Information

Isoforms 1 and 2 of Vanin enzymes are single-domain extracellular pantetheinases that catalyze the cleavage of pantethine and pantetheine into pantothenic acid and cystamine and cysteamine, respectively (Martin, Immunogenetics, (2001 May-June) Vol. 53, No. 4, pp. 296-306). Generation of cysteamine has been linked to increased oxidative in tissue stress resulting from decreased glutathione levels, a condition characteristic of many pathological conditions, including IBD (Xavier, Nature. 2011 Jun. 15; 474 (7351): 307-17), cancer (Sosa, Ageing research reviews, (2013 January) Vol. 12, No. 1, pp. 376-90) and diabetes (Lipinski, Journal of diabetes and its complications, (2001 July-August) Vol. 15, No. 4, pp. 203-10).

Increased Vanin-1 activity in the gut epithelium has been implicated in promoting tissue damage and inflammation by reducing resistance to oxidative stress in murine models (Naquet, Biochem Soc Trans. 2014 August; 42(4):1094-100); (Berruyer, Molecular and cellular biology, (2004 August) Vol. 24, No. 16, pp. 7214-24); (Berruyer, The Journal of experimental medicine, (2006 Dec. 25) Vol. 203, No. 13, pp. 2817-27); (Pouyet, Inflammatory bowel diseases, (2010 January) Vol. 16, No. 1, pp. 96-104). Homozygous VNN1 knock-out (KO) mice lack appreciable levels of cysteamine in blood and tissues and show glutathione-mediated tissue resistance to oxidative stress (Berruyer, The Journal of experimental medicine, (2006 Dec. 25) Vol. 203, No. 13, pp. 2817-27). In addition, these mice are protected from intestinal injury in TNBS, DSS and *Schistosoma*-induced colitis models (Berruyer, The Journal of experimental medicine, (2006 Dec. 25) Vol. 203, No. 13, pp. 2817-27; Pouyet, Inflammatory bowel diseases, (2010 January) Vol. 16, No. 1, pp. 96-104; Martin, The Journal of clinical investigation, (2004 February) Vol. 113, No. 4, pp. 591-7). Given rodents lack Vanin-2, their only source of cysteamine is from Vanin-1, therefore the protective phenotype of the VNN1 KO mouse is attributed to the lack of cysteamine.

In humans, Vanin-1 was observed to be upregulated in intestinal epithelium in tissue biopsies from UC and CD patients and a functional polymorphism in the regulatory region of the VNN1 gene which led to increased VNN1 expression was associated with increased IBD susceptibility (P=0.0003 heterozygous vs. wild-type) (Gensollen, Inflammatory bowel diseases, (2013 October) Vol. 19, No. 11, pp. 2315-25).

In addition, upregulation of Vanin-1 activity in the skin and blood has been linked to development and severity of fibrosis in Systemic Sclerosis patients (Kavian, Journal of immunology (Baltimore, Md.: 1950), (20161015) Vol. 197, No. 8, pp. 3326-3335), and elevated levels of Vanin-1 have been observed in chronic Juvenile Idiopathic Thrombocytopenia (Zhang, Blood, (2011 Apr. 28) Vol. 117, No. 17, pp. 4569-79), Psoriasis and Atopic Dermatitis (Jansen, The Journal of investigative dermatology, (2009 September) Vol. 129, No. 9, pp. 2167-74).

Elevated Vanin-1 expression and activity are also present and serve as biomarkers for pancreatic cancer associated new-onset diabetes (Kang, Cancer Letters (New York, NY, United States) (2016), 373(2), 241-250) and are also correlated with poor prognosis and response to treatment in colorectal cancer (Chai, American journal of translational research, (2016) Vol. 8, No. 10, pp. 4455-4463).

WO2018011681 and WO2016193844 disclose Vanin inhibitors for the treatment of a series of diseases e.g. Crohn's disease and ulcerative colitis.

The problem to be solved by the present invention is to provide novel compounds which act as inhibitors of Vanin enzymes, preferably as inhibitors of the Vanin-1 enzyme.

It has been surprisingly found that the compounds of the present invention have potent Vanin-1 inhibitors activity, preferably exhibiting an inhibition of VNN-1 $IC_{50}$ [nM] <100, more preferred $IC_{50}$ [nM]<10, particularly preferred $IC_{50}$ [nM]<1.

Drugs with long residence times in the body are preferred because they remain effective for a longer period of time and therefore can be used in lower doses. Surprisingly the compounds of the present invention indicate favorable mean residence times (MRT).

Moreover the compounds of the present invention exhibit further capacities, which are favorable for their pharmacokinetic and pharmacological profile, e.g. good solubility and good metabolic stability.

DETAILED DESCRIPTION OF THE INVENTION

It has surprisingly been found that the problem mentioned above is solved by compounds of formula I of the present invention.

The present invention therefore relates to a compound of formula I

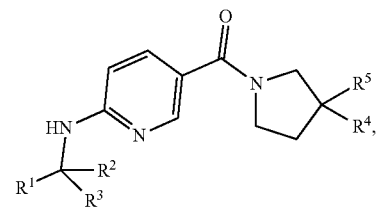

wherein $R^1$ denotes naphthalenyl substituted with $R^{1.1}$ and $R^{1.2}$ or
  8-10 membered heteroaryl containing 1 to 3 heteroatoms selected from the group consisting of S, N and O substituted with $R^{1.1}$ and $R^{1.2}$,
$R^{1.1}$ is selected from the group consisting of H, $C_{1-4}$-alkyl, $C_{1-2}$-alkyl-O—, $CF_3$, $C_{3-5}$-cycloalkyl, $H_2N$—, Br, Cl and F;
$R^{1.2}$ is selected from the group consisting of H, $C_{1-4}$-alkyl, $CF_3$, $H_2N$—, Br, Cl and F;
wherein in the definition of $R^{1.1}$ and $R^{1.2}$ mentioned alkyl is optionally substituted by 1-3 F-atoms
$R^2$ and $R^3$ are independently from each other selected from the group consisting of H and methyl, $R^4$ denotes $R^{4.1}R^{4.2}N$— or NC;
or
$R^4$ denotes a group of formula $R^{4.a}$

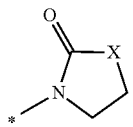

$R^{4.a}$ wherein
X denotes $CH_2$ or O;
$R^{4.1}$ is selected from the group consisting of $C_{1-4}$-alkyl-CO—, 6-membered heteroaryl containing 1-2 N-atoms, $C_{3-5}$-cycloalkyl-CO— substituted by $R^{4.1.1}$ and $R^{4.1.2}$, Phenyl-CO— optionally substituted by 1-2 halogen atoms, $C_{1-4}$-alkyl- or $CH_3$—O— and 5 to 6 membered heteroaryl-CO— optionally substituted by $C_{1-4}$-alkyl- or $CH_3$—O—.
wherein
$R^{4.1.1}$, $R^{4.1.2}$ independently from each other are selected from the group consisting of H, —$CH_3$, F, and —CN;
$R^{4.2}$ denotes H or $C_{1-3}$-alkyl,
$R^5$ denotes H or methyl;
or a pharmaceutically acceptable salt thereof.

PREFERRED EMBODIMENTS

In another embodiment of the present invention $R^1$ denotes naphthalenyl,
8-10 membered heteroaryl containing 1 to 3 heteroatoms selected from the group consisting of N and S substituted with $R^{1.1}$ and $R^{1.2}$,
or
8-10 membered heteroaryl containing 1 to 3 heteroatoms selected from the group consisting of N and O substituted with $R^{1.1}$ and $R^{1.2}$,
or a pharmaceutically acceptable salt thereof.
In another embodiment of the present invention $R^1$ denotes naphthalenyl.
In another embodiment of the present invention $R^1$ denotes
8-10 membered heteroaryl containing 1 to 3 heteroatoms selected from the group consisting of N and S substituted with $R^{1.1}$ and $R^{1.2}$.
In another embodiment of the present invention $R^1$ denotes
8-10 membered heteroaryl containing 1 to 3 heteroatoms selected from the group consisting of N and O substituted with $R^{1.1}$ and $R^{1.2}$,
In another embodiment of the present invention $R^1$ is substituted with $R^{1.1}$ and $R^{1.2}$ and is selected from the group consisting of Substituents $R^{1.a}$ to $R^{1.p}$.

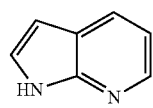

$R^{1.a}$

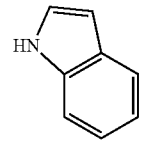

R1.b

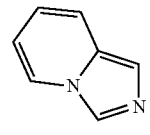

R1.c

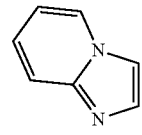

R1.d

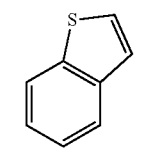

R1.e

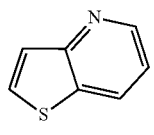

R1.f

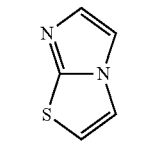

R1.g

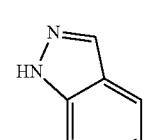

R1.h

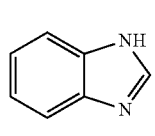

R1.i

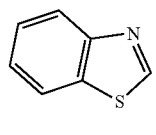

R1.j

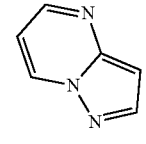

R1.k

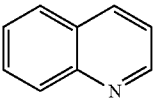

R1.m

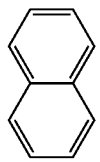

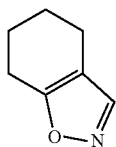

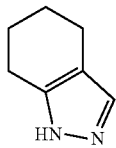

In another embodiment of the present invention $R^1$ is substituted with $R^{1.1}$ and $R^{1.2}$ and selected from the group consisting of Substituents $R^{1.a}$, $R^{1.d}$, $R^{1.e}$, $R^{1.g}$, $R^{1.i}$, $R^{1.h}$, $R^{1.m}$ and $R^{1.p}$.

In another embodiment of the present invention $R^{1.1}$ is selected from the group consisting of H, methyl, $H_2N-$, Br, Cl and F.

In another embodiment of the present invention $R^{1.2}$ is selected from the group consisting of H, methyl and Cl.

In another embodiment of the present invention $R^{1.1}$ and $R^{1.2}$ are H.

In another embodiment of the present invention $R^{1.1}$ denotes H.

In another embodiment of the present invention $R^{1.2}$ denotes H.

In another embodiment of the present invention $R^2$ denotes H, and $R^3$ denotes methyl.

In another embodiment of the present invention $R^2$ and $R^3$ denote H.

In another embodiment of the present invention $R^4$ denotes $R^{4.1}R^{4.2}N$.

In another embodiment of the present invention $R^4$ denotes —CN.

In another embodiment of the present invention $R^4$ denotes a group of formula $R^{4.a}$

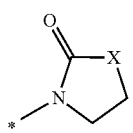

wherein
X denotes $CH_2$ or O.

In another embodiment of the present invention X denotes O.

In another embodiment of the present invention X denotes $CH_2$.

In another embodiment of the present invention
$R^{4.1}$ is selected from the group consisting of $C_{1-4}$-alkyl-CO—, $C_{3-4}$-cycloalkyl-CO— substituted with $R^{4.1.1}$ and $R^{4.1.2}$;

wherein
$R^{4.1.1}$, $R^{4.1.2}$ independently from each other are selected from the group consisting of H, $CH_3$, F and —CN; and $R^{4.2}$ denotes methyl or ethyl.

In another embodiment of the present invention
$R^{4.1}$ denotes $CH_3$—CO— or $C_{3-4}$-cycloalkyl-CO— substituted with $R^{4.1.1}$ and $R^{4.1.2}$, wherein
$R^{4.1.1}$, $R^{4.1.2}$ independently from each other are selected from the group consisting of H, —$CH_3$, F and —CN; and $R^{4.2}$ denotes methyl.

In another embodiment of the present invention $R^{4.1}$ denotes $CH_3$—CO—.

In another embodiment of the present invention $R^{4.1}$ denotes $C_{3-4}$-cycloalkyl-CO— substituted with $R^{4.1.1}$ and $R^{4.1.2}$.

In another embodiment of the present invention $R^{4.1.1}$ and $R^{4.1.2}$ denote H.

In another embodiment of the present invention $R^{4.1.1}$ and $R^{4.1.2}$ denote F.

In another embodiment of the present invention $R^{4.1.1}$ denotes $CH_3$, F or —CN and $R^{4.1.2}$ denotes H.

In another embodiment of the present invention $R^5$ denotes H.

In another embodiment of the present invention $R^5$ denotes methyl.

A preferred embodiment of the current invention is a compound of the formula I wherein
$R^1$ denotes naphthalenyl substituted with $R^{1.1}$ and $R^{1.2}$ or 8-10 membered heteroaryl containing 1 to 3 heteroatoms selected from the group consisting of S, N and O substituted with $R^{1.1}$ and $R^{1.2}$,
$R^{1.1}$ is selected from the group consisting of H, $C_{1-4}$-alkyl, $CF_3$, $H_2N-$, Br, Cl and F;
$R^{1.2}$ is selected from the group consisting of H, $C_{1-4}$-alkyl, $CF_3$, $H_2N-$, Br, Cl and F;
$R^2$ and $R^3$ are independently from each other selected from the group consisting of H and methyl,
$R^4$ denotes $R^{4.1}R^{4.2}N-$ or NC;
or
$R^4$ denotes a group of formula $R^{4.a}$

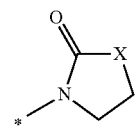

wherein
X denotes $CH_2$ or O;
$R^{4.1}$ is selected from the group consisting of $C_{1-4}$-alkyl-CO—, $C_{3-4}$-cycloalkyl-CO— substituted with $R^{4.1.1}$ and $R^{4.1.2}$;
wherein
$R^{4.1.1}$, $R^{4.1.2}$ independently from each other are selected from the group consisting of H, $CH_3$, F and —CN;
$R^{4.2}$ denotes methyl or ethyl;
$R^5$ denotes H or methyl;
or a pharmaceutically acceptable salt thereof.

A preferred embodiment of the current invention is a compound of the formula I

R[1] denotes naphthalenyl or
- 8-10 membered heteroaryl containing 1 to 3 heteroatoms selected from the group consisting of S, N and O substituted with R[1.1] and R[1.2], R[1.1] is selected from the group consisting of H, methyl, $H_2N-$, Br, Cl and F;

R[1.2] is selected from the group consisting of H, methyl and Cl;

R[2] and R[3] independently from each other denote H or methyl;

R[4] denotes R[4.1]R[4.2]N— or NC—;

or R[4] denotes a group of formula R[4.a]

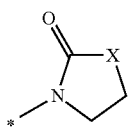

wherein
X denotes $CH_2$ or O;

R[4.1] is selected from the group consisting of $C_{1-4}$-alkyl-CO, $C_{3-4}$-cycloalkyl-CO— substituted with R[4.1.1] and R[4.1.2],
  wherein
  R[4.1.1], R[4.1.2] independently from each other are selected from the group consisting of H, —$CH_3$, F and —CN;

R[4.2] denotes methyl;

R[5] denotes H or methyl;

or a pharmaceutically acceptable salt thereof.

Any and each of the definitions of R[1], R[2], R[3], R[4], R[5], R[1.1], R[1.2], R[4.1], R[4.2], R[4.1.1], R[4.1.2], R[4.a] and X may be combined with each other.

A further preferred embodiment of the current invention are the above compounds of formula I, selected from the group consisting of examples 2.1, 3.1, 4.1, 5.2, 5.3, 5.4, 5.7, 5.13, 5.14, 5.22, 5.24, 5.38 and 5.40;

Ex. 2.1

Ex. 3.1

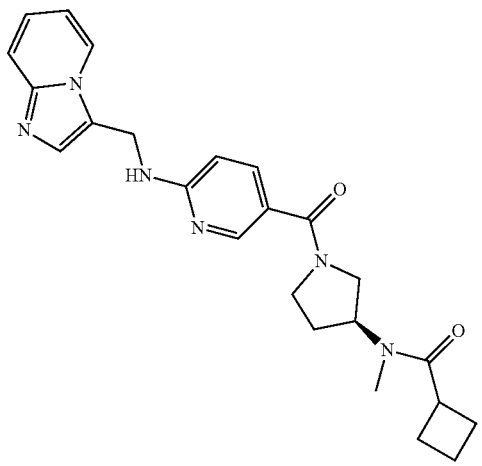

Ex. 4.1

Ex. 5.2

Ex. 5.4

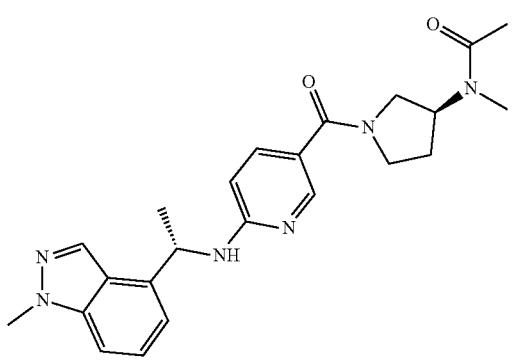

Ex. 5.7

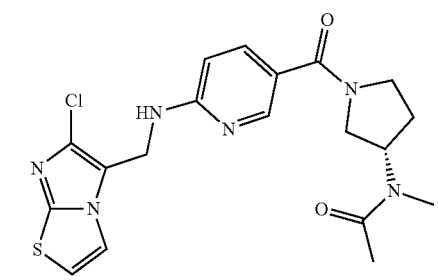

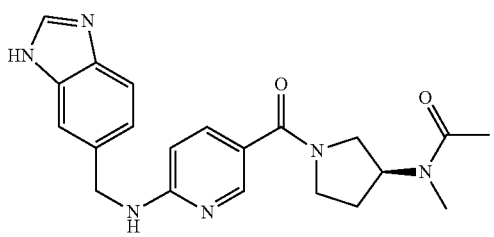

Ex. 5.13

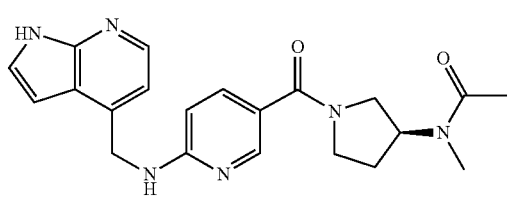

or a pharmaceutically acceptable salt thereof.

A further preferred embodiment of the current invention are the above compounds of formula I, selected from the group consisting of examples 2.1, 3.1, 4.1, 5.2, 5.3, 5.4, 5.7, 5.13, 5.14, 5.22, 5.24, 5.38 and 5.40.

A further preferred embodiment of the current invention is the compound of example 2.1.

A further preferred embodiment of the current invention is the compound of example 3.1

A further preferred embodiment of the current invention is the compound of example 4.1.

A further preferred embodiment of the current invention is the compound of example 5.2.

A further preferred embodiment of the current invention is the compound of example 5.3.

A further preferred embodiment of the current invention is the compound of example 5.4.

A further preferred embodiment of the current invention is the compound of example 5.7.

A further preferred embodiment of the current invention is the compound of example 5.13.

A further preferred embodiment of the current invention is the compound of example 5.14.

A further preferred embodiment of the current invention is the compound of example 5.22.

A further preferred embodiment of the current invention is the compound of example 5.24.

A further preferred embodiment of the current invention is the compound of example 5.38.

A further preferred embodiment of the current invention is the compound of example 5.40.

A further preferred embodiment of the current invention are pharmaceutically acceptable salts of the above compounds of formula I, selected from the group consisting of examples 2.1, 3.1, 4.1, 5.2, 5.3, 5.4, 5.7, 5.13, 5.14, 5.22, 5.24, 5.38 and 5.40.

A further preferred embodiment of the current invention are pharmaceutically acceptable salts of the compound of example 2.1.

A further preferred embodiment of the current invention are pharmaceutically acceptable salts of the compound of example 3.1.

A further preferred embodiment of the current invention are pharmaceutically acceptable salts of the compound of example 4.1.

A further preferred embodiment of the current invention are pharmaceutically acceptable salts of the compound of example 5.2.

A further preferred embodiment of the current invention are pharmaceutically acceptable salts of the compound of example 5.3.

A further preferred embodiment of the current invention are pharmaceutically acceptable salts of the compound of example 5.4.

A further preferred embodiment of the current invention are pharmaceutically acceptable salts of the compound of example 5.7.

A further preferred embodiment of the current invention are pharmaceutically acceptable salts of the compound of example 5.13.

A further preferred embodiment of the current invention are pharmaceutically acceptable salts of the compound of example 5.14.

A further preferred embodiment of the current invention are pharmaceutically acceptable salts of the compound of example 5.22.

A further preferred embodiment of the current invention are pharmaceutically acceptable salts of the compound of example 5.24.

A further preferred embodiment of the current invention are pharmaceutically acceptable salts of the compound of example 5.38.

A further preferred embodiment of the current invention are pharmaceutically acceptable salts of the compound of example 5.40.

A further embodiment of the current invention is a pharmaceutical composition comprising a therapeutically effective amount of at least one compound of formula I or a pharmaceutically acceptable salt thereof and one or more pharmaceutically acceptable excipients.

A further embodiment of the current invention is a compound of formula I or a pharmaceutically acceptable salt thereof for use as a medicament Furthermore, the present invention relates to the use of a compound of general formula I for treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes.

A pharmaceutical composition comprising additionally to a compound of formula I, a pharmaceutically active compound selected from the group consisting of an immunomodulatory agent, anti-inflammatory agent or a chemotherapeutic agent.

Furthermore, the present invention relates to the use of a compound of general formula I for the treatment and/or prevention of a disease and/or condition associated with or modulated by Vanin-1 or Vanin-2, especially Vanin-1, including but not limited to the treatment and/or prevention of inflammatory diseases, preferably inflammatory bowel diseases.

A further embodiment of the current invention is the use of a compound of formula I for treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes.

A further embodiment of the current invention is the use of a compound of formula I for treating a patient suffering from Crohn's disease, ulcerative colitis, systemic sclerosis, Non-Alcoholic Steatohepathitis (NASH), chronic obstructive pulmonary disease or atopic dermatitis, preferably Crohn's disease, ulcerative colitis, systemic sclerosis, Non-Alcoholic Steatohepathitis (NASH) or atopic dermatitis, particularly preferred from Crohn's disease or ulcerative colitis.

A further embodiment of the current invention is the use of a compound of formula I for treating a patient suffering from moderate to severe Crohn's disease.

A further embodiment of the current invention is the use of a compound of formula I for treating a patient suffering from ulcerative colitis.

A further embodiment of the current invention is the use of a compound of formula I for treating a patient suffering from atopic dermatitis.

A further embodiment of the current invention is the use of a compound of formula I for treating a patient suffering from NASH.

In a further embodiment, there is provided a method of treating a disease chosen from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes comprising administering to a patient a therapeutically effective amount of a compound according to the first embodiment or any of its related embodiments or a pharmaceutically acceptable salt thereof.

In a further embodiment, there is provided a process for preparation of a compound according to the first embodiment or any of its related embodiments by the methods shown herein below.

In a further aspect the present invention relates to a compound of general formula 1 for use in the treatment and/or prevention of above mentioned diseases and conditions.

In a further aspect the present invention relates to the use of a compound of general formula 1 for the preparation of a medicament for the treatment and/or prevention of above mentioned diseases and conditions.

In a further aspect the present invention relates to methods for the treatment or prevention of above mentioned diseases and conditions, which method comprises the administration of an effective amount of a compound of general formula 1 to a human being.

The actual pharmaceutically effective amount or therapeutic dosage will usually depend on factors known by those skilled in the art such as age and weight of the patient, route of administration and severity of disease. In any case the compounds will be administered at dosages and in a manner which allows a pharmaceutically effective amount to be delivered based upon patient's unique condition.

A further embodiment of the current invention is a pharmaceutical composition comprising additionally to a compound of formula I, a pharmaceutically active compound selected from the group consisting of an immunomodulatory agent, anti-inflammatory agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists, IL12/23 and IL23 antagonists, α4β7 integrin blocking antibodies, non-selective and selective JAK kinase inhibitors and methotrexate, but also combinations of two or three active substances.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, (O)$_2$S, CN (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

The numeration of the atoms of a substituent starts with the atom which is closest to the core or to the group to which the substituent is attached.

For example, the term "3-carboxypropyl-group" represents the following substituent:

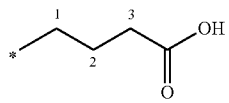

wherein the carboxy group is attached to the third carbon atom of the propyl group. The terms "1-methylpropyl-", "2,2-dimethylpropyl-" or "cyclopropylmethyl-" group represent the following groups:

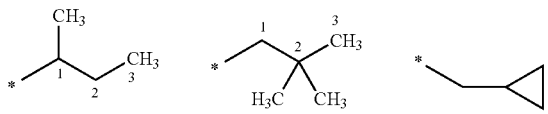

The asterisk may be used in sub-formulas to indicate the bond which is connected to the core molecule as defined.

The term "substituted" as used herein, means that any one or more hydrogens on the designated atom is replaced with a selection from the indicated group, provided that the designated atom's normal valence is not exceeded, and that the substitution results in a stable compound. Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents. Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid, preferably strong acid, or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals $H_3C-$, $H_3C-CH_2-$, $H_3C-CH_2-CH_2-$, $H_3C-CH(CH_3)-$, $H_3C-CH_2-CH_2-CH_2-$, $H_3C-CH_2-CH(CH_3)-$, $H_3C-CH(CH_3)-CH_2-$, $H_3C-C(CH_3)_2-$, $H_3C-CH_2-CH_2-CH_2-CH_2-$, $H_3C-CH_2-CH_2-CH(CH_3)-$, $H_3C-CH_2-CH(CH_3)-CH_2-$, $H_3C-CH(CH_3)-CH_2-CH_2-$, $H_3C-CH_2-C(CH_3)_2-$, $H_3C-C(CH_3)_2-CH_2-$, $H_3C-CH(CH_3)-CH(CH_3)-$ and $H_3C-CH_2-CH(CH_2CH_3)-$.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "carbocyclyl" or "carbocycle" as used either alone or in combination with another radical, means a mono- bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

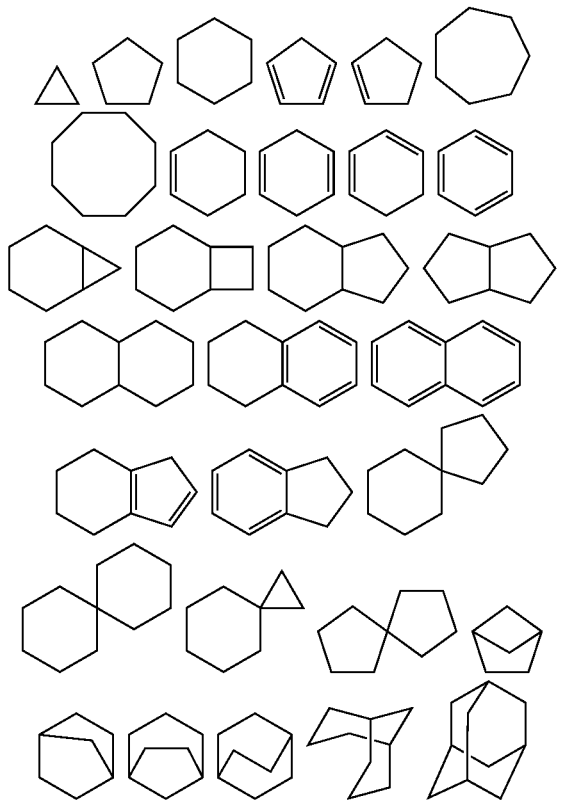

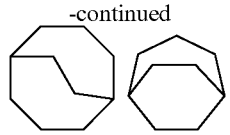

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms.

Thus, the term "heterocyclyl" or "heterocycle" includes the following exemplary structures which are not depicted as radicals as each form are optionally attached through a covalent bond to any atom so long as appropriate valences are maintained:

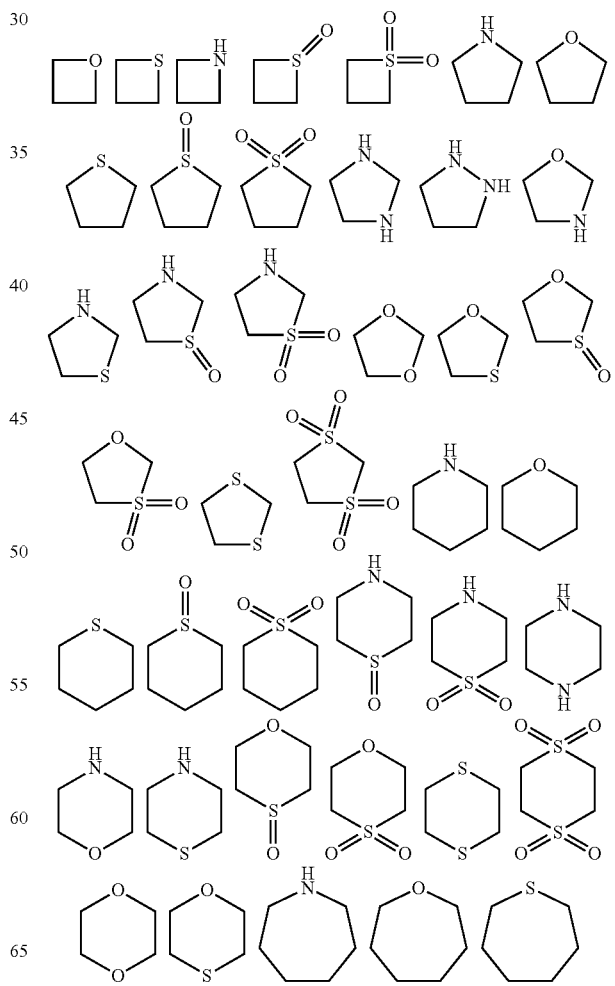

-continued
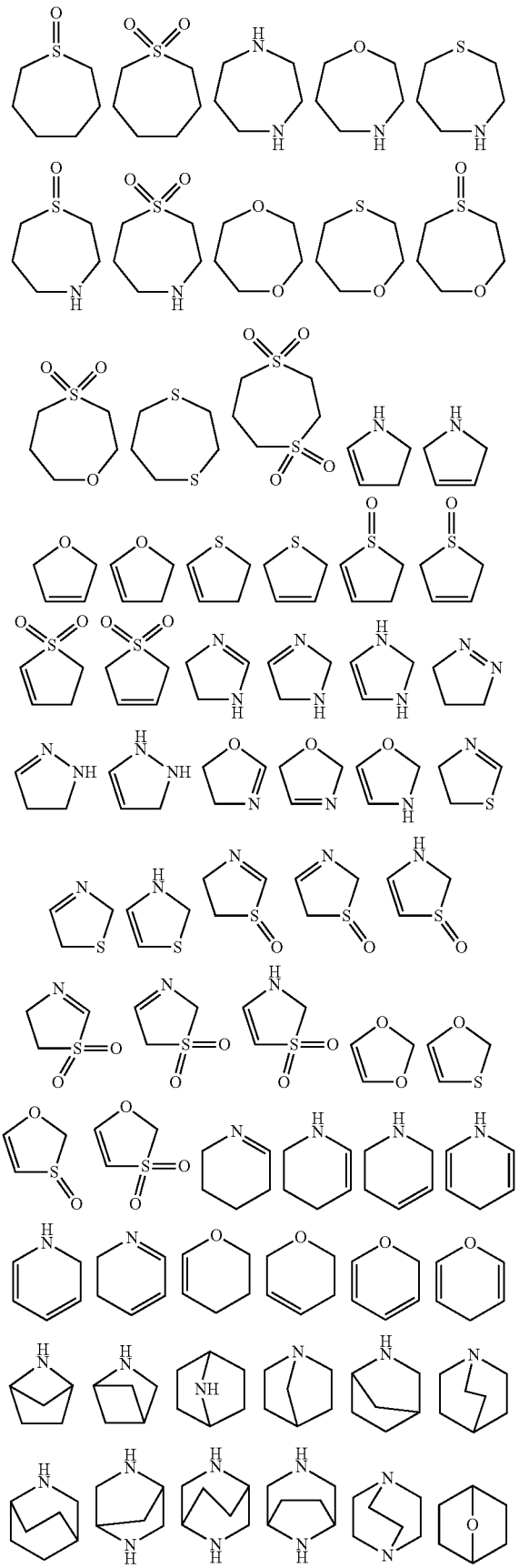
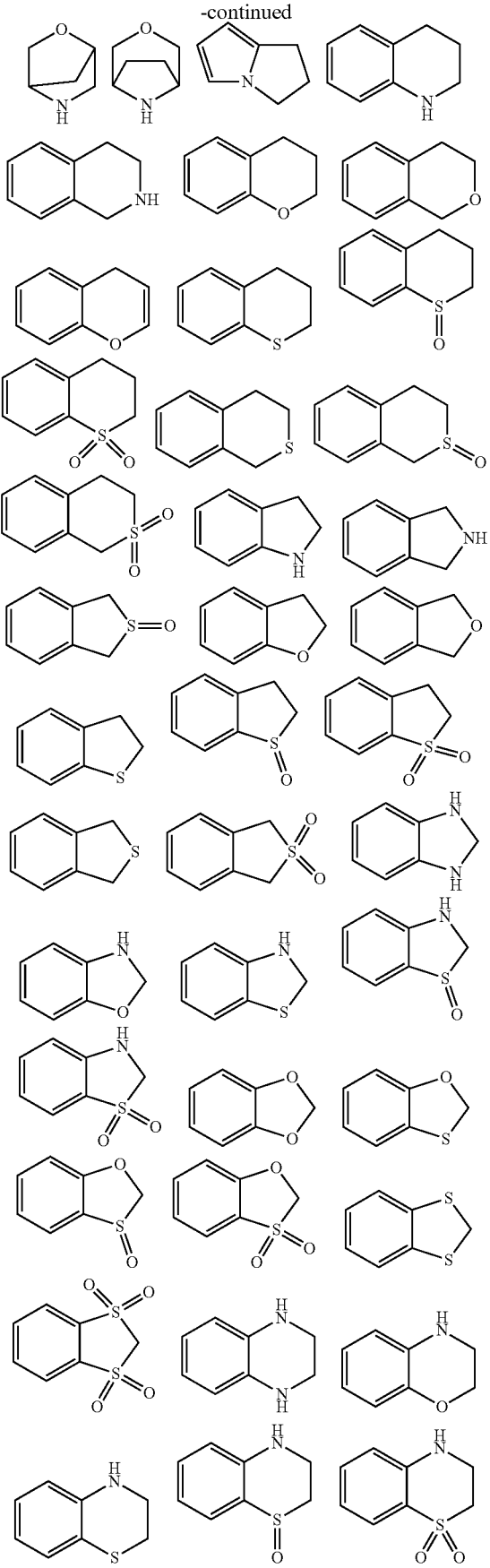

-continued

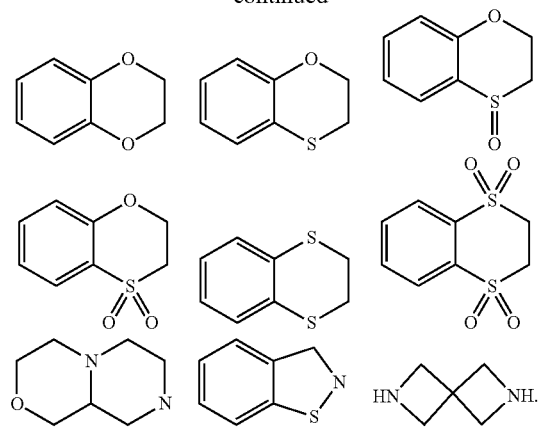

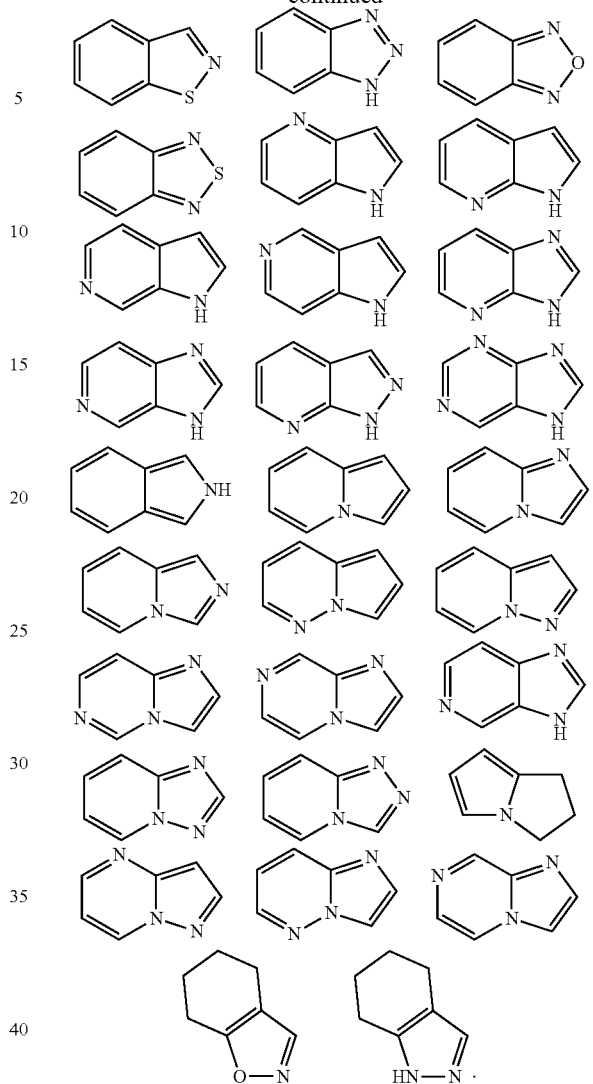

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form are optionally attached through a covalent bond to any atom so long as appropriate valences are maintained:

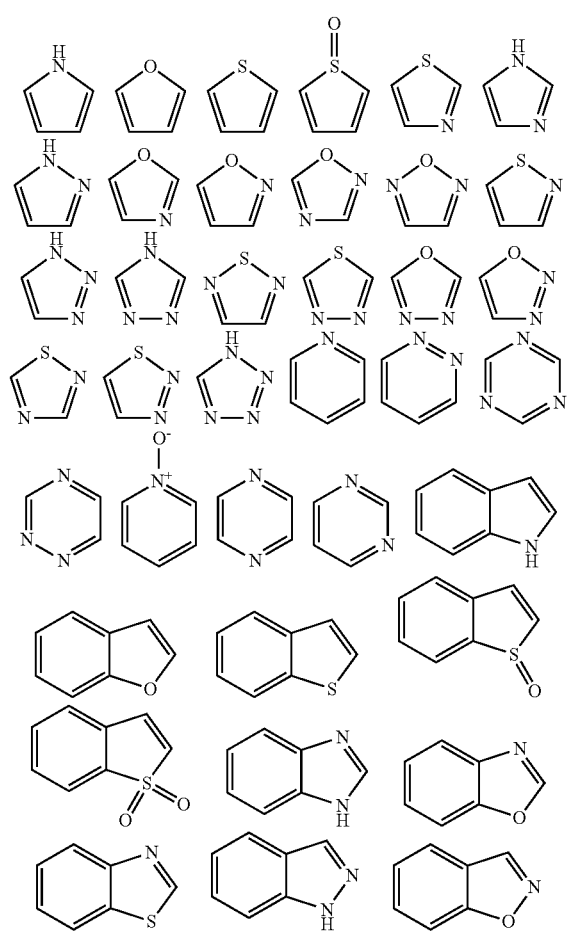

Many of the terms given above may be used repeatedly in the definition of a formula or group and in each case have one of the meanings given above, independently of one another.

Suitable preparations for administering the compounds of formula 1 will be apparent to those with ordinary skill in the art and include for example tablets, pills, capsules, suppositories, lozenges, troches, solutions, syrups, elixirs, sachets, injectables, inhalatives and powders etc., preferably tablets.

Suitable tablets may be obtained, for example, by mixing one or more compounds according to formula I with known excipients, for example inert diluents, carriers, disintegrants, adjuvants, surfactants, binders and/or lubricants.

By a therapeutically effective amount for the purposes of this invention is meant a quantity of substance that is capable of obviating symptoms of illness or alleviating these symptoms, or which prolong the survival of a treated patient.

List of Abbreviations

| ACN | acetonitrile |
|---|---|
| Alox | aluminium oxide |
| Aq. | aqueous |

| | |
|---|---|
| ° C. | degree Celsius |
| CyH | cyclohexane |
| conc. | concentrated |
| DCC | N,N'-dicyclohexylmethanediimine |
| DCM | dichloro methane |
| DIPE | diisopropylether |
| DIPEA | N,N-diisopropylethylamine |
| DMF | N,N-dimethylformamide |
| DMSO | dimethyl sulfoxide |
| ESI-MS | electrospray ionisation mass spectrometry |
| Et2O | diethylether |
| EtOAc | ethyl acetate |
| ex | example |
| eq | equivalent |
| h | hour |
| HATU | N,N,N',N'-tetramethyl-O-(7-azabenzotriazol-1-yl)uronium hexafluorophosphate |
| HCl | hydrochlorid acid |
| HNO3 | nitric acid |
| HOAc | acetic acid |
| HPLC | high performance liquid chromatography |
| LiHMDS | lithium-bis(trimethylsilyl)amid |
| MeOH | methanol |
| NaHCO3 | sodium bicarbonate |
| min | minute |
| mL | milliliter |
| Pd/C | palladium on activated carbon |
| Pd(dppf)Cl2 | [1,1'-Bis(diphenylphosphino)ferrocene]dichloropalladium(II) |
| PE | petroleum ether |
| RT | room temperature (about 20° C.) |
| sat. | saturated |
| TEA | triethylamine |
| TFA | trifluoroacetic acid |
| THF | tetrahydrofuran |
| TLC | thin-layer chromatography on SiO2 |

Preparation of the Compounds According to the Invention
General Synthetic Methods The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula (I) may be prepared as shown in Scheme I below.

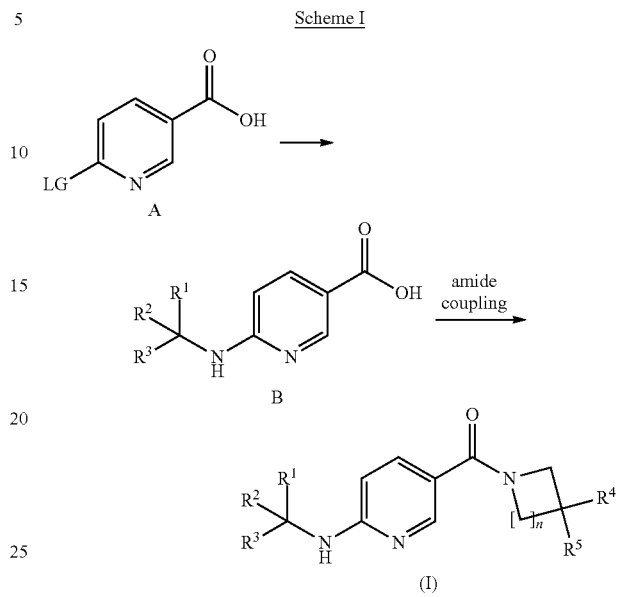

In scheme I, pyridine A, is treated with an appropriate primary amine under elevated temperature to generate pyridine B. An amide coupling (e.g. TBTU or HATU as coupling reagent) with an appropriate heterocycle as next step affords the compound of general formula (I).

Alternatively compounds of formula (I) may be prepared as shown in Scheme II below.

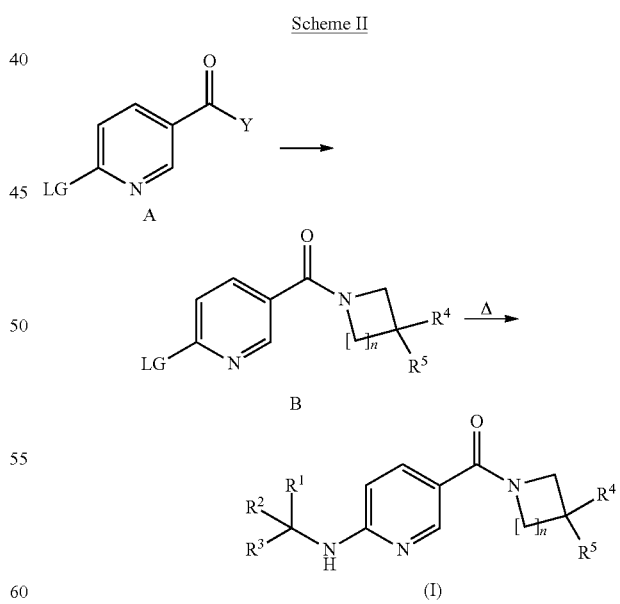

In scheme II, acid chloride (Y=Cl) A, is treated with an appropriate heterocycle to generate pyridine B. The leaving group in pyridine B can be replaced by an appropriate primary amine using elevated temperature to afford the compound of general formula (I).

The amines used in the previously described reactions can be obtained by using methods known to those skilled in the art, as exemplified in the Scheme III below:

Scheme III

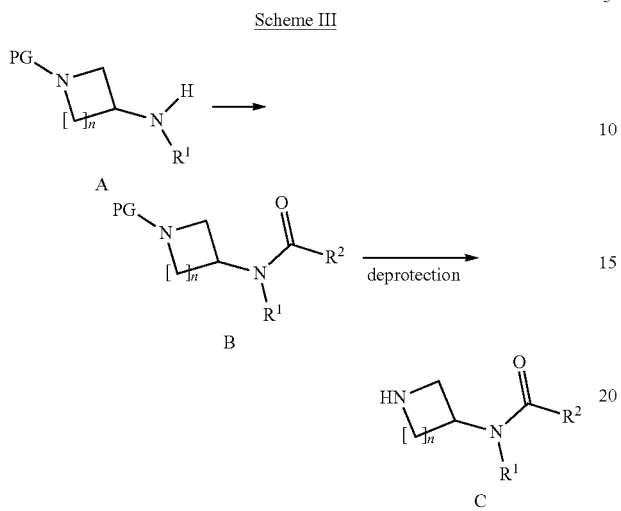

In scheme III, amine A is acylated with an appropriate acylating agent to generate amide B which can be further deprotected (e.g. HCl or TFA for PG=BOC) to yield the desired amine C.

A further option of generating these desired amines is depicted in Scheme IV below:

Scheme IV

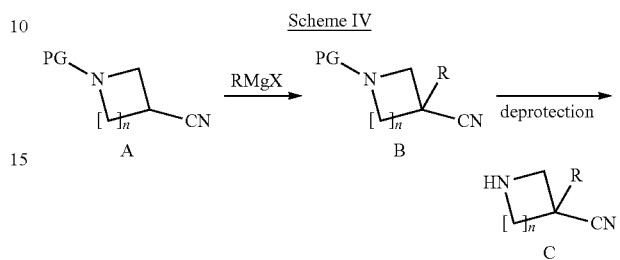

In scheme IV, nitrile A is treated with an alkylating agent to generate nitrile B and subsequently deprotected (e.g. HCl or TFA for PG=BOC) to yield the amine C.

Compounds of formula (II) may be prepared as shown in Scheme V:

Scheme V

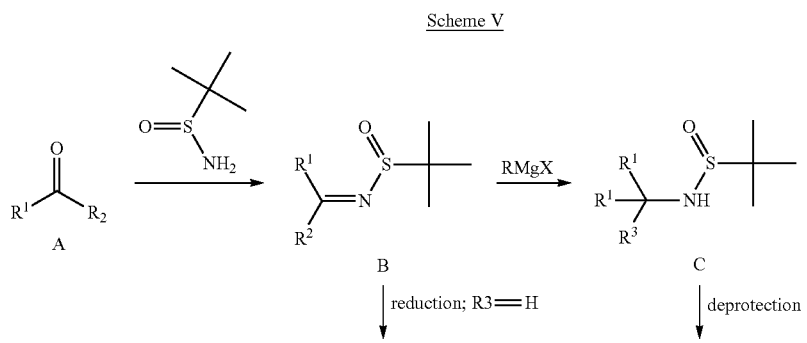

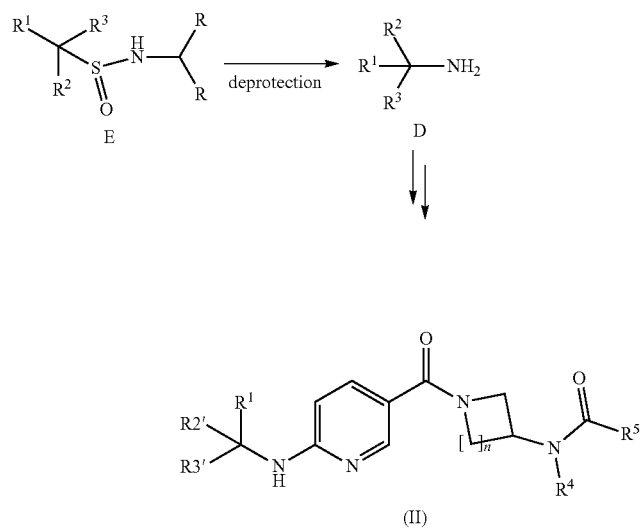

In scheme V, a ketone or aldehyde A is reacted with an appropriate auxiliary to yield compound B. This imin is either reduced or further alkylated with an appropriate alkylation reagent, i.e. a Grignard reagent, to yield intermediates C or E, respectively. After deprotection to amine D (i.e. with strong acids), compounds II are then obtained as depicted in schemes I and II.

SYNTHETIC EXAMPLES

The Examples that follow are intended to illustrate the present invention without restricting it. The terms "ambient temperature" and "room temperature" are used interchangeably and designate a temperature of about 20° C., e.g. between 19 and 24° C.

Preparation of Starting Compounds

Example I

Example I.1 (General Route)

Methyl 6-[({imidazo[1,2-a]pyridin-3-yl}methyl)amino]pyridine-3-carboxylate

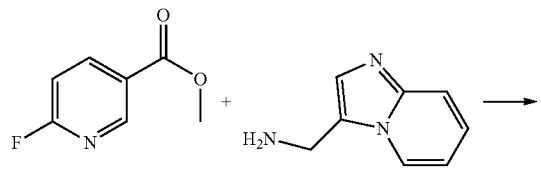

A mixture of 0.60 g (3.84 mmol) methyl 6-fluoropyridine-3-carboxylate, 0.56 g (3.84 mmol) {imidazo[1,2-a]pyridin-3-yl}methanamine (CAS No. 160771-89-1), 2.63 mL (15.4 mmol) DIPEA and 6 mL DMSO is stirred at 120° C. for 6 h. The mixture is diluted with EtOAc and is washed with a mixture of sat. NaHCO₃ solution and water (1/1). The organic layer is dried and the solvent is removed in vacuo.

The crude product is purified by HPLC (ACN/H₂O/NH₄OH).

$C_{15}H_{14}N_4O_2$ (M=282.3 g/mol)
ESI-MS: 283 [M+H]+
$R_t$ (HPLC): 0.79 min (method C)

Example II

Example II.1

6-[({Imidazo[1,2-a]pyridin-3-yl}methyl)amino]pyridine-3-carboxylic acid

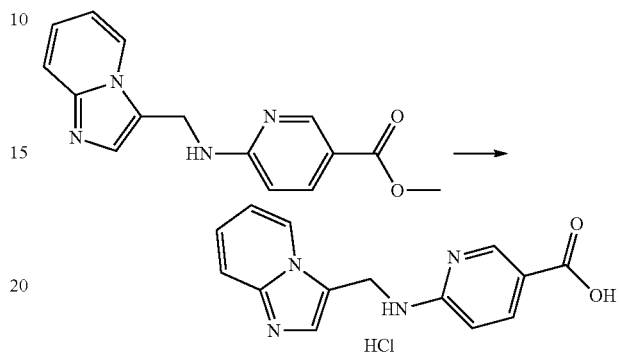

A mixture of 0.42 g (1.47 mmol) methyl 6-[({imidazo[1,2-a]pyridin-3-yl}methyl)amino]pyridine-3-carboxylate (ex. 1.1) and 5 mL HCl (6 mol/L) is stirred at 90° C. for 4 h. After cooling down to RT the solvent is removed in vacuo to obtain the product.

$C_{14}H_{12}N_4O_2$*HCl (M=304.7 g/mol)
ESI-MS: 269 [M+H]+
$R_t$ (HPLC): 0.10 min (method A)

Example III

Example III.1 (General Route)

3-[(3S)-Pyrrolidin-3-yl]-1,3-oxazolidin-2-one hydrochloride

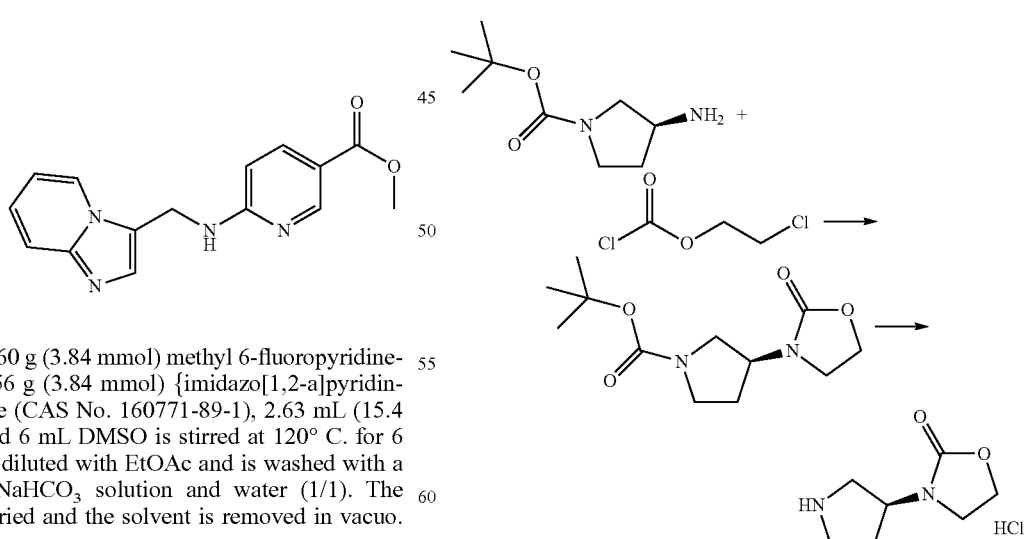

A mixture of 2.00 g (10.7 mmol) tert-butyl (3S)-3-aminopyrrolidine-1-carboxylate in 0.5 mL DCM and 4 mL NaOH (50%) is cooled to 0° C. A solution of 1.38 g (9.66 mmol) 2-chloroethyl carbonochloridate in 0.5 mL DCM is added dropwise and the reaction mixture is stirred at 0° for 1 h. 3.48 g (5.37 mmol) tetrabutylammonium hydroxide (40% in MeOH) is added and the mixture is stirred overnight at RT. The mixture is quenched with H$_2$O and extracted with DCM. The combined organic layers are dried over a phase separator cartridge and the solvent is removed in vacuo.

The crude product is purified by column chromatography (silica gel; CyH/EtOAc) and the solvents are removed in vacuo.

C$_{12}$H$_{20}$N$_2$O$_4$ (M=256.3 g/mol)
ESI-MS: 201 [M-tBU+H]$^+$
R$_t$ (HPLC): 0.82 min (method C)

The above mentioned product is added to 2.5 mL dioxane, 5 mL (20.0 mmol) HCl in dioxane (4 mol/L) and some MeOH and the mixture is stirred overnight at RT. The solvent is removed in vacuo to obtain the product.

C$_7$H$_{12}$N$_2$O$_2$*HCl (M=192.6 g/mol)
ESI-MS: 157 [M+H]+
R$_t$ (HPLC): 0.17 min (method C)

The following compounds are prepared according to the general procedure (example 111.1) described above:

| Ex. | Starting materials | Structure | ESI-MS | HPLC Rt [min] (method) |
|---|---|---|---|---|
| 111.2 | 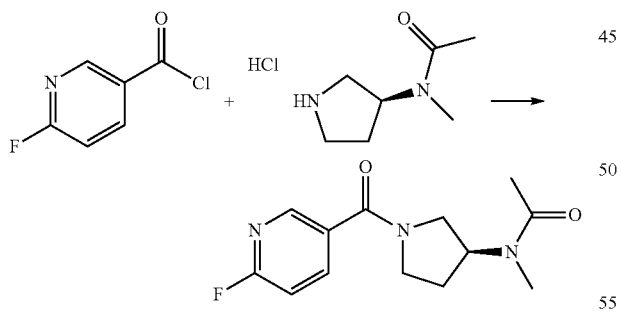 | 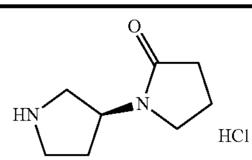 | 155 [M + H]$^+$ | 0.27 (C) |

Example IV

Example IV.1 (General Route)

N-[(3S)-1-(6-Fluoropyridine-3-carbonyl)pyrrolidin-3-yl]-N-methylacetamide

To 4.00 g (22.4 mmol) N-methyl-N-[(3S)-pyrrolidin-3-yl]acetamide hydrochloride and 14.8 mL (106.6 mmol) TEA in 30 mL DCM are added dropwise 3.40 g (21.3 mmol) 2-fluoropyridine-5-carbonyl chloride (CAS No. 65352-94-5) dissolved in 5 mL DCM at 0° C. After stirring for 10 min at 0° C., the reaction mixture is filtered and purified by column chromatography (silica gel; DCM/MeOH, 98/2-85/15).

C$_{13}$H$_{16}$FN$_3$O$_2$ (M=265.3 g/mol)
ESI-MS: 266 [M+H]$^+$
R$_t$ (HPLC): 0.63 min (method A)

Example V

Example V.1 (General Route)

{Thieno[3,2-c]pyridin-7-yl}methanamine

A mixture of 600 mg (3.08 mmol) 4-chlorothieno[3,2-c]pyridine-7-carbonitrile, 500 mg Pd/C (10%) and 25 mL NH$_3$ in MeOH is hydrogenated at RT and 3 bar H$_2$ pressure for 20 h. The reaction mixture is filtered and the solvent is removed in vacuo. The crude product is dissolved in DMF and purified by HPLC (ACN/H$_2$O/NH$_4$OH) to obtain the product.

C$_8$H$_8$N$_2$S (M=164.2 g/mol)
ESI-MS: 165 [M+H]+
R$_t$ (HPLC): 0.62 min (method C)

Example VI

Example VI.1 (General Route)

N-methyl-N-[(3S)-pyrrolidin-3-yl]cyclobutanecarboxamide hydrochloride

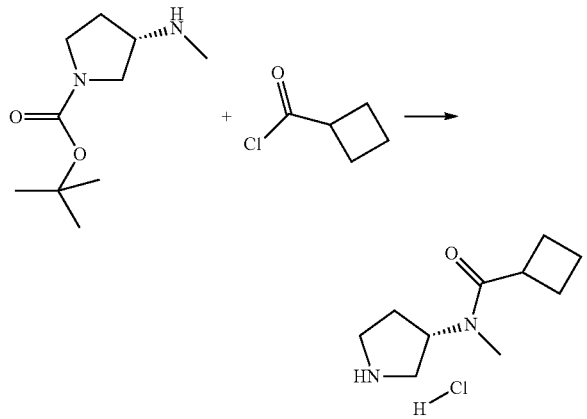

To 1.00 g (4.99 mmol) (S)-tert-butyl-3-(methylamino)pyrrolidine-1-carboxylate in 5 mL THF are added 0.86 mL (4.99 mmol) DIPEA and dropwise 0.59 g (4.99 mmol) cyclobutanecarbonyl chloride. After stirring overnight at RT, the mixture is filtered, washed with 10 mL THF and the filtrate is concentrated in vacuo. The residue is stirred in 50 mL ethanolic HCl (1.25 M) for 2 h at RT. The mixture is concentrated by evaporation and the residue is dissolved in 30 mL isopropanol. The mixture is concentrated by evaporation.

$C_{10}H_{18}N_2O$*HCl (M=218.7 g/mol)
ESI-MS: 183 [M+H]+
$R_t$ (HPLC): 0.96 min (method B)

Example VII

Example VII.1 (General Route)

(R)-2-Methyl-N-[(1Z)-(1-methyl-1H-indazol-4-yl)methylidene]propane-2-sulfinamide

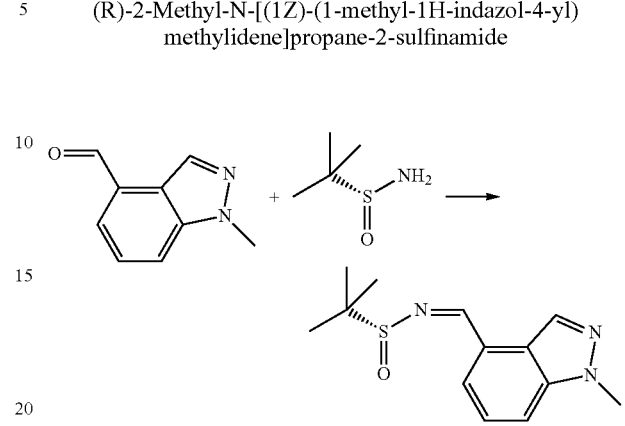

A mixture of 1.50 g (9.37 mmol) 1-methyl-1H-indazole-4-carbaldehyde, 1.36 g (11.2 mmol) (R)-2-methylpropane-2-sulfinamide, 5.55 mL (18.7 mmol) tetrakis(propan-2-yloxy)titanium and 20 mL THF is stirred at 70° C. for 1 h.

After cooling down to RT the mixture is diluted with 50 mL sat. NaCl solution. The obtained precipitate is filtered off over celite and washed with EtOAc. The organic layer is separated and washed with sat. NaCl solution. Then the organic layer is dried over a phase separator cartridge and the solvents are removed in vacuo to obtain the product.

$C_{13}H_{17}N_3OS$ (M=263.4 g/mol)
ESI-MS: 264 [M+H]+
$R_t$ (HPLC): 0.92 min (method C)

The following compounds are prepared according to the general procedure (example VII.1) described above:

| Ex. | Starting materials | | Structure | Reaction conditions | ESI-MS | HPLC Rt [min] (method) |
|---|---|---|---|---|---|---|
| VII.2 | [indazole with acetyl group] | [sulfinamide] | [sulfinyl imine indazole product] | 80° C., WE | 264 [M + H]+ | 0.82 (C) |
| VII.3 | [1-methyl-indazole-4-carbaldehyde] | [sulfinamide] | [sulfinyl imine product] | | 264 [M + H]+ | 0.91 (C) |
| VII.4 | [1-methyl-indazole-5-carbaldehyde] | [sulfinamide] | [sulfinyl imine product] | | 264 [M + H]+ | 0.94 (C) |

Example VIII

Example VIII.1 (General Route)

(R)-2-Methyl-N-[(1S)-1-(1-methyl-1H-indazol-4-yl)ethyl]propane-2-sulfinamide (R)-2-Methyl-N-[(1R)-1-(1-methyl-1H-indazol-4-yl)ethyl]propane-2-sulfinamide

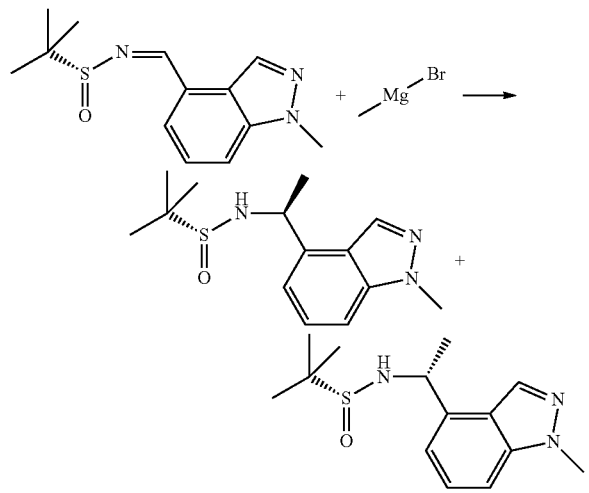

To a mixture of 2.46 g (9.34 mmol) (R)-2-methyl-N-[(1Z)-(1-methyl-1H-indazol-4-yl)methylidene]propane-2-sulfinamide in 25 mL DCM are added dropwise 6.23 mL (18.5 mmol) bromo(methyl)magnesium (3 mol/L) at −50° C. and the mixture is stirred for 1 h at −50° C. and overnight at RT. Additional 6.23 mL (18.5 mmol) bromo(methyl)magnesium (3 mol/L) are added dropwise at RT and stirred for 1 h. Then the mixture is diluted with 50 mL sat. NH4Cl solution and extracted 2× with DCM. The organic layer is washed with sat. NaCl solution, dried and the solvent is removed in vacuo.

The crude product is purified by HPLC (ACN/H$_2$O/NH$_4$OH) to obtain the products. The organic solvent is removed in vacuo and the remaining solution is diluted with sat. NaCl solution and extracted 2× with Methyl-THF. The combined organic layer is dried over Na$_2$SO$_4$, filtered and the solvent is removed in vacuo to obtain the product.

Product A:
C$_{14}$H$_{21}$N$_3$OS (M=279.4 g/mol)
ESI-MS: 280 [M+H]$^+$
R$_t$ (HPLC): 0.87 min (method A)

Product B:
C$_{14}$H$_{21}$N$_3$OS (M=279.4 g/mol)
ESI-MS: 280 [M+H]$^+$
R$_t$ (HPLC): 0.90 min (method A)

The following compounds are prepared according to the general procedure (example VIII.1) described above:

| Ex. | Starting material | Structure | Reaction conditions | ESI-MS | HPLC Rt [min] (method) |
|---|---|---|---|---|---|
| VIII.2.A | 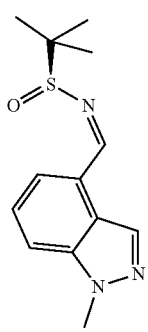 | 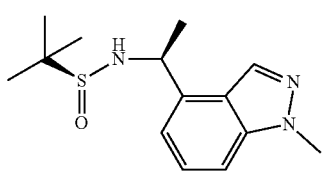 [SMILES: C[C@H](N[S@@](=O)C(C)(C)C)c1cccc2c1cnn2C] | | 280 [M + H]$^+$ | 2.82 (I) |
| VIII.2.B | | 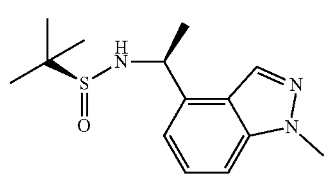 | | 280 [M + H]$^+$ | 3.41 (I) |

| Ex. | Starting material | Structure | Reaction conditions | ESI-MS | HPLC Rt [min] (method) |
|---|---|---|---|---|---|
| VIII.3.A | | 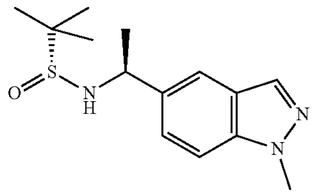 [SMILES: C[C@H](N[S@](=O)C(C)(C)C)c1ccc2c(cnn2C)c1] | | 280 [M + H]⁺ | 0.86 (C) |
| VIII.3.B | | 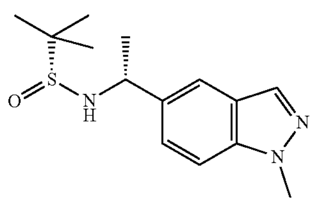 [SMILES: C[C@@H](N[S@](=O)C(C)(C)C)c1ccc2c(cnn2C)c1] | | 280 [M + H]⁺ | 0.89 (C) |

Example IX

Example IX.1 (General Route)

(1S)-1-(1-Methyl-1H-indazol-4-yl)ethan-1-amine hydrochloride

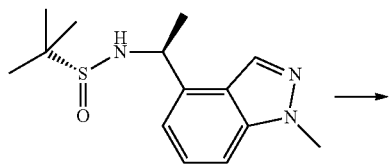
→
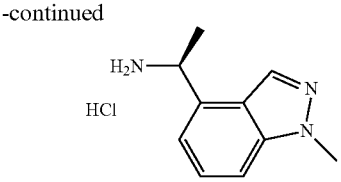

To a mixture of 1.52 g (5.43 mmol) (R)-2-methyl-N-[(1S)-1-(1-methyl-1H-indazol-4-yl)ethyl]propane-2-sulfinamide in 15 mL THF are added 5 mL HCl (4 mol/L in dioxane) at 0° C.

The reaction mixture is stirred until RT has been reached and the obtained precipitate is filtered off and dried in vacuo to obtain the product.

$C_{10}H_{13}N_3$*HCl (M=211.7 g/mol)
ESI-MS: 176 [M+H]⁺
$R_t$ (HPLC): 0.59 min (method A)

The following compounds are prepared according to the general procedure (example IX.1) described above:

| Ex. | Starting material | Structure | Reaction conditions | ESI-MS | HPLC Rt [min] (method) |
|---|---|---|---|---|---|
| IX.2 | 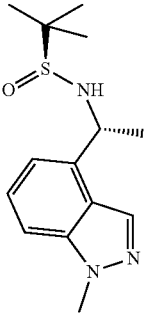 | 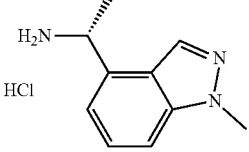 | | 176 [M + H]+ | 0.58 (A) |
| IX.3 | 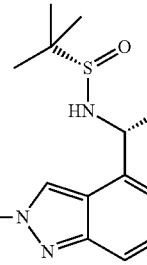 | 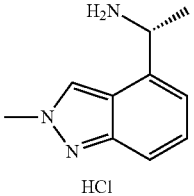 | precipitate is filtered off as product | 176 [M + H]+ | 0.67 (C) |
| IX.4 | 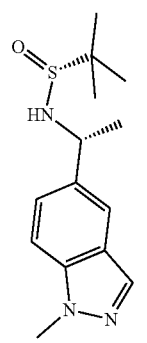 | 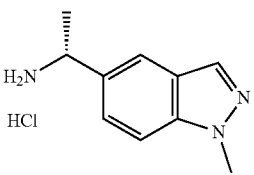 | precipitate is filtered off as product | 159 [M + H − NH3]+ | 0.90 (C) |
| IX.5 | 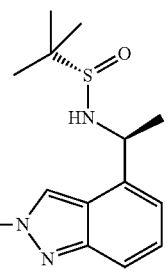 | 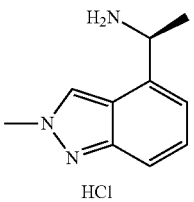 | precipitate is filtered off as product | 176 [M + H]+ | 0.65 (C) |
| IX.6 | 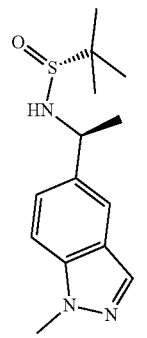 | 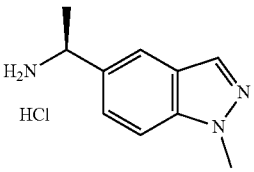 | precipitate is filtered off as product | 159 [M + H]+ | 0.70 (C) |

Example X

Example X.1 (General Route)

(1S)-1-(1H-Indazol-5-yl)ethan-1-amine hydrochloride

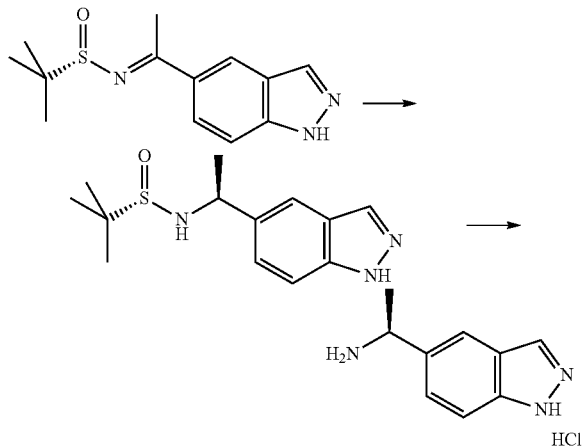

To a mixture of 0.44 g (1.67 mmol) (S)—N-[(1E)-1-(1H-indazol-5-yl)ethylidene]-2-methylpropane-2-sulfinamide (example VII.2) in 7 mL THF and 0.10 mL H$_2$O are added 0.19 g (5.00 mmol) sodiumborohydride at −50° C. The reaction mixture is stirred 1.25 h without icebath. The mixture is diluted with sat. NH$_4$Cl solution and extracted 2× with EtOAc. Then the organic layer is dried over a phase separator cartridge and the solvents are removed in vacuo. The crude product is purified by HPLC (ACN/H$_2$O/NH$_4$OH).

C$_{13}$H$_{19}$N$_3$OS (M=265.4 g/mol)
ESI-MS: 266 [M+H]$^+$
R$_t$ (HPLC): 0.83 min (method C)

To the above mentioned product are added 2 mL THF and 2 mL HCl (4 mol/L in dioxane) and the mixture is stirred 45 min at RT. The solvents are removed in vacuo to obtain the product.

C$_9$H$_{11}$N$_3$*HCl (M=197.7 g/mol)
ESI-MS: 145 [M+H]$^+$
R$_t$ (HPLC): 0.62 min (method C)

Example XI

Example XI.1 (General Route)

tert-Butyl N-[(1S)-1-[(2-amino-4-chlorophenyl)carbamoyl]ethyl]carbamate

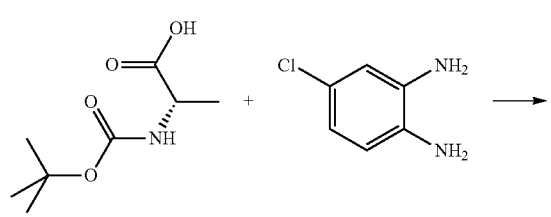

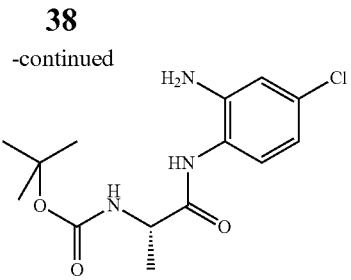

To a mixture of 25.0 g (132 mmol) (2S)-2-{[(tert-butoxy)carbonyl]amino}propanoic acid and 18.8 g (132 mmol) 4-chlorobenzene-1,2-diamine in 50 mL THF is added dropwise a solution of 30.0 g (145 mmol) DCC and 60 mL THF under icecooling. The reaction mixture is stirred at RT overnight. The precipitate is filtered off and washed with THF. The filtrate is concentrated in vacuo to dryness. The crude is treated with a mixture of Et$_2$O/PE (1/1) and the obtained precipitate is filtered off. The solid is dried at 40° C. in vacuo to give the product.

C$_{14}$H$_{20}$ClN$_3$O$_3$ (M=313.8 g/mol)
Rf (TLC): 0.3 (CyH/EtOAc 1/1)

Example XII

Example XII.1 (General Route)

tert-Butyl N-[(1S)-1-(5-chloro-1H-1,3-benzodiazol-2-yl)ethyl]carbamate

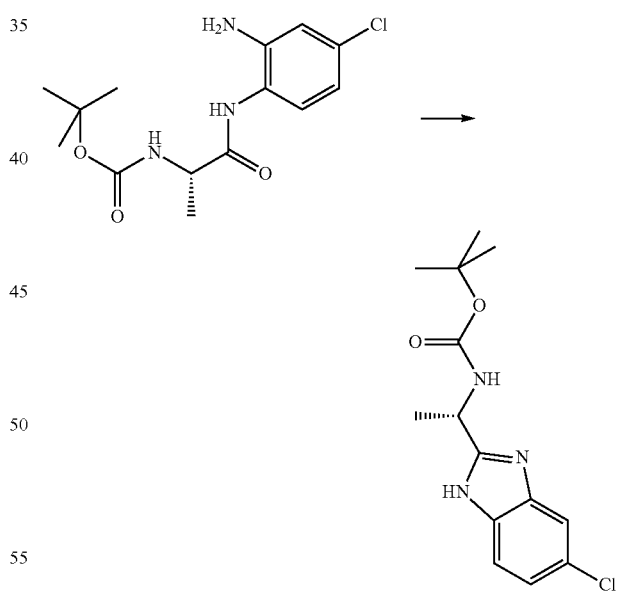

A mixture of 525 mg (1.67 mmol) tert-butyl N-[(1S)-1-[(2-amino-4-chlorophenyl)carbamoyl]ethyl]carbamate and 5 mL HOAc is stirred at 40° C. for 3 h. The mixture is poured onto ice and the precipitate is filtered off. The filtrate is concentrated in vacuo and treated with Et$_2$O. The precipitate is filtered off and the filtrate is concentrated to dryness in vacuo.

C$_{14}$H$_{18}$ClN$_3$O$_2$ (M=295.8 g/mol)
Rf (TLC): 0.35 (Et$_2$O/PE 2/1)

Example XIII

Example XIII.1 (General Route)

(1S)-1-(5-Chloro-1H-1,3-benzodiazol-2-yl)ethan-1-amine hydrochloride

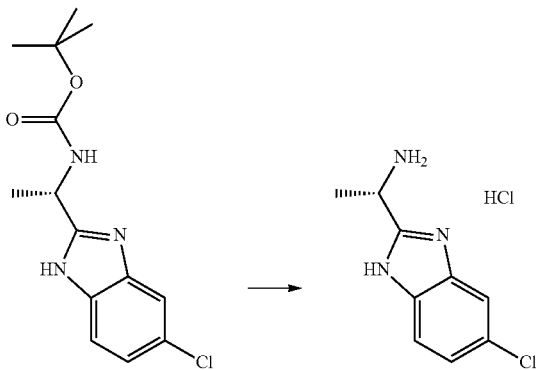 [SMILES: C[C@H](NC(=O)OC(C)(C)C)c1nc2cc(Cl)ccc2[nH]1 ; C[C@H](N)c1nc2cc(Cl)ccc2[nH]1 ; Cl]

To a mixture of 1.03 g (3.48 mmol) tert-butyl N-[(1S)-1-(5-chloro-1H-1,3-benzodiazol-2-yl)ethyl]carbamate in 10 mL EtOH are added 20 mL conc. HCl and the mixture is stirred at 80° C. for 2 h. The solvents are removed in vacuo and the residue is treated with EtOH. The precipitate is filtered off, washed with Et$_2$O and dried at 40° C. in vacuo to obtain the product as a blue powder.

Example XIV

Example XIV.1 (General Route)

tert-Butyl N-[(1S)-1-(5-chloro-6-fluoro-1H-1,3-benzodiazol-2-yl)ethyl]carbamate

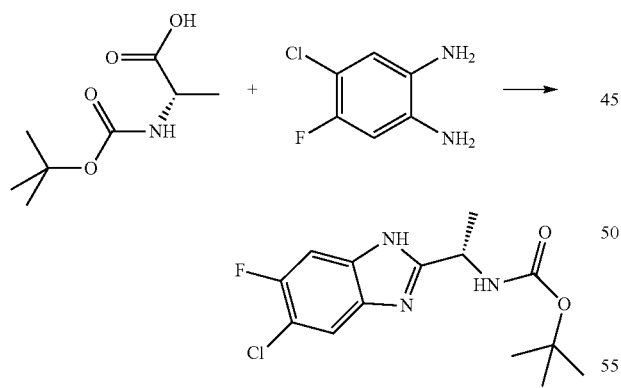

To a mixture of 3.78 g (20.0 mmol) (2S)-2-{[(tert-butoxy)carbonyl]amino}propanoic acid and 3.21 g (20.0 mmol) 4-chloro-5-fluorobenzene-1,2-diamine in 30 mL THF are added dropwise 4.54 g (22.0 mmol) DCC dissolved in 50 mL THF under icecooling and the reaction mixture is stirred at RT over the weekend. The obtained precipitate is filtered off, washed with THF and the filtrate is concentrated in vacuo to dryness. The residue is dissolved in 70 mL HOAc and the mixture is stirred at 55° C. for 4 h. The solvent is removed in vacuo and the crude product is dissolved in DCM and washed with H$_2$O and NaHCO$_3$ solution (5%). The organic layer is dried over Na$_2$SO$_4$ and the solvent is removed in vacuo. The crude product is purified by column chromatography (silica gel; DCM/EtOH; 1-3% EtOH) and triturated 2× with DIPE. The solid is filtered off and dried to obtain the product.

C$_{14}$H$_{17}$ClFN$_3$O$_2$ (M=313.8 g/mol)
Rf (TLC): 0.4 (PE/EtOAc 7/3)

Example XV

Example XV.1 (General Route)

(1S)-1-(5-Chloro-6-fluoro-1H-1,3-benzodiazol-2-yl)ethan-1-amine hydrochloride

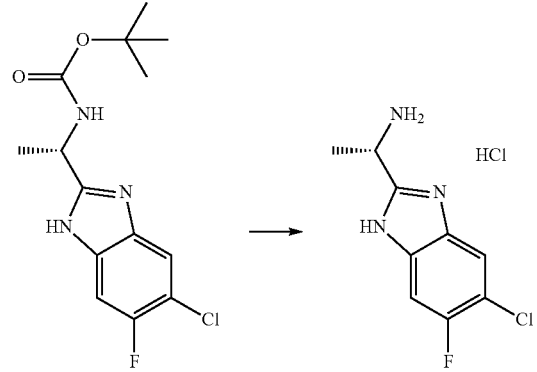 [SMILES: C[C@H](NC(=O)OC(C)(C)C)c1nc2cc(Cl)c(F)cc2[nH]1 ; C[C@H](N)c1nc2cc(Cl)c(F)cc2[nH]1 ; Cl]

A mixture of 2.60 g (8.29 mmol) tert-butyl N-[(1S)-1-(5-chloro-6-fluoro-1H-1,3-benzodiazol-2-yl)ethyl]carbamate and 70 mL HCl in EtOH is stirred at 50° C. for 1 h. After cooling down the obtained precipitate is filtered off, washed with cold EtOH and Et$_2$O and dried.

C$_9$H$_9$ClFN$_3$*HCl (M=250.1 g/mol)
Rf (TLC): 0.3 (DCM/EtOH 9/1)

Example XVI

Example XVI.1 (General Route)

(S)-2-Methyl-N-[(1E)-1-(2-methyl-2H-indazol-4-yl)ethylidene]propane-2-sulfinamide A mixture of 0.30 g (1.72 mmol) 1-(2-methyl-2H-indazol-4-yl)ethan-1-one, 0.31 g (2.58 mmol) (S)-2-methylpropane-2-sulfinamide, 1.72 mL (3.44 mmol) tetraethoxytitanium (2 mol/L) and 5 mL THF is stirred at 80° C. overnight.

After cooling down to RT the mixture is diluted with 50 mL sat. NaCl solution and 100 mL DCM. The obtained precipitate is filtered off and the layers are separated. The organic layer is dried and the solvents are removed in vacuo to obtain the crude product.

$C_{14}H_{19}N_3OS$ (M=277.4 g/mol)
ESI-MS: 278 [M+H]$^+$
R$_t$ (HPLC): 0.87 min (method C)

The following compounds are prepared according to the general procedure (example XVI.1) described above:

| Ex. | Starting materials | Structure | ESI-MS | HPLC Rt [min] (method) |
|---|---|---|---|---|
| XVI.2 | | 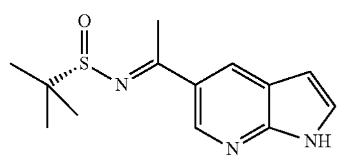 [SMILES: C/C(=N\[S@@](=O)C(C)(C)C)c1cnc2[nH]ccc2c1] | 263 [M + H]$^+$ | 0.78 (A) |

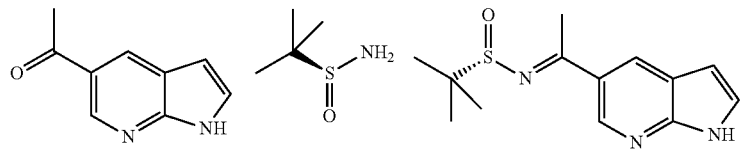

Example XVII

Example XVII.1 (General Route)

(S)-2-Methyl-N-[(1S)-1-(2-methyl-2H-indazol-4-yl)ethyl]propane-2-sulfinamide (S)-2-Methyl-N-[(1R)-1-(2-methyl-2H-indazol-4-yl)ethyl]propane-2-sulfinamide

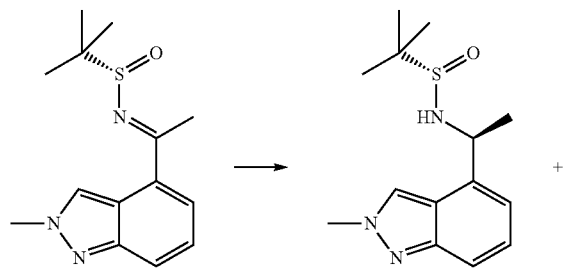

-continued

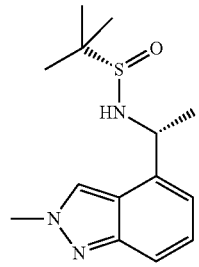

To a mixture of 0.48 g (1.73 mmol) (S)-2-methyl-N-[(1E)-1-(2-methyl-2H-indazol-4-yl)ethylidene]propane-2-sulfinamide and 5 mL THF is added 0.5 mL H$_2$O and the mixture is cooled to −50° C. Then 0.20 g (5.18 mmol) sodium boranuide is added and the mixture is allowed to come to RT.

The reaction mixture is washed with a mixture of sat. NaHCO$_3$ solution and H$_2$O (1/1). The organic layer is dried and the crude product is purified by HPLC (ACN/H$_2$O/NH$_4$OH)

Product A:
$C_{14}H_{21}N_3OS$ (M=279.4 g/mol)
ESI-MS: 280 [M+H]$^+$
R$_t$ (HPLC): 0.83 min (method C)

Product B:
$C_{14}H_{21}N_3OS$ (M=279.4 g/mol)
ESI-MS: 280 [M+H]$^+$
R$_t$ (HPLC): 0.79 min (method C)

The following compounds are prepared according to the general procedure (example XVII.1) described above:

| Ex. | Starting material | Structure | ESI-MS | HPLC Rt [min] (method) |
|---|---|---|---|---|
| XVII.2.A | | 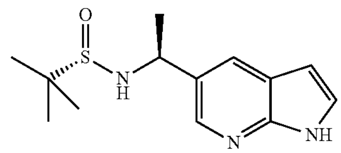 [SMILES: C[C@H](N[S@@](=O)C(C)(C)C)c1cnc2[nH]ccc2c1] | 266 [M + H]⁺ | 0.69 (A) |
| XVII.2.B | | 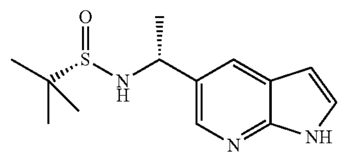 [SMILES: C[C@@H](N[S@@](=O)C(C)(C)C)c1cnc2[nH]ccc2c1] | 266 [M + H]⁺ | 0.66 (A) |

Example XVIII

Example XVIII.1 (General Route)

(S)—N-[(1E)-1-(4-Amino-3-nitrophenyl)ethylidene]-2-methylpropane-2-sulfinamide

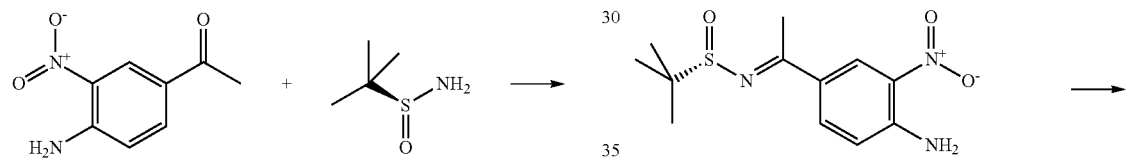

A mixture of 400 mg (2.00 mmol) 1-(4-amino-3-nitrophenyl)ethan-1-one, 296 mg (2.44 mmol) (S)-2-methylpropane-2-sulfinamide, 2.22 mL tetraethoxytitanium (2 mol/L) and 8 mL THF is stirred at 80° C. overnight.

After cooling down to RT the mixture is diluted with 50 mL of a mixture of sat. NaCl solution and H₂O (1/1). The obtained precipitate is filtered off, washed with EtOAc and the layers are separated. The organic layer is dried over Na₂SO₄, filtered and prepared for a column chromatography. The crude product is purified by column chromatography (silica gel, DCM/MeOH, 2-20% MeOH).

C₁₂H₁₇N₃O₃S (M=283.4 g/mol)

ESI-MS: 284 [M+H]⁺

R$_t$ (HPLC): 0.88 min (method C)

Example XIX

Example XIX.1 (General Route)

(S)—N-[(1S)-1-(4-Amino-3-nitrophenyl)ethyl]-2-methylpropane-2-sulfinamide

To a mixture of 565 mg (2.00 mmol) (S)—N-[(1E)-1-(4-amino-3-nitrophenyl)ethylidene]-2-methylpropane-2-sulfinamide in 11 mL THF is added 0.20 mL H₂O and the mixture is cooled to −50° C. Then 227 mg (5.98 mmol) sodium boranuide is added and the mixture is allowed to come to RT.

The reaction mixture is washed 2× with sat. NH₄Cl solution. The organic layer is dried over Na2SO4, filtered and the solvent is removed in vacuo to obtain the crude product.

C₁₂H₁₉N₃O₃S (M=285.4 g/mol)

ESI-MS: 286 [M+H]⁺

R$_t$ (HPLC): 0.85 min (method C)

Example XX

Example XX.1 (General Route)

(S)—N-[(1S)-1-(3,4-Diaminophenyl)ethyl]-2-methylpropane-2-sulfinamide

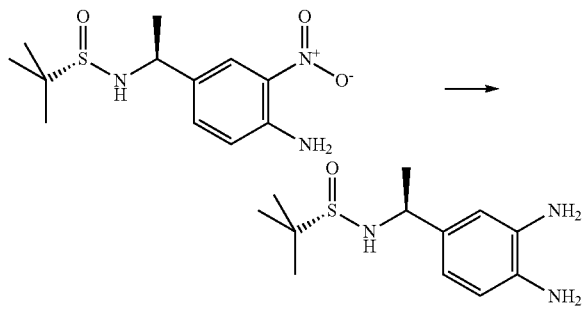

A mixture of 581 mg (2.00 mmol) (S)—N-[(1S)-1-(4-amino-3-nitrophenyl)ethyl]-2-methylpropane-2-sulfinamide 58.1 mg Pd/C and 10 mL THF is stirred at RT overnight at 3 bar $H_2$ pressure. The solvent is evaporated to obtain the crude product.

$C_{12}H_{21}N_3OS$ (M=255.4 g/mol)
ESI-MS: 256 $[M+H]^+$
$R_t$ (HPLC): 0.70 min (method C)

Example XXI

Example XXI.1 (General Route)

(1S)-1-(1H-1,3-Benzodiazol-6-yl)ethan-1-amine hydrochloride

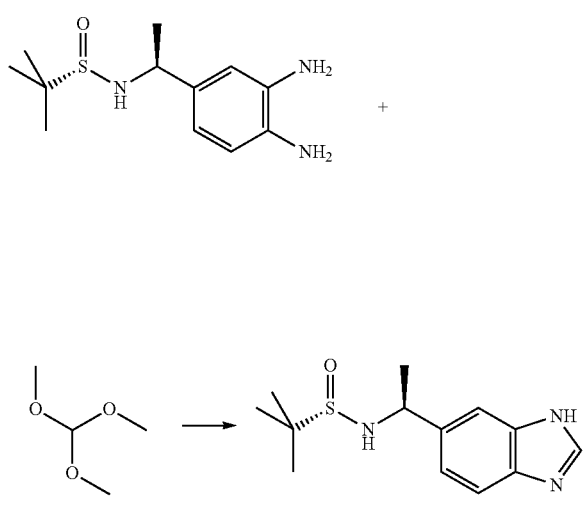

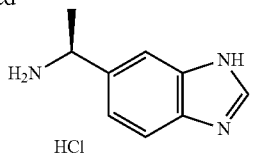

A mixture of 75.0 mg (0.29 mmol) (S)—N-[(1S)-1-(3,4-diaminophenyl)ethyl]-2-methylpropane-2-sulfinamide and 1 mL trimethoxymethane is stirred at reflux for 30 min. The reaction mixture is diluted with a mixture of sat. $NaHCO_3$ solution and $H_2O$ (1/1) and extracted 2× with EtOAc. The organic layer is dried over $Na_2SO_4$, filtered and the solvent is removed in vacuo.

$C_{13}H_{19}N_3OS$ (M=265.4 g/mol)
ESI-MS: 266 $[M+H]^+$
$R_t$ (HPLC): 0.75 min (method C)

The remaining product is dissolved in 2 mL THF and 0.5 mL HCl (4 mol/L in dioxane) is added at 0° C. The reaction mixture is allowed to come to RT and the solvents are removed in vacuo to obtain the product.

$C_9H_{11}N_3$*HCl (M=197.7 g/mol)
ESI-MS: 162 $[M+H]^+$
$R_t$ (HPLC): 0.10 min (method A)

Example XXII

Example XXII.1 (General Route)

(R)-N-[(1E)-(1H-Indazol-4-yl)methylidene]-2-methylpropane-2-sulfinamide

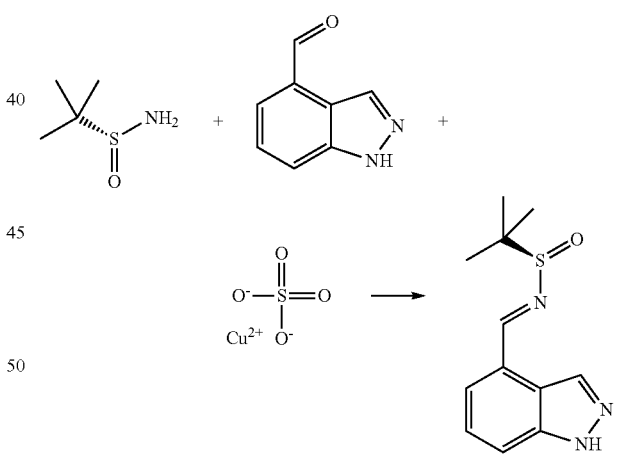

A mixture of 330 mg (2.72 mmol) (R)-2-methylpropane-2-sulfinamide and 5 mL DCM is added to 869 mg (5.45 mmol) dried copper(2+) sulfate and then 438 mg (3.00 mmol) 1H-indazole-4-carbaldehyde are added and the mixture is stirred at RT overnight. Additional dried copper(2+) sulfate is added and the mixture is stirred at RT for 1 d. The solvent is removed in vacuo and the crude product is purified by column chromatography (silica gel; CyH/EtOAc) to obtain the product.

$C_{12}H_{15}N_3OS$ (M=249.3 g/mol)
ESI-MS: 250 $[M+H]^+$
$R_t$ (HPLC): 0.87 min (method B)

Example XXIII

Example XXIII.1 (General Route)

(R)-N-[(1S)-1-(1H-indazol-4-yl)ethyl]-2-methylpropane-2-sulfinamide (R)-N-[(1R)-1-(1H-indazol-4-yl)ethyl]-2-methylpropane-2-sulfinamide

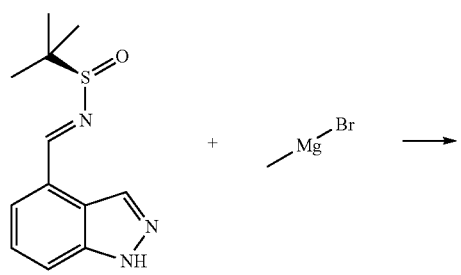

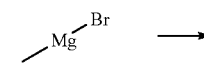

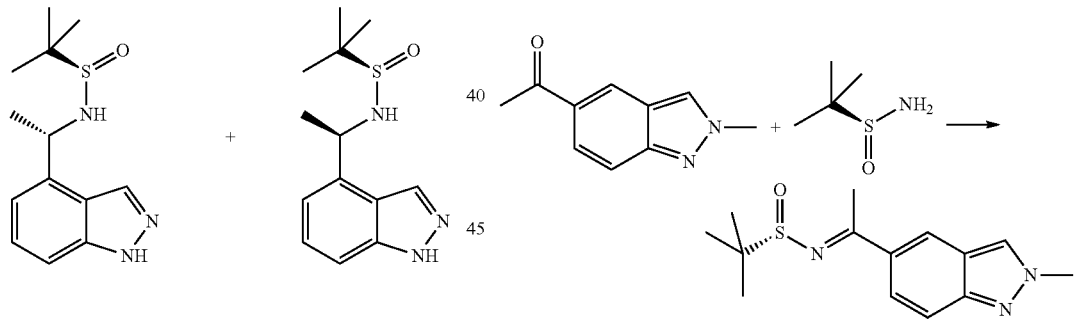

To a mixture of 220 mg (0.88 mmol) (R)-N-[(1E)-(1H-indazol-4-yl)methylidene]-2-methylpropane-2-sulfinamide in 10 mL DCM are added dropwise 618 L (1.85 mmol) bromo(methyl)magnesium (3 mol/L in Et$_2$O) at −48° C. and the mixture is stirred for 4 h. After achieving RT the solvents are removed in vacuo. The crude product is dissolved in DMF and purified by HPLC (ACN/H$_2$O/NH$_4$OH) to obtain the 2 products.

Product A:

$C_{13}H_{19}N_3OS$ (M=265.4 g/mol)

ESI-MS: 266 [M+H]$^+$

R$_t$ (HPLC): 0.76 min (method C)

Product B:

$C_{13}H_{19}N_3OS$ (M=265.4 g/mol)

ESI-MS: 266 [M+H]$^+$

R$_t$ (HPLC): 0.80 min (method C)

Example XXIV

Example XXIV.1 (General Route)

(1S)-1-(1H-Indazol-4-yl)ethan-1-amine

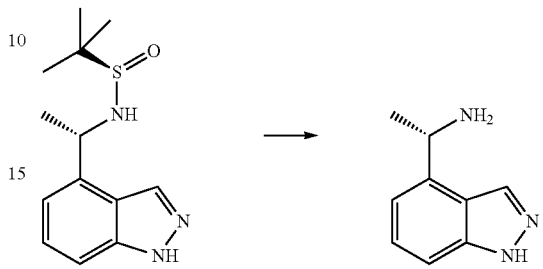

A mixture of 90.0 mg (0.34 mmol) (R)-N-[(1S)-1-(1H-indazol-4-yl)ethyl]-2-methylpropane-2-sulfinamide and 5 mL HCl in MeOH is stirred at RT overnight. The solvents are removed in vacuo to obtain the product.

$C_9H_{11}N_3$ (M=161.2 g/mol)

ESI-MS: 145 [M-NH2]$^+$

R$_t$ (HPLC): 0.38 min (method B)

Example XXV

Example XXV.1 (General Route)

(S)-2-Methyl-N-[(1E)-1-(2-methyl-2H-indazol-5-yl)ethylidene]propane-2-sulfinamide To a mixture of 70.0 mg (0.40 mmol) 1-(2-methyl-2H-indazol-5-yl)ethan-1-one (CAS: 1159511-28-0) and 2 mL THF are added 53.6 mg (0.44 mmol) (S)-2-methylpropane-2-sulfinamide and 0.39 mL (1.61 mmol) tetraethoxytitanium (85%) and the reaction mixture is stirred at 80° C. overnight. Additional 0.55 eq. (S)-2-methylpropane-2-sulfinamide are added and the mixture is stirred at 80° C. for 4 h and at RT over the weekend. The reaction mixture is poured into a diluted NaCl solution, EtOAc is added and stirred for 5 min. Then the obtained precipitate is filtered off and the layers are separated. The H$_2$O layer is extracted with EtOAc, the combined organic layers are dried over a phase separator cartridge and the solvent is removed in vacuo to obtain the product.

$C_{14}H_{19}N_3OS$ (M=277.4 g/mol)

ESI-MS: 278 [M+H]$^+$

R$_t$ (HPLC): 0.85 min (method C)

Example XXVI

Example XXVI.1 (General Route)

(1S)-1-(2-Methyl-2H-indazol-5-yl)ethan-1-amine hydrochloride

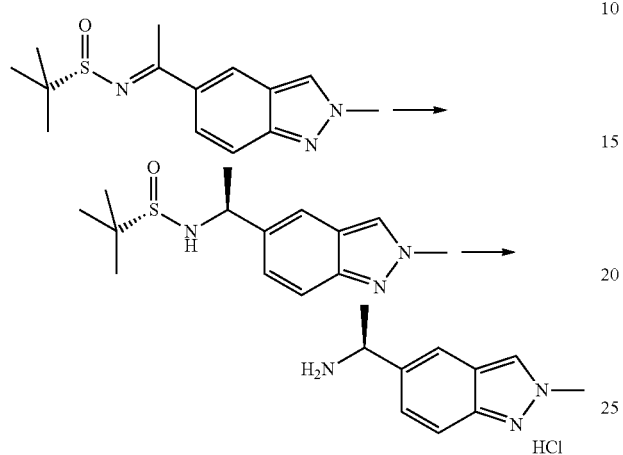

To a mixture of 0.13 g (0.45 mmol) (S)-2-methyl-N-[(1E)-1-(2-methyl-2H-indazol-5-yl)ethylidene]propane-2-sulfinamide, 5 mL THF and 0.10 mL H₂O are added 51.8 mg (1.36 mmol) sodiumborohydride at −50° C. The reaction mixture is stirred 1 h without icebath.

The mixture is diluted with sat. NH₄Cl solution and extracted 2× with EtOAc. Then the organic layer is dried over a phase separator cartridge and the solvents are removed in vacuo.

$C_{14}H_{21}N_3OS$ (M=279.4 g/mol)
ESI-MS: 280 [M+H]⁺
$R_t$ (HPLC): 0.83 min (method C)

To the above mentioned product are added 1 mL THF and 2 mL HCl (4 mol/L in dioxane) and the mixture is stirred at RT for 15 min. The solvents are removed in vacuo to obtain the product.

$C_{10}H_{13}N_3$*HCl (M=211.7 g/mol)
ESI-MS: 159 [M+H]⁺
$R_t$ (HPLC): 0.66 min (method C)

Example XXVI

Example XXVI.1 (General Route)

tert-Butyl (3S)-3-(N-methylcyclopropaneamido)pyrrolidine-1-carboxylate

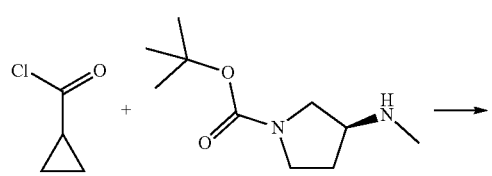

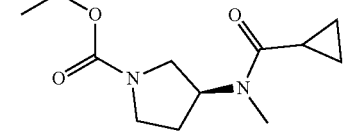

To 0.96 g (4.78 mmol) tert-butyl (3S)-3-(methylamino)pyrrolidine-1-carboxylate and 3.33 mL (23.9 mmol) TEA in 10 mL DCM are added dropwise 0.50 g (4.78 mmol) cyclopropanecarbonyl chloride dissolved in 3 mL DCM at 0° C. After stirring for 10 min at 0° C., the reaction mixture is filtered and diluted with DCM. The organic layer is washed with a mixture of sat. NaHCO₃ solution and water (1/1), washed with sat. NH₄Cl solution and with sat. NaCl solution. The organic layer is dried over Na₂SO₄, filtered and the solvent is removed in vacuo to obtain the product.

$C_{14}H_{24}N_2O_3$ (M=268.4 g/mol)
ESI-MS: 270 [M+H]⁺
$R_t$ (HPLC): 0.52 min (method A)

Example XXVII

Example XXVII.1 (General Route)

N-Methyl-N-[(3S)-pyrrolidin-3-yl]cyclopropanecarboxamide hydrochloride

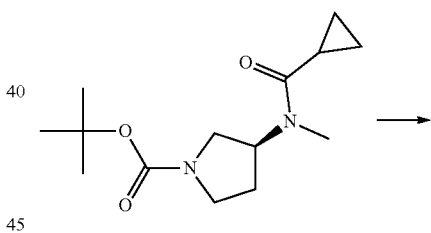

A mixture of 0.99 g (3.69 mmol) tert-butyl (3S)-3-(N-methylcyclopropaneamido)pyrrolidine-1-carboxylate and 5 mL (20.0 mmol) HCl (4 mol/L in dioxane) is stirred at RT for 1 h. The solvents are removed in vacuo to obtain the product.

$C_9H_{16}N_2O$*HCl (M=204.7 g/mol)
ESI-MS: 169 [M+H]⁺
$R_t$ (HPLC): 0.57 min (method C)

Example XXVIII

Example XXVIII.1 (General Route)

(1S)-1-{1H-Pyrrolo[2,3-b]pyridin-5-yl}ethan-1-amine hydrochloride

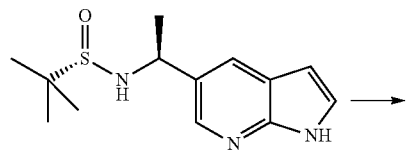

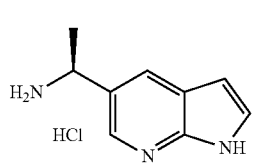

A mixture of 1.20 g (4.52 mmol) (S)-2-methyl-N-[(1S)-1-{1H-pyrrolo[2,3-b]pyridin-5-yl}ethyl]propane-2-sulfinamide, 5 mL HCl in dioxane and 10 mL THF is stirred at RT for 30 min. The obtained precipitate is filtered off and dried in vacuo to obtain the product.

$C_9H_{11}N_3$*HCl (M=197.7 g/mol)
ESI-MS: 162 [M+H]$^+$
R$_t$ (HPLC): 0.09 min (method A)

Example XXIX

Example XXIX.1 (General Route)

Methyl 6-{[(1S)-1-{1H-pyrrolo[2,3-b]pyridin-5-yl}ethyl]amino}pyridine-3-carboxylate

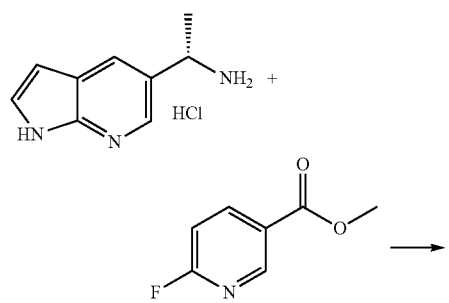

A mixture of 0.85 g (4.30 mmol) 1S)-1-{1H-pyrrolo[2,3-b]pyridin-5-yl}ethan-1-amine hydrochloride, 0.67 g (4.30 mmol) methyl 6-fluoropyridine-3-carboxylate, 3.68 (22.0 mmol) DIPEA and 5 mL DMSO is stirred at 0° C. 120° C. for 2 h.

The reaction mixture is purified by HPLC (ACN/H$_2$O/NH$_4$OH) to obtain the product.

$C_{16}H_{16}N_4O_2$ (M=296.3 g/mol)
ESI-MS: 297 [M+H]$^+$
R$_t$ (HPLC): 0.84 min (method C)

Example XXX

Example XXX.1 (General Route)

6-{[(1S)-1-{1H-Pyrrolo[2,3-b]pyridin-5-yl}ethyl]amino}pyridine-3-carboxylic acid hydrochloride

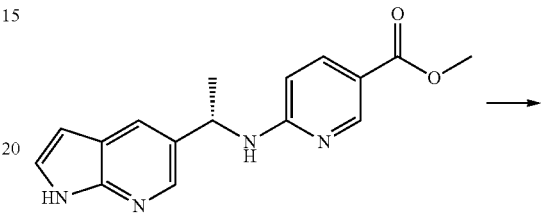

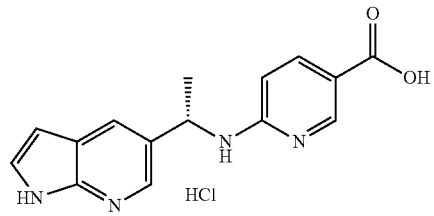

A mixture of 0.15 g (0.51 mmol) methyl 6-{[(1S)-1-{1H-pyrrolo[2,3-b]pyridin-5-yl}ethyl]amino}pyridine-3-carboxylate and 3 mL semi conc. HCl is stirred at 90° C. for 4 h. The solvent is removed in vacuo at RT to obtain the product.

$C_{15}H_{14}N_4O_2$*HCl (M=318.8 g/mol)
ESI-MS: 283 [M+H]$^+$
R$_t$ (HPLC): 0.56 min (method A)

Example XXXI

Example XXXI.1 (General Route)

5-[(3S)-3-(Methylamino)pyrrolidine-1-carbonyl]-N-[(1S)-1-{1H-pyrrolo[2,3-b]pyridin-5-yl}ethyl]pyridin-2-amine trifluoroacetic acid

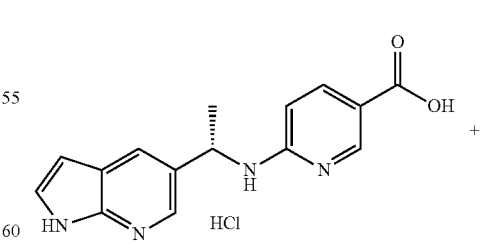

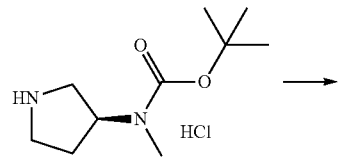

-continued

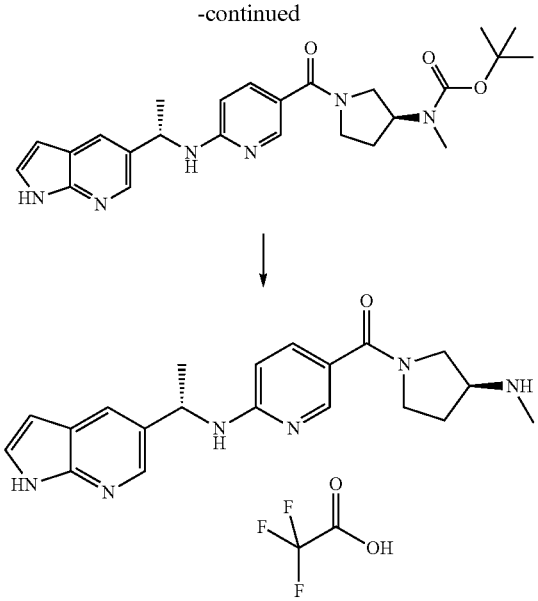

To a mixture of 0.32 g (1.00 mmol) 6-{[(1S)-1-{1H-pyrrolo[2,3-b]pyridin-5-yl}ethyl]amino}pyridine-3-carboxylic acid hydrochloride, 0.29 g (1.21 mmol) tert-butyl N-methyl-N-[(3S)-pyrrolidin-3-yl]carbamate hydrochloride, 1.72 mL (10.0 mmol) DIPEA and 3 mL DMF are added 0.46 g (1.21 mmol) HATU and the mixture is stirred a few minutes. The reaction mixture is diluted with MeOH, filtered and purified by HPLC (ACN/H$_2$O/NH$_4$OH).

$C_{25}H_{32}N_6O_3$ (M=464.6 g/mol)

ESI-MS: 465 [M+H]$^+$

R$_t$ (HPLC): 0.92 min (method C)

The above mentioned product is dissolved in 10 mL DCM and 2.5 mL TFA are added. The mixture is stirred at RT for 1 h.

$C_{20}H_{24}N_6O*C_2HF_3O_2$ (M=478.5 g/mol)

ESI-MS: 365 [M+H]$^+$

R$_t$ (HPLC): 0.73 min (method C)

The following compounds are prepared according to the general procedure (example XXXI.1) described above:

| Ex. | Starting materials | Structure | Reaction conditions | ESI-MS | HPLC Rt [min] (method) |
|---|---|---|---|---|---|
| XXXI.2 | II.1 | 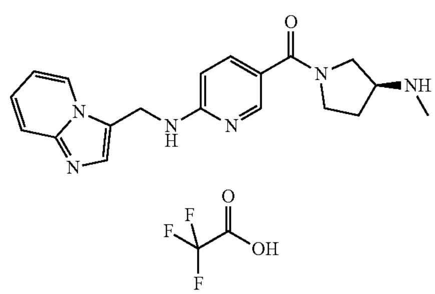 [SMILES: CN[C@H]1CCN(C(=O)c2ccc(NCc3cnc4ccccn34)nc2)C1 ; O=C(O)C(F)(F)F] | 1. RT, 10 min 2. RT, overnight, evaporation | 351 [M + H]$^+$ | 0.61 (C) |

Example XXXII

Example XXXII.1 (General Route)

tert-Butyl (3S)-3-(1-methylcyclobutaneamido)pyrrolidine-1-carboxylate

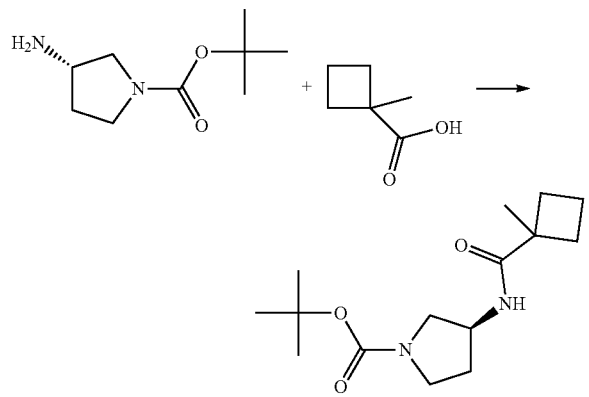

A mixture of 0.55 g (4.83 mmol) 1-methylcyclobutane-1-carboxylic acid, 2.08 mL (12.1 mmol) DIPEA, 1.94 g (6.04 mmol) and 7.5 mL DMF is stirred at RT for 30 min. Then 0.75 g (4.03 mmol) tert-butyl (3S)-3-aminopyrrolidine-1-carboxylate are added and the mixture is stirred at RT overnight.

The reaction mixture is diluted with EtOAc, washed with semi conc. NaHCO$_3$ solution, 1× with sat. NH$_4$Cl solution and 2× with semi sat. NaCl solution. The organic layer is dried over Na$_2$SO$_4$ and the solvents are removed in vacuo to obtain the crude product.

$C_{15}H_{26}N_2O_3$ (M=282.4 g/mol)
ESI-MS: 183 [M+H-BOC]$^+$
R$_t$ (HPLC): 0.92 min (method C)

Example XXXIII

Example XXXIII.1 (General Route)

N,1-Dimethyl-N-[(3S)-pyrrolidin-3-yl]cyclobutane-1-carboxamide hydrochloride

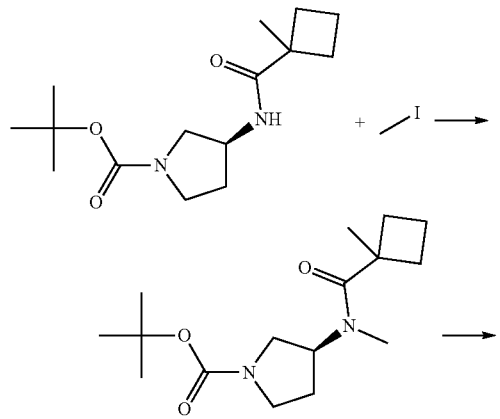

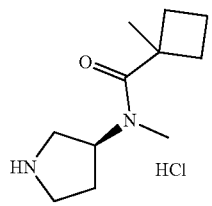

To a mixture of 1.37 g (4.85 mmol) tert-butyl (3S)-3-(1-methylcyclobutaneamido)pyrrolidine-1-carboxylate and 10 mL THF are added 0.44 mL (7.03 mmol) iodomethane and the mixture is cooled to −10° C. Then 0.33 g (8.31 mmol) sodiumhydride (60%) are added and the mixture is stirred at RT overnight. The reaction mixture is diluted with semi conc. NaHCO$_3$ solution and EtOAc and stirred vigorously. The layers are separated and the H$_2$O layer is extracted 2× with EtOAc. The combined organic layers are dried over a phase separator cartridge and the solvents are removed in vacuo. The crude product is purified by HPLC (ACN/H$_2$O/NH$_4$OH) to obtain the intermediate.

$C_{16}H_{28}N_2O_3$ (M=296.4 g/mol)
ESI-MS: 241 [M+H-tertbutyl]$^+$
R$_t$ (HPLC): 0.98 min (method A)

To the above mentioned product are added 4 mL MeOH and 4 mL HCl (4 mol/L in dioxane) and the mixture is stirred at RT over the weekend. The solvents are removed in vacuo to obtain the product.

$C_{11}H_{20}N_2O$*HCl (M=232.8 g/mol)
ESI-MS: 197 [M+H]$^+$
R$_t$ (HPLC): 0.57 min (method A)

Example XXXIV

Example XXXIV.1 (General Route)

Methyl 6-{[(1-benzothiophen-3-yl)methyl]amino}pyridine-3-carboxylate

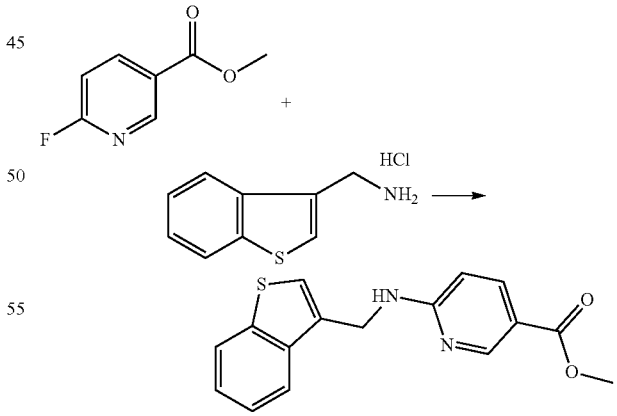

To a mixture of 0.78 g (5.00 mmol) methyl 6-fluoropyridine-3-carboxylate and 10 mL DMSO are added 2.58 mL (15.0 mmol) DIPEA and 1.00 g (5.00 mmol) 1-(1-benzothiophen-3-yl)methanamine hydrochloride and the mixture is stirred at 100° C. overnight. The reaction mixture is filtered and purified by HPLC (ACN/H$_2$O/NH$_4$OH). The fractions are combined, the organic solvent is removed in vacuo, the obtained precipitate is filtered off, washed with H₂O and dried in the air to get a white solid.

$C_{16}H_{14}N_2O_2S$ (M=298.4 g/mol)
ESI-MS: 299 [M+H]⁺
$R_t$ (HPLC): 1.00 min (method C)

Example XXXV

Example XXXV.1 (General Route)

6-{[(1-Benzothiophen-3-yl)methyl]amino}pyridine-3-carboxylic acid

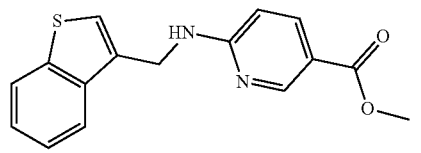

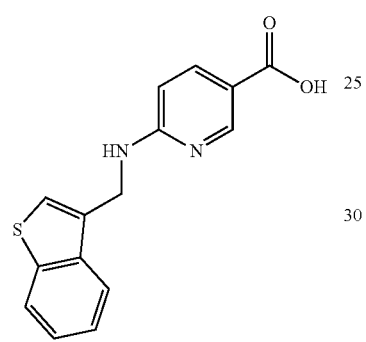

A mixture of 1.10 g (3.69 mmol) methyl 6-{[(1-benzothiophen-3-yl)methyl]amino}pyridine-3-carboxylate and 10 mL HCl (4 mol/L) is stirred at 90° C. for 1 h. A precipitate occurred and the reaction mixture is diluted with 50 mL THF and is stirred at 90° C. for 2 h. Then 10 mL conc. HCl are added and the mixture is stirred at 90° C. for 5 h. The solvents are removed in vacuo, and the residue is treated 2× with toluene which is also removed in vacuo. The remaining yellow oil is dissolved in MeOH and purified by HPLC (ACN/H₂O/HCOOH).

$C_{15}H_{12}N_2O_2S$ (M=284.3 g/mol)
ESI-MS: 285 [M+H]⁺
$R_t$ (HPLC): 0.56 min (method C)

Example XXXVI

Example XXXVI.1 (General Route)

(3S)-1-(6-Fluoropyridine-3-carbonyl)-N-methylpyrrolidin-3-amine trifluoroacetic acid

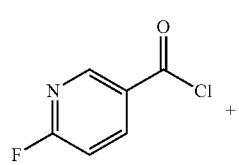
+

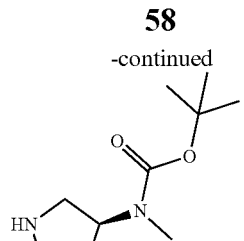

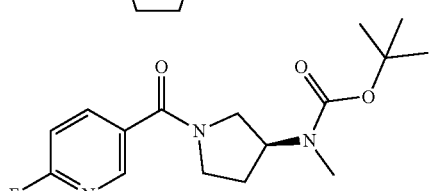

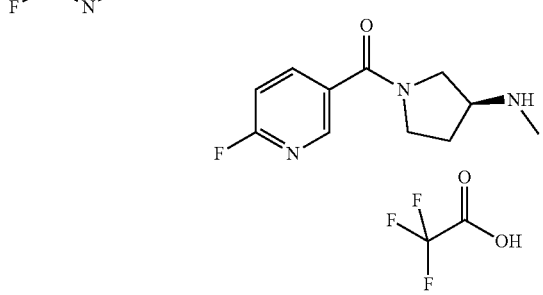

To 2.84 g (14.2 mmol) tert-butyl N-methyl-N-[(3S)-pyrrolidin-3-yl]carbamate and 9.86 mL (70.8 mmol) TEA in 40 mL DCM are added dropwise 2.26 g (14.2 mmol) 2-fluoropyridine-5-carbonyl chloride (CAS No. 65352-94-5) dissolved in 30 mL DCM at 0° C. After stirring for 10 min at 0° C., the reaction mixture is filtered and purified by column chromatography (silica gel; DCM/MeOH, 99/1-90/10).

$C_{16}H_{22}FN_3O_3$ (M=323.4 g/mol)
ESI-MS: 268 [M+H-tertbutyl]⁺
$R_t$ (HPLC): 0.89 min (method C)

To the above mentioned product are added 25 mL DCM and 5 mL TFA and the mixture is stirred at RT over the weekend. The solvents are removed in vacuo to obtain the product.

$C_{11}H_{14}FN_3O \cdot C_2HF_3O_2$ (M=337.3 g/mol)
ESI-MS: 224 [M+H]⁺
$R_t$ (HPLC): 0.61 min (method C)

Example XXXVII

Example XXXVII.1 (General Route)

N-[(3S)-1-(6-Fluoropyridine-3-carbonyl)pyrrolidin-3-yl]-N-methylcyclopropanecarboxamide

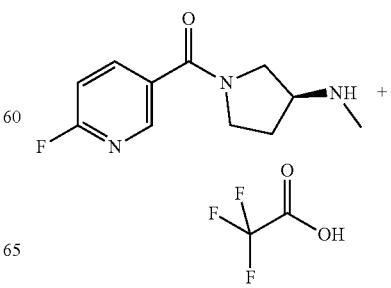

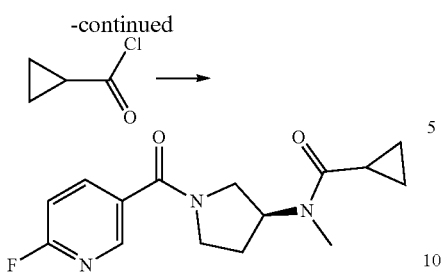

To 2.40 g (7.12 mmol) (3S)-1-(6-fluoropyridine-3-carbonyl)-N-methylpyrrolidin-3-amine trifluoroacetic acid and 4.95 mL (35.6 mmol) TEA in 40 mL DCM are added dropwise 0.82 g (7.83 mmol) cyclopropanecarbonyl chloride dissolved in 10 mL DCM at 0° C. After stirring for 10 min at 0° C., the reaction mixture is washed with a mixture of sat. NaHCO$_3$ solution and water (1/1) and with sat. NaCl solution. The organic layer is dried over Na$_2$SO$_4$, filtered and the solvent is removed in vacuo. The crude product is purified by column chromatography (DCM/MeOH 99/1-90/10) to obtain the product.

$C_{15}H_{18}FN_3O_2$ (M=291.3 g/mol)
ESI-MS: 292 [M+H]$^+$
R$_t$ (HPLC): 0.72 min (method A)

Example XXXVIII

Example XXXVIII.1 (General Route)

tert-Butyl (3S)-3-cyano-3-methylpyrrolidine-1-carboxylate tert-Butyl (3R)-3-cyano-3-methylpyrrolidine-1-carboxylate

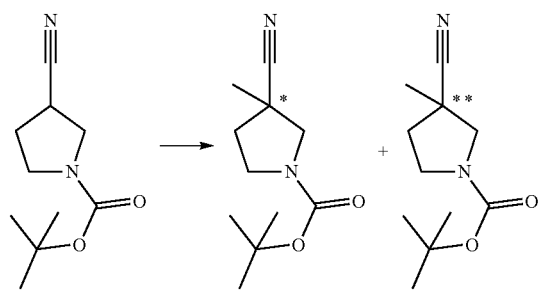

The reaction is performed under Ar atmosphere. To a mixture of 2.70 g (13.8 mmol) tert-butyl 3-cyanopyrrolidine-1-carboxylate and 40 mL THF are added 15.1 mL (15.1 mmol) LiHMDS at −78° C. After stirring 30 min at −78° C. 1.28 mL (20.6 mmol) iodomethane are added dropwise. The reaction mixture is stirred 30 min at −78° C. and 30 min at RT. The mixture is poured into 100 mL of a mixture of sat. aq. NH$_4$Cl solution and water (1:1) and extracted 2× with EtOAc. The organic layer is washed with brine, is dried over MgSO$_4$, filtered and the solvent is evaporated. The crude product is purified by chiral SFC (method G).

* or ** The absolute stereochemistry at the chiral center of the enantiomerically pure compounds was not determined.

Product A (First Eluting):
$C_{11}H_{18}N_2O_2$ (M=210.3 g/mol)
R$_t$ (HPLC): 2.58 min (method J)

Product B (second eluting):
$C_{11}H_{18}N_2O_2$ (M=210.3 g/mol)
R$_t$ (HPLC): 3.65 min (method J)

Example XXXIX

Example XXXIX.1 (General Route)

(3S)-3-methylpyrrolidine-3-carbonitrile hydrochloride

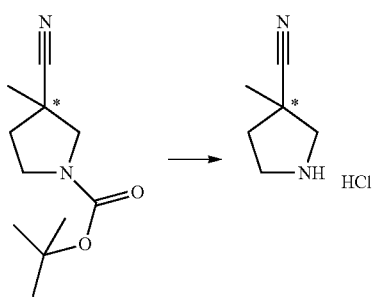

To a mixture of 1.25 g (5.95 mmol) tert-butyl 3-cyano-3-methylpyrrolidine-1-carboxylate (example XIII.1.A) in 10 mL dioxane are added 2.97 mL (11.9 mmol) HCl (4M in dioxane) and the mixture is stirred overnight at RT. The obtained precipitate is filtered off, washed with dioxane and dried in the air.

$C_6H_{10}N_2$*HCl (M=146.6 g/mol)
ESI-MS: 111 [M+H]$^+$
R$_f$ (TLC): 0.3 (SiO$_2$, DCM/MeOH/NH3 9/1/0.1)

Example XXXX

Example XXXX.1 (General Route)

6-[({Imidazo[1,5-a]pyridin-1-yl}methyl)amino]pyridine-3-carboxylic acid

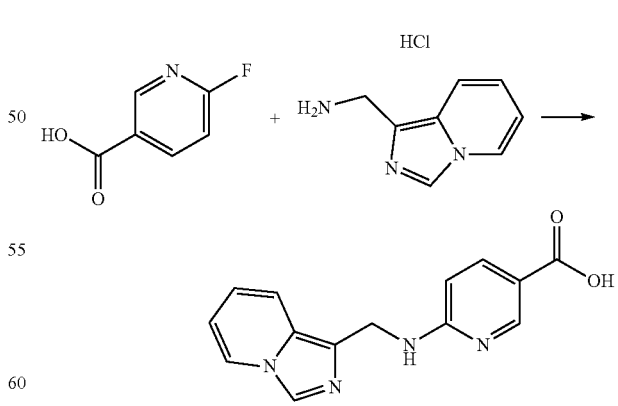

A mixture of 250 mg (1.77 mmol) 6-fluoropyridine-3-carboxylic acid, 651 mg (3.54 mmol) 1-{imidazo[1,5-a]pyridin-1-yl}methanamine hydrochloride, 980 mg (7.09 mmol) potassium carbonate and 2 mL DMSO is stirred at 150° C. overnight.

The reaction mixture is filtered and purified by HPLC (ACN/H₂O/HCOOH).
$C_{14}H_{12}N_4O_2$ (M=268.3 g/mol)
ESI-MS: 269 [M+H]⁺
$R_t$ (HPLC): 0.3 min (method H)

The following compounds are prepared according to the general procedure (example XXXX.1) described above:

| Ex. | Starting material | Structure | ESI-MS | HPLC Rt [min] (method) |
|---|---|---|---|---|
| XXXX.2 | 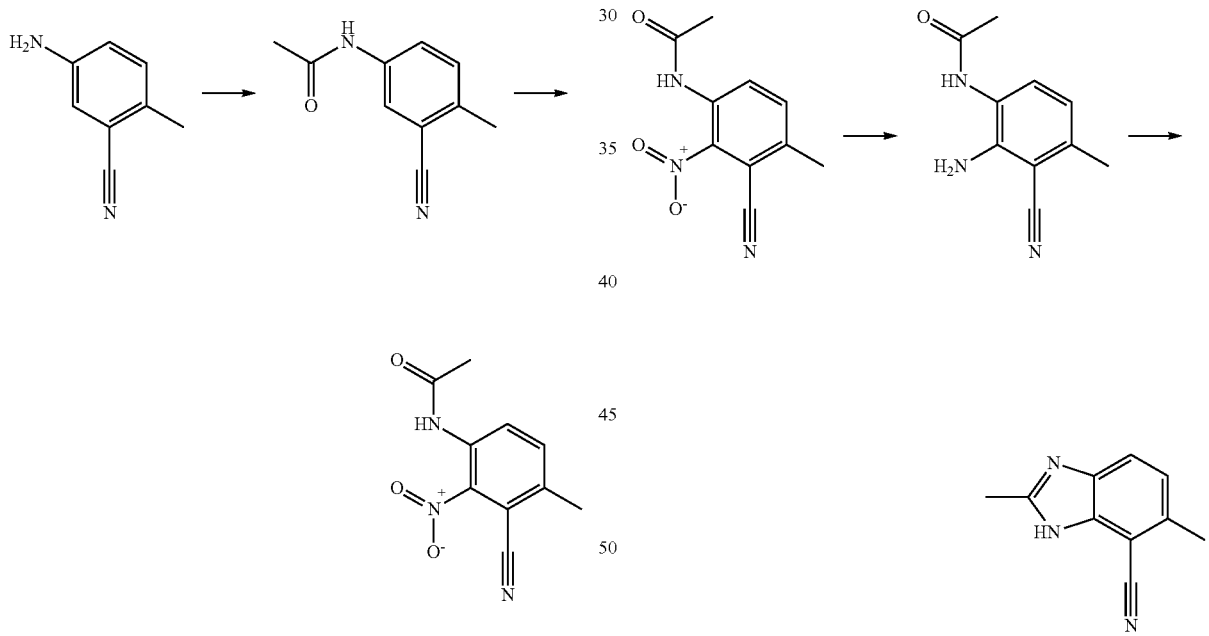 | 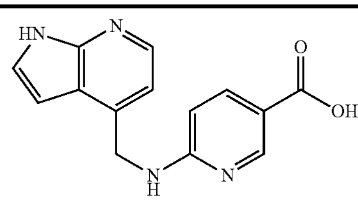 | 269 [M + H]⁺ | 0.23 (H) |

Example XXXXI

Example XXXXI.1

N-(3-Cyano-4-methyl-2-nitrophenyl)acetamide

Example XXXXII

Example XXXXII.1

2,6-Dimethyl-1H-1,3-benzodiazole-7-carbonitrile

To 65.0 g (XXX mmol) 5-amino-2-methylbenzonitrile are added 85 mL acetic anhydride (solution is formed; exothermic reaction). While cooling down the product is crystallizing. Ether is added to the reaction mixture, the precipitate is filtered off and washed with ether to obtain the wet intermediate.

85.0 g wet intermediate is added portionwise to 300 mL fuming HNO3 at −30° C. The reaction mixture is stirred for 5 min and then the reaction mixture is poured into ice water. The obtained precipitate is filtered off and washed with H2O. The solid is dried overnight in the air and then recrystallized of EtOH.

$C_{10}H_9N_3O_3$ (M=219.2 g/mol)

A mixture of 22 g (0.1 mol) N-(3-cyano-4-methyl-2-nitrophenyl)acetamide, 2 g Pd/C (10%) and 800 mL MeOH is treated with 5 bar H₂ pressure at RT for X h. The mixture is filtered and the solvent is removed in vacuo to obtain the intermediate.

18 g (0.10 mol) of the intermediate and 400 mL MeOH are heated (solution) and during 30 min at reflux HCl gas is bubbled in the reaction. After cooling down to RT the obtained white precipitate is filtered off and washed with Et₂O.

$C_{10}H_9N_3$ (M=171.2 g/mol)
Rf (TLC): 0.55 (DCM/MeOH 9/1)

Example XXXXIII

Example XXXXIII.1

1-(2,6-Dimethyl-1H-1,3-benzodiazol-7-yl)methanamine

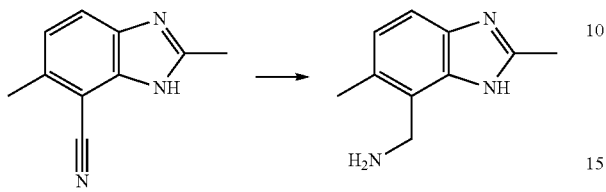

A mixture of 2.80 g (16.4 mmol) 2,6-dimethyl-1H-1,3-benzodiazole-7-carbonitrile, 1.00 g Raney nickel and 50 mL NH3 in MeOH is stirred at 50° C. and 3 bar H$_2$ pressure for X h. The reaction mixture is filtered and the solvent is removed in vacuo. The remaining crude product is triturated with Et$_2$O and the product is filtered off as a white solid.

C$_{10}$H$_{13}$N$_3$ (M=175.2 g/mol)
R$_f$ (TLC): 0.12 (DCM/MeOH/NH$_3$ 9/I/O.1)
Preparation of Final Compounds

Example 1

Example 1.1 (General Route)

3-[(3S)-1-{6-[({Imidazo[1,2-a]pyridin-3-yl}methyl)amino]pyridine-3-carbonyl}pyrrolidin-3-yl]-1,3-oxazolidin-2-one

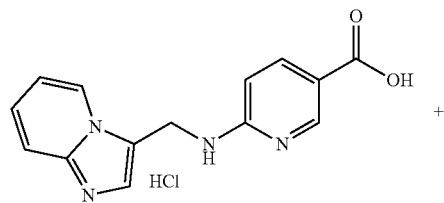

+

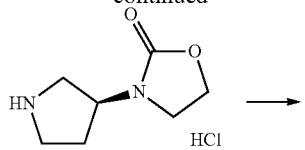

→

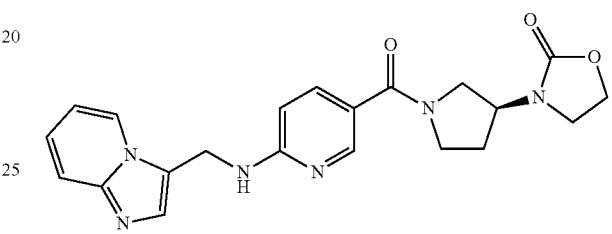

To a mixture of 50.0 mg (0.16 mmol) 6-[({imidazo[1,2-a]pyridin-3-yl}methyl)amino]pyridine-3-carboxylic acid hydrochloride (ex. 11.1) and 37.9 mg (0.20 mmol) 3-[(3S)-pyrrolidin-3-yl]-1,3-oxazolidin-2-one hydrochloride (ex. 111.1) in 2 mL DMF and 168 µL (0.98 mmol) DIPEA are added 93.6 mg (0.25 mmol) HATU and the reaction mixture is stirred at RT for 10 min.

The mixture is purified by HPLC (ACN/H$_2$O/NH$_4$OH) to obtain the product.

C$_{21}$H$_{22}$N$_6$O$_3$ (M=406.4 g/mol)
ESI-MS: 407 [M+H]$^+$
R$_t$ (HPLC): 0.67 min (method C)

The following compounds are prepared according to the general procedure (example 1.1) described above:

| Ex. | Starting materials | | Structure | Reaction conditions | ESI-MS | HPLC Rt [min] (method) |
|---|---|---|---|---|---|---|
| 1.2 | XXX.1 | XXVII.1 | 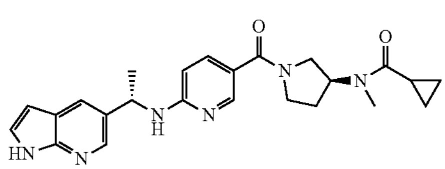 [SMILES: C[C@H](Nc1ccc(C(=O)N2CC[C@H](N(C)C(=O)C3CC3)C2)cn1)c1cnc2[nH]ccc2c1] | | 433 [M + H]$^+$ | 0.81 (C) |
| 1.3 | | XXXI.1 | 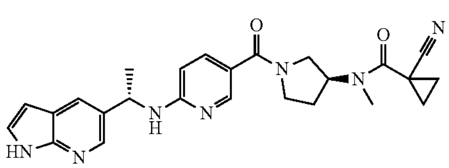 [SMILES: C[C@H](Nc1ccc(C(=O)N2CC[C@H](N(C)C(=O)C3(C#N)CC3)C2)cn1)c1cnc2[nH]ccc2c1] | | 458 [M + H]$^+$ | 0.80 (C) |

-continued
| Ex. | Starting materials | | Structure | Reaction conditions | ESI-MS | HPLC Rt [min] (method) |
|---|---|---|---|---|---|---|
| 1.4 | 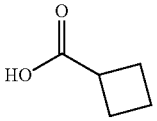 | XXXI.1 | 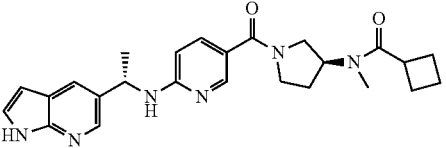 [SMILES: C[C@H](Nc1ccc(C(=O)N2CC[C@H](N(C)C(=O)C3CCC3)C2)cn1)c1cnc2[nH]ccc2c1] | | 447 [M + H]+ | 0.85 (C) |
| 1.5 | 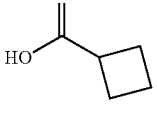 | XXXI.1 | 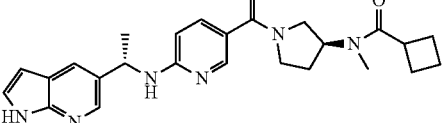 | | 447 [M + H]+ | 0.67 (A) |
| 1.6 | 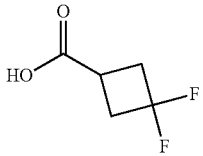 | XXXI.1 | 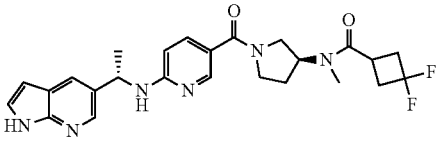 [SMILES: C[C@H](Nc1ccc(C(=O)N2CC[C@H](N(C)C(=O)C3CC(F)(F)C3)C2)cn1)c1cnc2[nH]ccc2c1] | | 483 [M + H]+ | 0.84 (C) |
| 1.7 | 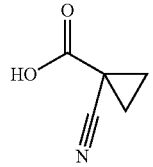 | XXXI.1 | 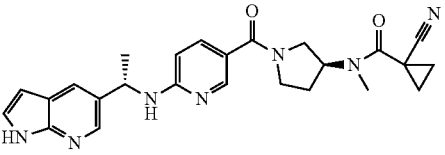 [SMILES: C[C@H](Nc1ccc(C(=O)N2CC[C@H](N(C)C(=O)C3(C#N)CC3)C2)cn1)c1cnc2[nH]ccc2c1] | | 458 [M + H]+ | 0.63 (A) |
| 1.8 | XXX.1 | XXXIII.1 | 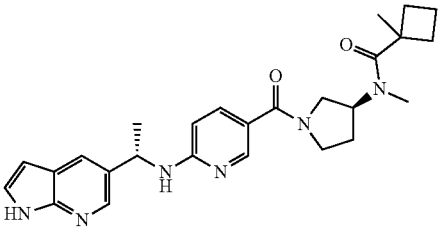 [SMILES: C[C@H](Nc1ccc(C(=O)N2CC[C@H](N(C)C(=O)C3(C)CCC3)C2)cn1)c1cnc2[nH]ccc2c1] | | 461 [M + H]+ | 0.87 (C) |
| 1.9 | 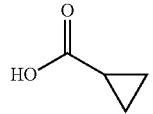 | XXXI.1 | 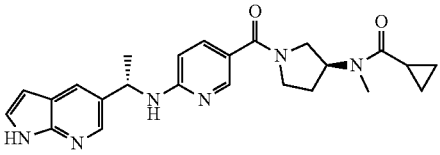 | | 365 [M + H]+ | 0.73 (C) |
| 1.10 | 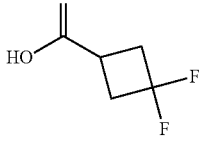 | XXXI.1 | 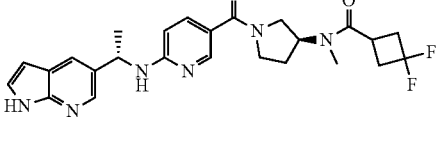 | | 483 [M + H]+ | 0.67 (A) |
| 1.11 | 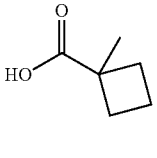 | XXXI.1 | 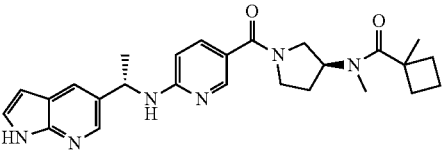 [SMILES: C[C@H](Nc1ccc(C(=O)N2CC[C@H](N(C)C(=O)C3(C)CCC3)C2)cn1)c1cnc2[nH]ccc2c1] | | 461 [M + H]+ | 0.69 (C) |

-continued

| Ex. | Starting materials | | Structure | Reaction conditions | ESI-MS | HPLC Rt [min] (method) |
|---|---|---|---|---|---|---|
| 1.12 | (3,3-difluorocyclobutanecarboxylic acid) | XXXI.2 | 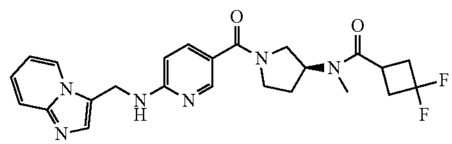 [SMILES: CN(C(=O)C1CC(F)(F)C1)[C@H]1CCN(C(=O)c2ccc(NCc3cnc4ccccn34)nc2)C1] | | 469 [M + H]⁺ | 0.54 (E) |
| 1.13 | (1-cyanocyclopropanecarboxylic acid) | XXXI.2 | 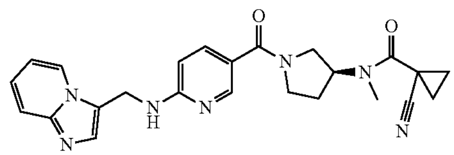 [SMILES: CN(C(=O)C1(C#N)CC1)[C@H]1CCN(C(=O)c2ccc(NCc3cnc4ccccn34)nc2)C1] | | 444 [M + H]⁺ | 0.72 (C) |
| 1.14 | (1-methylcyclobutanecarboxylic acid) | XXXI.2 | 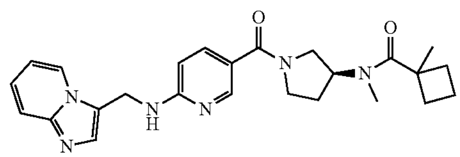 [SMILES: CN(C(=O)C1(C)CCC1)[C@H]1CCN(C(=O)c2ccc(NCc3cnc4ccccn34)nc2)C1] | | 447 [M + H]⁺ | 0.78 (C) |
| 1.15 | II.1 | III.2 | 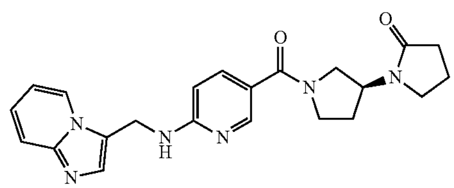 [SMILES: O=C(c1ccc(NCc2cnc3ccccn23)nc1)N1CC[C@H](N2CCCC2=O)C1] | | 405 [M + H]⁺ | 0.68 (C) |
| 1.16 | (cyclopropanecarboxylic acid) | XXXI.2 | 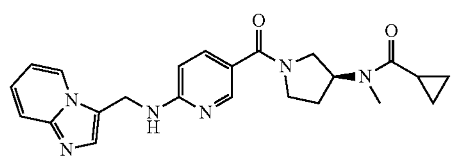 [SMILES: CN(C(=O)C1CC1)[C@H]1CCN(C(=O)c2ccc(NCc3cnc4ccccn34)nc2)C1] | | 419 [M + H]⁺ | 0.73 (C) |
| 1.17 | XXXX.1 | XXXIX.1 | 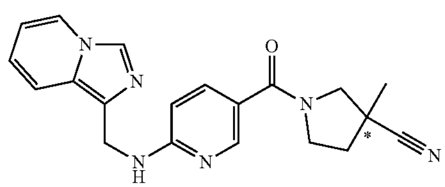 [SMILES: CC1(C#N)CCN(C(=O)c2ccc(NCc3ncn4ccccc34)nc2)C1] | RT, overnight | 361 [M + H]⁺ | 0.49 (D) |
| 1.18 | II.1 | XXXIX.1 | 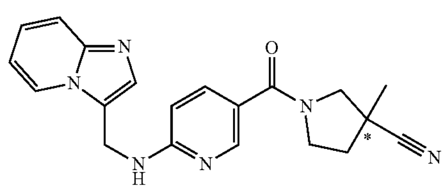 [SMILES: CC1(C#N)CCN(C(=O)c2ccc(NCc3cnc4ccccn34)nc2)C1] | RT, overnight | 361 [M + H]⁺ | 0.46 (D) |
| 1.19 | XXXX.2 | XXXIX.1 | 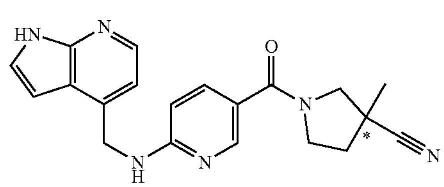 [SMILES: CC1(C#N)CCN(C(=O)c2ccc(NCc3ccnc4[nH]ccc34)nc2)C1] | RT, overnight | 361 [M + H]⁺ | 0.47 (D) |

*The stereochemistry at the chiral center of the enantiomerically and diastereomerically pure compound was not determined.

Example 2

Example 2.1 (General Route)

N-[1(3S)-1-(6-{1[(5-Chloro-1H-indazol-3-yl)methyl]amino}pyridine-3-carbonyl)pyrrolidin-3-yl]-N-methylacetamide

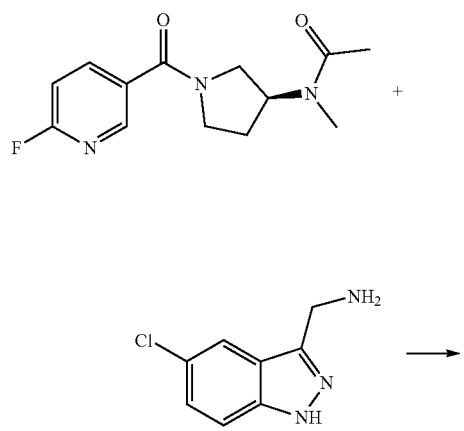

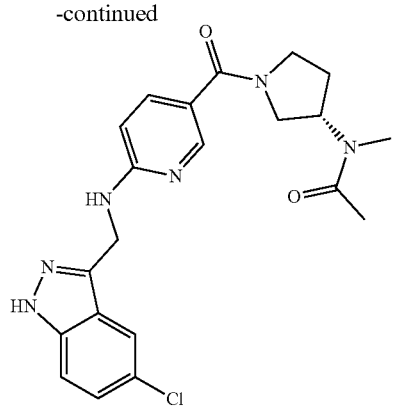

To a mixture of 26.5 mg (0.10 mmol) N-[(3S)-1-(6-fluoropyridine-3-carbonyl)pyrrolidin-3-yl]-N-methylacetamide in 1 mL DMSO are added 51.6 μL (0.30 mmol) DIPEA and 21.8 mg (0.12 mmol) (5-chloro-1H-indazol-3-yl)methanamine and the reaction mixture is stirred overnight at 100° C. The mixture is filtered and purified by HPLC (ACN/H$_2$O/TFA) to obtain the product.

$C_{21}H_{23}ClN_6O_2$ (M=426.9 g/mol)

ESI-MS: 427 [M+H]$^+$

R$_t$ (HPLC): 0.44 min (method G)

The following compounds are prepared according to the general procedure (example 2.1) described above:

| Ex. | Starting materials | Structure | Reaction conditions | ESI-MS | HPLC Rt [min] (method) |
|---|---|---|---|---|---|
| 2.2 | IV.1 | 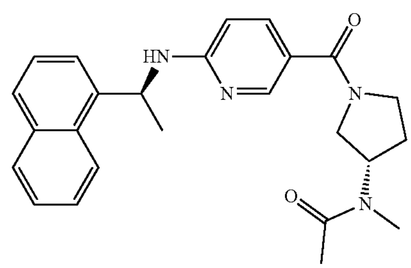 [SMILES: CC(=O)N(C)[C@H]1CCN(C(=O)c2ccc(N[C@@H](C)c3cccc4ccccc34)nc2)C1] | | 417 [M + H]$^+$ | 0.54 (F) |
| 2.3 | IV.1 | 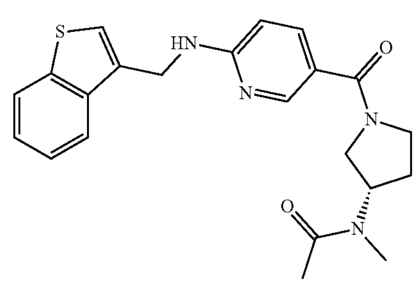 [SMILES: CC(=O)N(C)[C@H]1CCN(C(=O)c2ccc(NCc3csc4ccccc34)nc2)C1] | 100° C., 1.5 d | 443 [M + H]$^+$ | 0.56 (F) |

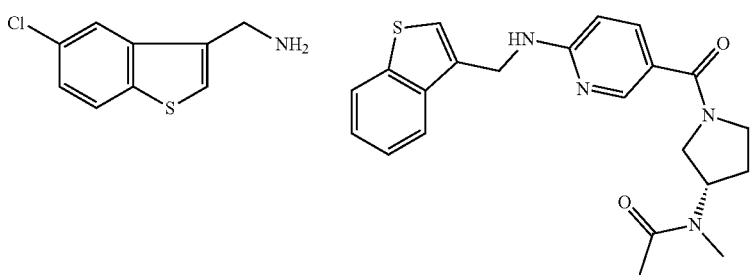

-continued

| Ex. | Starting materials | Structure | Reaction conditions | ESI-MS | HPLC Rt [min] (method) |
|---|---|---|---|---|---|
| 2.4 | IV.1 | 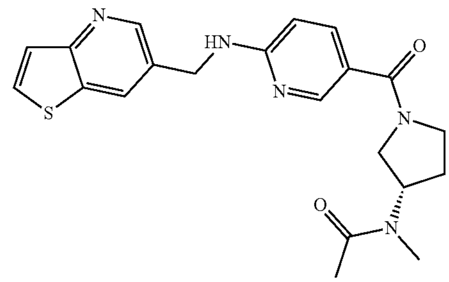 [SMILES: CC(=O)N(C)[C@H]1CCN(C(=O)c2ccc(NCc3cnc4ccsc4c3)nc2)C1] | 120° C. overnight | 410 [M + H]⁺ | 0.60 (B) |
| 2.5 | IV.1 | 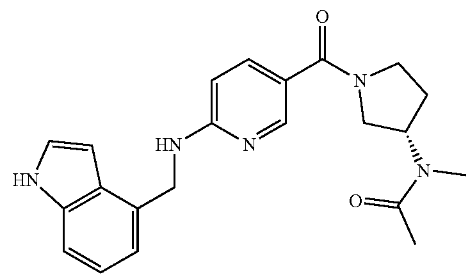 | | 406 [M + H]⁺ | 0.44 (G) |
| 2.6 | IV.1 | 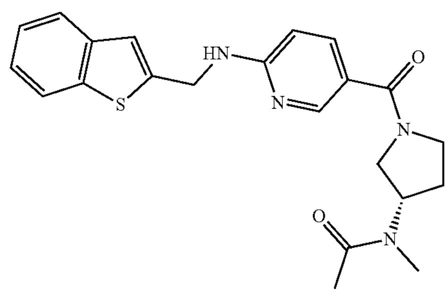 [SMILES: CC(=O)N(C)[C@H]1CCN(C(=O)c2ccc(NCc3cc4ccccc4s3)nc2)C1] | 120° C. overnight | 409 [M + H]⁺ | 0.50 (F) |

Example 3

Example 3.1 (General Route)

N-[(3S)-1-(6-{1[(1-Benzothiophen-3-yl)methyl]amino}pyridine-3-carbonyl)pyrrolidin-3-yl]-N-methylacetamide

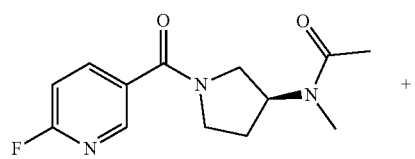

+

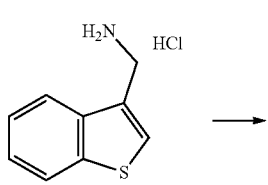

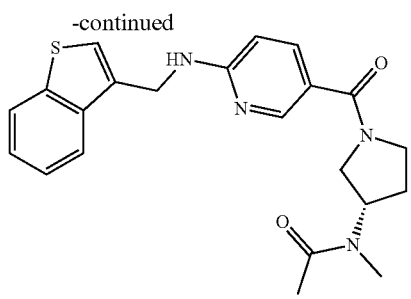

To a mixture of 250 mg (0.94 mmol) N-[(3S)-1-(6-fluoropyridine-3-carbonyl)pyrrolidin-3-yl]-N-methylacetamide in 10 mL DMSO are added 486 L (0.28 mmol) DIPEA and 226 mg (0.11 mmol) 1-(1-benzothiophen-3-yl)methanamine hydrochloride and the reaction mixture is stirred overnight at 100° C. The mixture is filtered and purified by HPLC (ACN/H₂O/NH₄OH). After freezedrying the product is repurified by column chromatography (silica gel; DCM/MeOH, 7/3). The solvents are removed in vacuo and the remaining product is dissolved in dioxane and freezedried.

$C_{22}H_{24}N_4O_2S$ (M=408.5 g/mol)
ESI-MS: 409 [M+H]⁺
$R_t$ (HPLC): 0.86 min (method C)

Example 4

Example 4.1 (General Route)

N-[(3S)-1-{6-[({Imidazo[1,2-a]pyridin-3-yl}methyl)amino]pyridine-3-carbonyl}pyrrolidin-3-yl]-N-methylcyclobutanecarboxamide

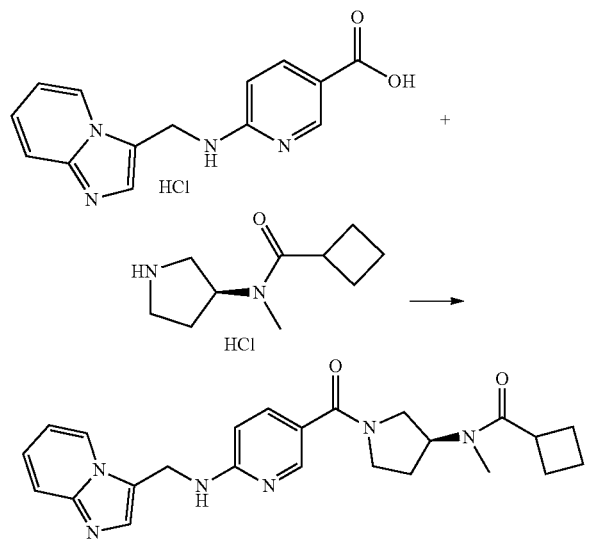

To a mixture of 0.15 g (0.49 mmol) 6-[({imidazo[1,2-a]pyridin-3-yl}methyl)amino]pyridine-3-carboxylic acid hydrochloride, 0.16 g (0.74 mmol) N-methyl-N-[(3S)-pyrrolidin-3-yl]cyclobutanecarboxamide hydrochloride, 0.84 mL (0.49 mmol) DIPEA in 3 mL DMF are added 0.28 g (0.74 mmol) HATU and the reaction mixture is stirred at RT for a 5 minutes. The mixture is purified by HPLC (ACN/H$_2$O/NH$_4$OH). The organic solvent is removed in vacuo and the remaining solution is diluted with sat. NaHCO$_3$ solution and is extracted 2× with DCM. The organic layer is dried over a phase separator cartridge and the solvent is removed in vacuo. The remaining solid is purified by column chromatography (silica gel; DCM/MeOH, 98/2-80/20). The solvents are removed in vacuo to obtain the product.

C$_{24}$H$_{28}$N$_6$O$_2$ (M=432.5 g/mol)
ESI-MS: 433 [M+H]$^+$
R$_t$ (HPLC): 0.78 min (method C)

Example 5

Example 5.1 (General Route)

N-Methyl-N-[(3S)-1-{6-[({thieno[3,2-c]pyridin-7-yl}methyl)amino]pyridine-3-carbonyl}pyrrolidin-3-yl]acetamide

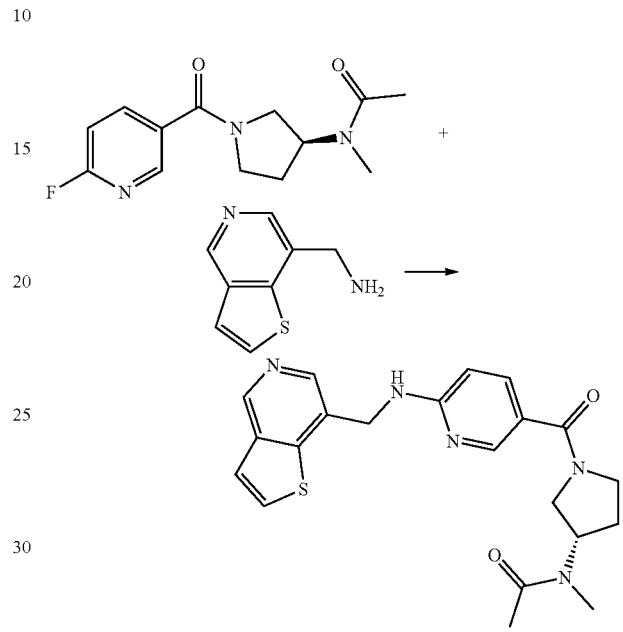

To a mixture of 30.0 mg (0.11 mmol) N-[(3S)-1-(6-fluoropyridine-3-carbonyl)pyrrolidin-3-yl]-N-methylacetamide in 1 mL DMSO are added 58.3 µL (0.34 mmol) DIPEA and 20.4 mg (0.12 mmol) 1-{thieno[3,2-c]pyridin-7-yl}methanamine and the reaction mixture is stirred overnight at 120° C. The mixture is filtered and purified by HPLC (ACN/H$_2$O/NH$_4$HH) to obtain the product.

C$_{21}$H$_{23}$N$_5$O$_2$S (M=409.5 g/mol)
ES-MS: 410 [M+H]$^+$
R$_t$ (HPLC): 0.45 min (method D)

The following compounds are prepared according to the general procedure (example 5.1) described above:

| Ex. | Starting materials | | Structure | Reaction conditions | ESI-MS | HPLC Rt [min] (method) |
|---|---|---|---|---|---|---|
| 5.2 | IV.1 | IX.1 | ![structure] | | 421 [M + H]$^+$ | 0.79 (C) |
| 5.3 | IV.1 | ![structure with NH$_2$] | ![structure] | | 393 [M + H]$^+$ | 0.71 (C) |

-continued

| Ex. | Starting materials | Structure | Reaction conditions | ESI-MS | HPLC Rt [min] (method) |
|---|---|---|---|---|---|
| 5.4 | IV.1 | 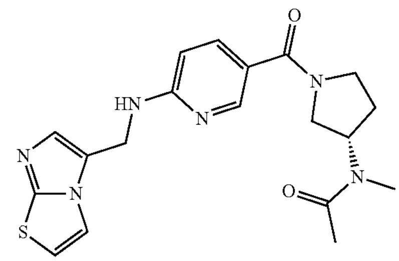 [SMILES: CC(=O)N(C)[C@H]1CCN(C(=O)c2ccc(NCc3cnc4sccn34)nc2)C1] | 100° C., overnight, 24 h 100° C. | 433 [M + H]+ | 0.47 (D) |
| 5.5 | IV.1 | 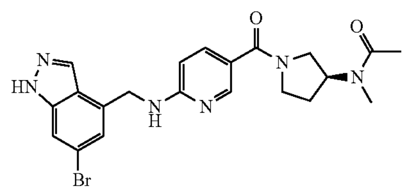 [SMILES: CC(=O)N(C)[C@H]1CCN(C(=O)c2ccc(NCc3cc(Br)cc4[nH]ncc34)nc2)C1] | 110° C. overnight | 471 [M + H]+ | 0.52 (D) |
| 5.6 | IV.1 | 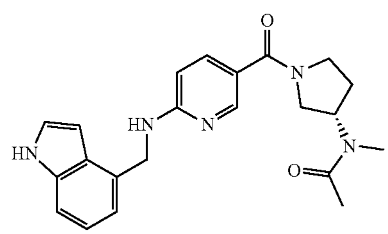 [SMILES: CC(=O)N(C)[C@H]1CCN(C(=O)c2ccc(NCc3cccc4[nH]ccc34)nc2)C1] | 100° C., overnight | 392 [M + H]+ | 0.48 (E) |
| 5.7 | IV.1 | 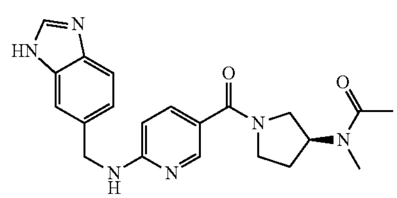 [SMILES: CC(=O)N(C)[C@H]1CCN(C(=O)c2ccc(NCc3ccc4nc[nH]c4c3)nc2)C1] | | 393 [M + H]+ | 0.67 (C) |
| 5.8 | IV.1 X.1 | 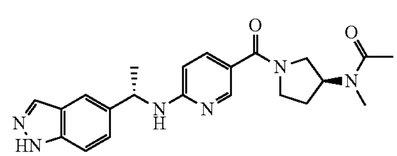 [SMILES: CC(=O)N(C)[C@H]1CCN(C(=O)c2ccc(N[C@@H](C)c3ccc4[nH]ncc4c3)nc2)C1] | 100° C. 100° C., overnight | 407 [M + H]+ | 0.74 (C) |
| 5.9 | IV.1 | 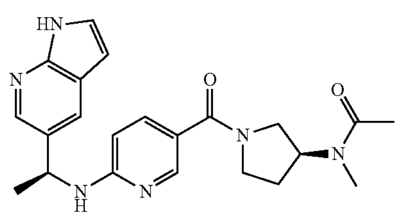 [SMILES: CC(=O)N(C)[C@H]1CCN(C(=O)c2ccc(N[C@@H](C)c3cnc4[nH]ccc4c3)nc2)C1] | 120° C., 4 h | 407 [M + H]+ | 0.65 (H) |
| 5.10 | IV.1 | 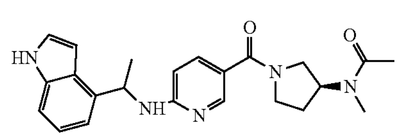 [SMILES: CC(=O)N(C)[C@H]1CCN(C(=O)c2ccc(NC(C)c3cccc4[nH]ccc34)nc2)C1] | | 406 [M + H]+ | 0.79 (C) |

-continued

| Ex. | Starting materials | | Structure | Reaction conditions | ESI-MS | HPLC Rt [min] (method) |
|---|---|---|---|---|---|---|
| 5.11 | IV.1 | quinolin-3-ylmethanamine | 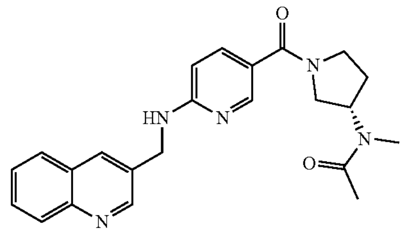 [SMILES: CC(=O)N(C)[C@H]1CCN(C(=O)c2ccc(NCc3cnc4ccccc4c3)nc2)C1] | 100° C., overnight | 404 [M + H]⁺ | 0.48 (E) |
| 5.12 | IV.1 | imidazo[1,2-a]pyridin-3-ylmethanamine · 2HCl | 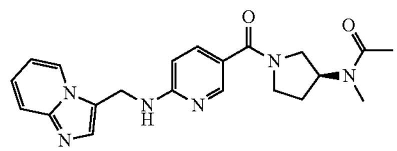 [SMILES: CC(=O)N(C)[C@H]1CCN(C(=O)c2ccc(NCc3cnc4ccccn34)nc2)C1] | | 393 [M + H]⁺ | 0.69 (C) |
| 5.13 | IV.1 | (1H-pyrrolo[2,3-b]pyridin-4-yl)methanamine · HCl | 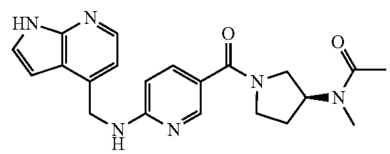 [SMILES: CC(=O)N(C)[C@H]1CCN(C(=O)c2ccc(NCc3ccnc4[nH]ccc34)nc2)C1] | 120° C., 4 h 120° C., overnight | 393 [M + H]⁺ | 0.56 (H) |
| 5.14 | IV.1 | (1H-indazol-3-yl)methanamine | 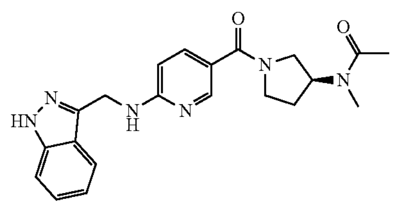 [SMILES: CC(=O)N(C)[C@H]1CCN(C(=O)c2ccc(NCc3n[nH]c4ccccc34)nc2)C1] | 120° C. overnight, additional 0.75 eq. amine, 120° C. overnight | 393 [M + H]⁺ | 0.75 (C) |
| 5.15 | IV.1 | XIII.1 | 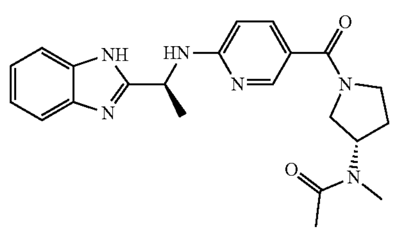 [SMILES: CC(=O)N(C)[C@H]1CCN(C(=O)c2ccc(N[C@@H](C)c3nc4ccccc4[nH]3)nc2)C1] | 100° C., 2 d | 441 [M + H]⁺ | 0.54 (D) |
| 5.16 | IV.1 | (1H-indol-3-yl)methanamine | 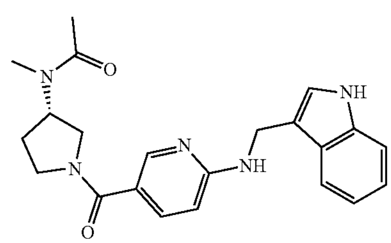 [SMILES: CC(=O)N(C)[C@H]1CCN(C(=O)c2ccc(NCc3c[nH]c4ccccc34)nc2)C1] | 100° C., overnight | 392 [M + H]⁺ | 0.53 (D) |
| 5.17 | IV.1 | (1H-indol-5-yl)methanamine | 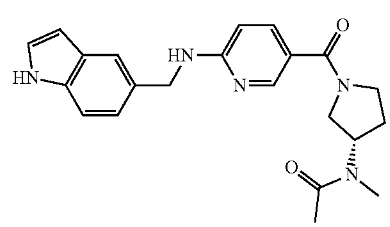 [SMILES: CC(=O)N(C)[C@H]1CCN(C(=O)c2ccc(NCc3ccc4[nH]ccc4c3)nc2)C1] | 100° C., overnight | 392 [M + H]⁺ | 0.51 (D) |

-continued

| Ex. | Starting materials | | Structure | Reaction conditions | ESI-MS | HPLC Rt [min] (method) |
|---|---|---|---|---|---|---|
| 5.18 | IV.1 | HCl, HCl (H₂N-CH₂-benzimidazole-2-amine) | 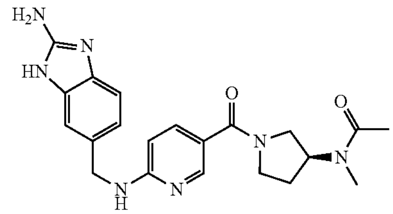 [SMILES: CC(=O)N(C)[C@H]1CCN(C(=O)c2ccc(NCc3ccc4nc(N)[nH]c4c3)nc2)C1] | | 408 [M + H]⁺ | 0.66 (C) |
| 5.19 | IV.1 | HCl (imidazopyridine-CH₂-NH₂) | 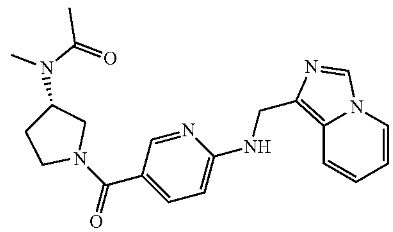 [SMILES: CC(=O)N(C)[C@H]1CCN(C(=O)c2ccc(NCc3ncn4ccccc34)nc2)C1] | double purification by HPLC | 393 [M + H]⁺ | 0.43 (D) |
| 5.20 | IV.1 | XV.1 | 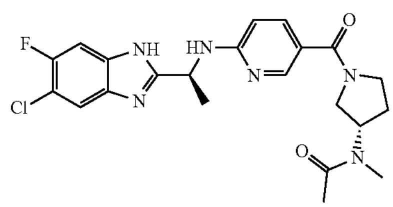 [SMILES: CC(=O)N(C)[C@H]1CCN(C(=O)c2ccc(N[C@@H](C)c3nc4cc(Cl)c(F)cc4[nH]3)nc2)C1] | 100° C., 2 d | 459 [M + H]⁺ | 0.56 (D) |
| 5.21 | IV.1 | (tetrahydrobenzisoxazole-CH₂-NH₂) | 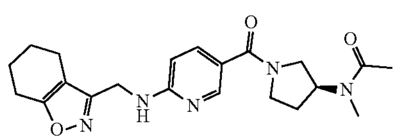 [SMILES: CC(=O)N(C)[C@H]1CCN(C(=O)c2ccc(NCc3noc4c3CCCC4)nc2)C1] | 120° C., 5 h | 398 [M + H]⁺ | 0.79 (C) |
| 5.22 | IV.1 | (indazole-CH₂-NH₂) | 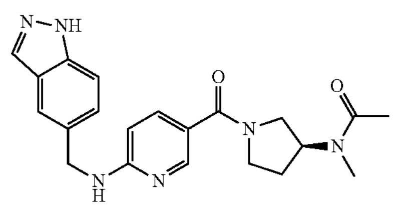 [SMILES: CC(=O)N(C)[C@H]1CCN(C(=O)c2ccc(NCc3ccc4[nH]ncc4c3)nc2)C1] | double purification by HPLC | 393 [M + H]⁺ | 0.71 (C) |
| 5.23 | IV.1 | (1-(benzimidazol-2-yl)ethylamine) | 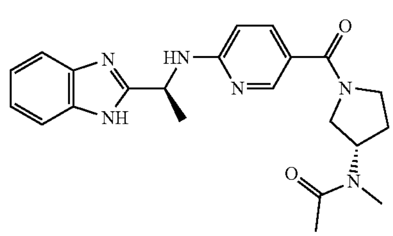 [SMILES: CC(=O)N(C)[C@H]1CCN(C(=O)c2ccc(N[C@@H](C)c3nc4ccccc4[nH]3)nc2)C1] | 100° C., 2 d | 407 [M + H]⁺ | 0.45 (D) |
| 5.24 | IV.1 | (quinoline-5-CH₂-NH₂) | 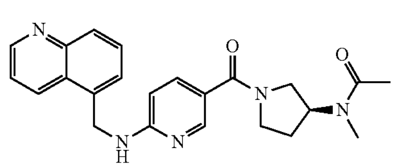 [SMILES: CC(=O)N(C)[C@H]1CCN(C(=O)c2ccc(NCc3cccc4ncccc34)nc2)C1] | | 404 [M + H]⁺ | 0.55 (A) |

-continued

| Ex. | Starting materials | | Structure | Reaction conditions | ESI-MS | HPLC Rt [min] (method) |
|---|---|---|---|---|---|---|
| 5.25 | IV.1 | IX.2 | 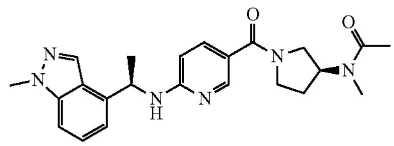 [SMILES: CC(=O)N(C)[C@H]1CCN(C(=O)c2ccc(N[C@H](C)c3cccc4c3cnn4C)nc2)C1] | | 421 [M + H]+ | 0.79 (C) |
| 5.26 | IV.1 | HCl, quinolin-6-ylmethanamine·HCl | 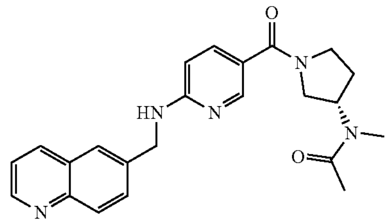 [SMILES: CC(=O)N(C)[C@H]1CCN(C(=O)c2ccc(NCc3ccc4ncccc4c3)nc2)C1] | 100° C., 2 d | 404 [M + H]+ | 0.46 (D) |
| 5.27 | IV.1 | IX.3 | 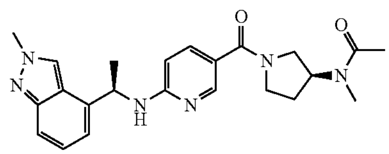 [SMILES: CC(=O)N(C)[C@H]1CCN(C(=O)c2ccc(N[C@H](C)c3cccc4nn(C)cc34)nc2)C1] | 120° C., weekend | 421 [M + H]+ | 0.75 (C) |
| 5.28 | IV.1 | 4,5,6,7-tetrahydro-1H-indazol-3-ylmethanamine | 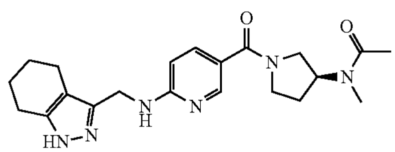 [SMILES: CC(=O)N(C)[C@H]1CCN(C(=O)c2ccc(NCc3n[nH]c4c3CCCC4)nc2)C1] | 100° C., weekend | 397 [M + H]+ | 0.76 (C) |
| 5.29 | IV.1 | pyrazolo[1,5-a]pyrimidin-3-ylmethanamine·HCl | 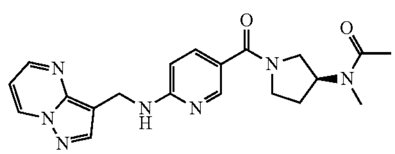 [SMILES: CC(=O)N(C)[C@H]1CCN(C(=O)c2ccc(NCc3cnn4cccnc34)nc2)C1] | | 394 [M + H]+ | 0.67 (C) |
| 5.30 | IV.1 | quinolin-8-ylmethanamine·HCl | 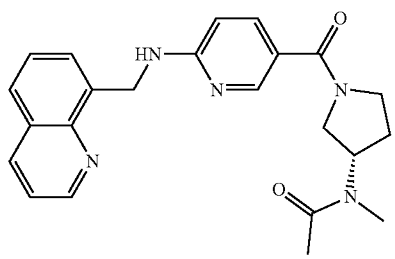 [SMILES: CC(=O)N(C)[C@H]1CCN(C(=O)c2ccc(NCc3cccc4cccnc34)nc2)C1] | 100° C., 2 d | 404 [M + H]+ | 0.54 (D) |
| 5.31 | IV.1 | benzo[d]thiazol-2-ylmethanamine | 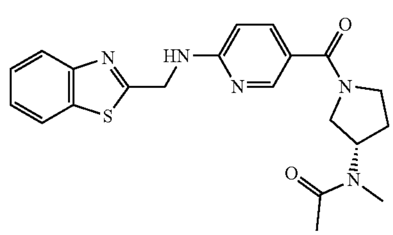 [SMILES: CC(=O)N(C)[C@H]1CCN(C(=O)c2ccc(NCc3nc4ccccc4s3)nc2)C1] | double purification by HPLC | 410 [M + H]+ | 0.54 (E) |
| 5.32 | IV.1 | 1-(1-methyl-1H-indazol-5-yl)ethanamine·HCl | 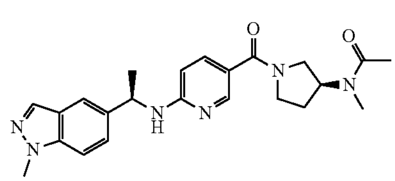 [SMILES: CC(=O)N(C)[C@H]1CCN(C(=O)c2ccc(N[C@H](C)c3ccc4c(cnn4C)c3)nc2)C1] | double purification by HPLC | 421 [M + H]+ | 0.78 (C) |

-continued
| Ex. | Starting materials | | Structure | Reaction conditions | ESI-MS | HPLC Rt [min] (method) |
|---|---|---|---|---|---|---|
| 5.33 | IV.1 |  | 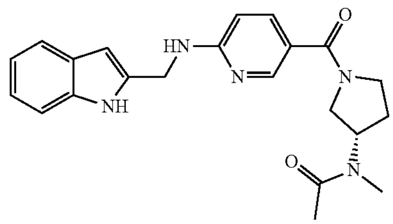 [SMILES: CC(=O)N(C)[C@H]1CCN(C(=O)c2ccc(NCc3cc4ccccc4[nH]3)nc2)C1] | 100° C., overnight | 392 [M + H]+ | 0.59 (D) |
| 5.34 | IV.1 | 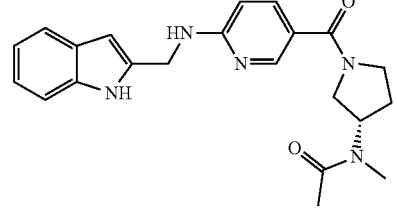 | 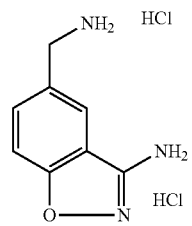 [SMILES: Cl ; NCc1ccc2onc(N)c2c1 ; Cl] | 100° C., 2 d | 409 [M + H]+ | 0.42 (D) |
| 5.35 | IV.1 | 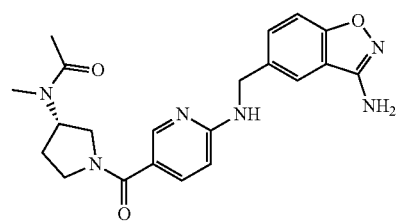 | 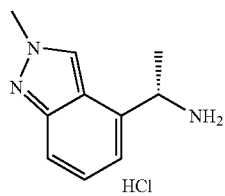 | | 412 [M + H]+ | 0.75 (C) |
| 5.36 | IV.1 | XXI.1 | 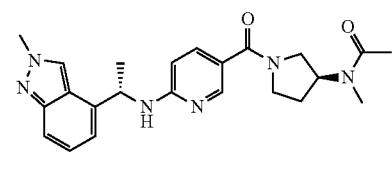 | 120° C. 4 h, +3 eq. DIPEA, 120° C. overnight, +1 eq. amine, 120° C. overnight | 407 [M + H]+ | 0.69 (C) |
| 5.37 | IV.1 | IX.6 | 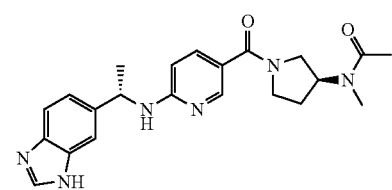 | | 421 [M + H]+ | 0.78 (C) |
| 5.38 | IV.1 | XXVI.1 | 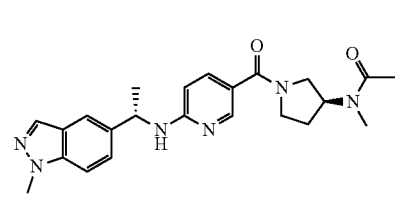 [SMILES: CC(=O)N(C)[C@H]1CCN(C(=O)c2ccc(N[C@@H](C)c3ccc4c(cnn4C)c3)nc2)C1] | 100° C. overnight, additional 1.4 eq. amine 100° C. overnight | 421 [M + H]+ | 0.75 (C) |
| 5.39 | XXXVII.1 | 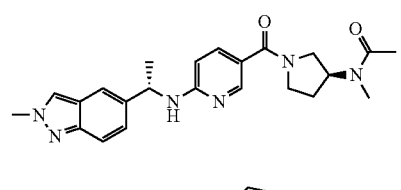 | 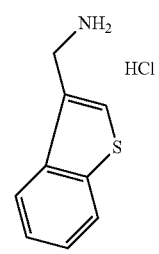 [SMILES: NCc1csc2ccccc12 ; Cl] | | 435 [M + H]+ | 0.92 (C) |

| Ex. | Starting materials | Structure | Reaction conditions | ESI-MS | HPLC Rt [min] (method) |
|---|---|---|---|---|---|
| 5.40 | IV.1 XXXXIII.1 | 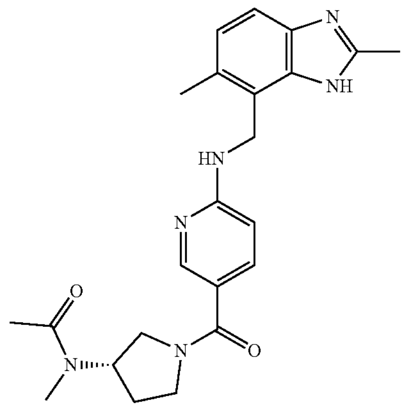 [SMILES: CC(=O)N(C)[C@H]1CCN(C(=O)c2ccc(NCc3c(C)ccc4nc(C)[nH]c34)nc2)C1] | 100° C., overnight | 421 [M + H]+ | 0.47 (D) |

Example 6

Example 6.1 (General Route)

N-Methyl-N-[(3S)-1-(6-{[(6-methyl-1H-indazol-4-yl)methyl]amino}pyridine-3-carbonyl)pyrrolidin-3-yl]acetamide

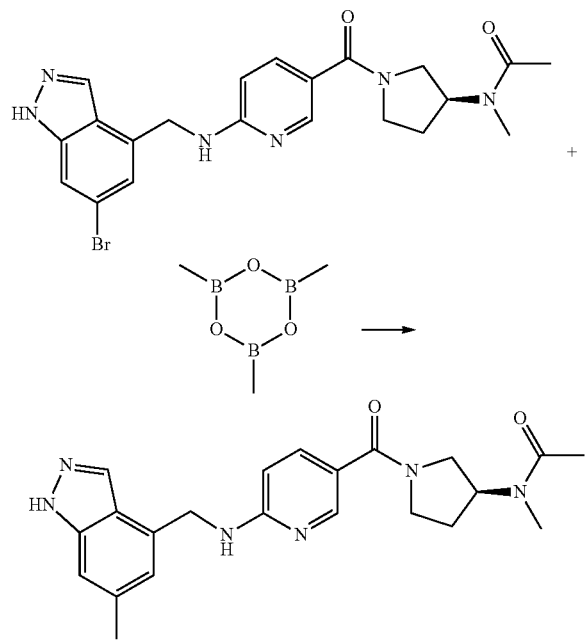

The reaction is performed under Ar atmosphere.

A mixture of 50.0 mg (0.11 mmol) N-[(3S)-1-(6-{[(6-bromo-1H-indazol-4-yl)methyl]amino}pyridine-3-carbonyl)pyrrolidin-3-yl]-N-methylacetamide, 22.1 µL (0.16 mmol) trimethyl-1,3,5,2,4,6-trioxatriborinane, 0.11 mL Na$_2$CO$_3$ solution (2 mol/L) and 5 mL dioxane is degassed and purged with argon. Then 4.33 mg (0.01 mmol) Pd(dppf)Cl$_2$ is added and the reaction mixture is stirred at 100° C. for 2 h.

The solvents are removed in vacuo, the crude product is dissolved in EtOAc and filtered. The filtrate is washed with sat. NaCl solution, dried over Na$_2$SO$_4$ and the solvent is removed in vacuo. The crude product is dissolved in DMF and purified by HPLC (ACN/H$_2$O/NH$_4$OH) to obtain the product.

C$_{22}$H$_{26}$N$_6$O$_2$ (M=406.5 g/mol)
ESI-MS: 407 [M+H]+
R$_t$ (HPLC): 0.48 min (method D)

Example 7

Example 7.1 (General Route)

N-[(3S)-1-(6-{[(1S)-1-(1H-Indazol-4-yl)ethyl]amino}pyridine-3-carbonyl)pyrrolidin-3-yl]-N-methylacetamide

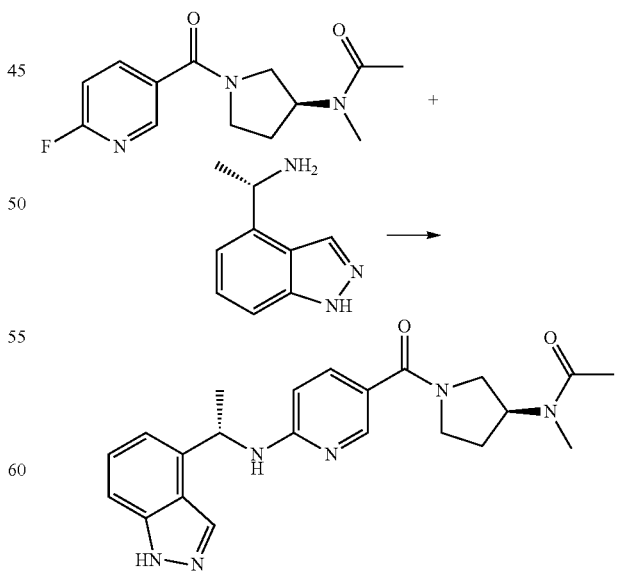

A mixture of 50.0 mg (0.19 mmol) N-[(3S)-1-(6-fluoropyridine-3-carbonyl)pyrrolidin-3-yl]-N-methylacetamide, 33.4 mg (0.21 mmol) (1S)-1-(1H-indazol-4-yl)ethan-1-amine, 113 μL (1.00 mmol) DIPEA and 2 mL NMP is stirred at 110° C. for 15 h in a closed vial. The reaction mixture is filtered and purified 2× by HPLC (ACN/H$_2$O/NH$_4$OH) to obtain the product.

C$_{22}$H$_{26}$N$_6$O$_2$ (M=406.5 g/mol)
ESI-MS: 407 [M+H]$^+$
R$_t$ (HPLC): 0.47 min (method E)

Example 8

Example 8.1 (General Route)

3-[(3S)-1-(6-{[(1-Benzothiophen-3-yl)methyl]amino}pyridine-3-carbonyl)pyrrolidin-3-yl]-13-oxazolidin-2-one

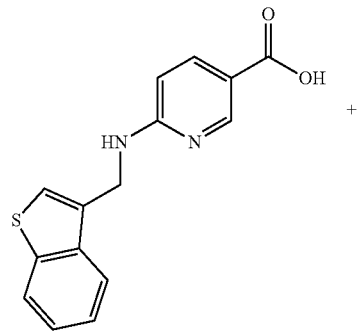

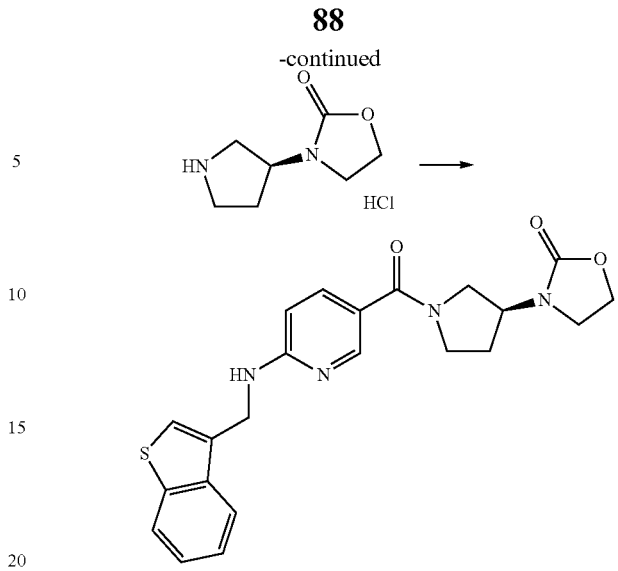

To a mixture of 28.4 mg (0.10 mmol) 6-{[(1-benzothiophen-3-yl)methyl]amino}pyridine-3-carboxylic acid, 19.3 mg (0.10 mmol) 3-[(3S)-pyrrolidin-3-yl]-1,3-oxazolidin-2-one hydrochloride, 41.8 mg (0.11 mmol) HATU and 1 mL DMF are added 56.8 L (0.33 mmol) DIPEA and the reaction mixture is stirred at RT overnight.

The mixture is filtered over Al$_2$O$_3$, washed with 0.5 mL DMF and is purified by HPLC (ACN/H$_2$O/NH$_4$OH) to obtain the product.

C$_{22}$H$_{22}$N$_4$O$_3$S (M=422.5 g/mol)
ESI-MS: 423 [M+H]$^+$
R$_t$ (HPLC): 0.66 min (method D)

The following compounds are prepared according to the general procedure (example 8.1) described above:

| Ex. | Starting materials | Structure | Reaction conditions | ESI-MS | HPLC Rt [min] (method) |
|---|---|---|---|---|---|
| 8.2 | XXXV.1  III.2 | 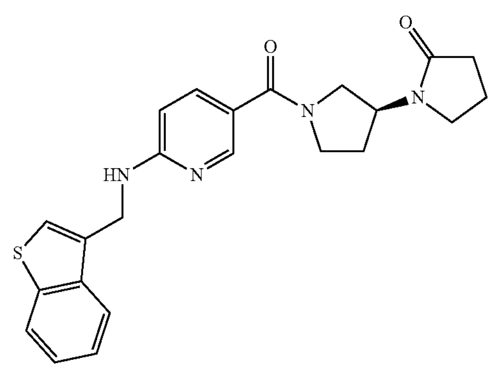 [SMILES: O=C(c1ccc(NCc2csc3ccccc23)nc1)N1CC[C@H](N2CCCC2=O)C1] | | 421 [M + H]$^+$ | 0.67 (D) |

Example 9

Example 9.1 (General Route)

N-[(3S)-1-(6-{[(1-Benzothiophen-3-yl)methyl]amino}pyridine-3-carbonyl)pyrrolidin-3-yl]-N-methylcyclobutanecarboxamide

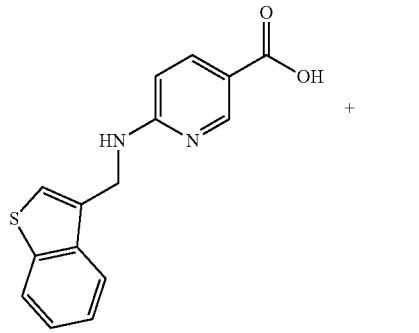

+

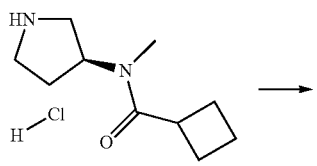

→

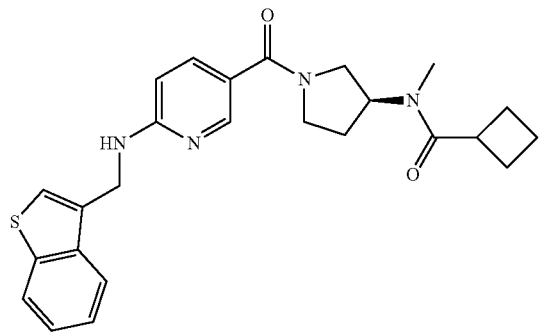

To a mixture of 28.4 mg (0.10 mmol) 6-{[(1-benzothiophen-3-yl)methyl]amino}pyridine-3-carboxylic acid, 21.9 mg (0.10 mmol) N-methyl-N-[(3S)-pyrrolidin-3-yl]cyclobutanecarboxamide hydrochloride, 56.8 μL (0.33 mmol) DIPEA and 1 mL DMF are added 41.8 mg (0.11 mmol) HATU and the reaction mixture is stirred at RT overnight.

The mixture is filtered over $Al_2O_3$, washed with 0.5 mL DMF and is purified by HPLC (ACN/$H_2O$/TFA) to obtain the product.

$C_{22}H_{22}N_4O_3S$ (M=448.6 g/mol)

ESI-MS: 449 [M+H]$^+$

R$_t$ (HPLC): 0.59 min (method F)

The following compounds are prepared according to the general procedure (example 9.1) described above:

| Ex. | Starting materials | | Structure | Reaction conditions | ESI-MS | HPLC Rt [min] (method) |
|---|---|---|---|---|---|---|
| 9.2 | XXXV.1 | XXXIX.1 | 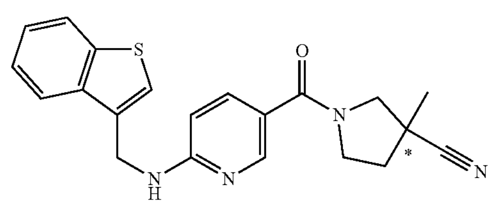 [SMILES: CC1(C#N)CCN(C(=O)c2ccc(NCc3csc4ccccc34)nc2)C1] | | 377 [M + H]$^+$ | 0.55 (F) |

*The stereochemistry at the chiral center of the enantiomerically and diastereomercially pure compound was not determined.

Analytical HPLC Methods

Method A

| time (min) | Vol % water (incl. 0.1% TFA) | Vol % ACN | Flow [mL/min] |
| --- | --- | --- | --- |
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5 µm; 3.0 × 30 mm; column temperature: 60° C.

Method B

| time (min) | Vol % water (incl. 0.1% TFA) | Vol % ACN | Flow [mL/min] |
| --- | --- | --- | --- |
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 µm; 3.0 × 30 mm; column temperature: 60° C.

Method C

| time (min) | Vol % water (incl. 0.1% NH$_4$OH) | Vol % ACN | Flow [mL/min] |
| --- | --- | --- | --- |
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: XBridge C18 (Waters) 2.5 µm; 3.0 × 30 mm; column temperature: 60° C.

Method D

| Gradient/Solvent Time [min] | % Sol [Water 0.1% NH3] | % Sol [Acetonitrile] | Flow [ml/min] | Temp [° C.] |
| --- | --- | --- | --- | --- |
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Preparative column: XBridge (Waters) C18_3.0 × 30 mm_2.5 µm

Method E

| Gradient/Solvent Time [min] | % Sol [Water 0.1% NH3] | % Sol [Acetonitrile] | Flow [ml/min] | Temp [° C.] |
| --- | --- | --- | --- | --- |
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

XBridge C18_3.0 × 30 mm_2.5 µm (Waters)

Method F

| Gradient/Solvent Time [min] | % Sol [Water 0.1% TFA (v/v)] | % Sol [Acetonitrile 0.08% TFA (v/v)] | Flow [ml/min] | Temp [° C.] |
| --- | --- | --- | --- | --- |
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Preparative column: Sunfire (Waters) C18_3.0 × 30 mm_2.5 µm

Method G

| Gradient/Solvent Time [min] | % Sol [Water 0.1% TFA (v/v)] | % Sol [Acetonitrile 0.08% TFA (v/v)] | Flow [ml/min] | Temp [° C.] |
| --- | --- | --- | --- | --- |
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Preparative column: Sunfire (Waters) C18_3.0 × 30 mm_2.5 µm

Method H

| Gradient/Solvent Time [min] | % Sol [Water 0.1% FA (v/v)] | % Sol [Acetonitrile] | Flow [ml/min] | Temp [° C.] |
| --- | --- | --- | --- | --- |
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Sunfire C18_3.0 × 30 mm_2.5 µm (Waters)

Method I

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 75.0 | 25.0 | 4.0 | 40.0 | 2175.0 |
| 10.0 | 75.0 | 25.0 | 4.0 | 40.0 | 2175.0 |

CHIRAL ART® Cellulose SC_4.6 × 250 mm_5 µm (Agilent)

Method J

| Gradient/Solvent Time [min] | % Sol [scCO2] | % Sol [IPA 20 mM NH3] | Flow [ml/min] | Temp [° C.] | Back pressure [PSI] |
| --- | --- | --- | --- | --- | --- |
| 0.0 | 95.0 | 5.0 | 4.0 | 40.0 | 2175.0 |
| 10.0 | 95.0 | 5.0 | 4.0 | 40.0 | 2175.0 |

CHIRAL ART® Cellulose SC_4.6 × 250 mm_5 µm (YMC)

Description of Biological Properties

Vanin-1 Enzymatic Assay:

The test compounds are dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions are prepared, a further intermediate dilutions of the substances is carried out with assay buffer resulting in 1% final DMSO concentration in the assay.

0.1 nM of FLAG-tagged Vanin-1 (AA 22-493, T26I, produced internally) and test compounds are incubated at room temperature for 20 minutes in assay buffer (1 mM DTT, 0.0025% Brij-35, 50 mM HEPES, pH7.5). D-Pantethine (Sigma, Cat #P2125-5G) in assay buffer is added (final concentration 3 µM) and incubated for additional 30 minutes at room temperature. Total assay volume typically is 40 µl but might be adjusted according to needs. Reaction is stopped by adding equal volume of stop solution as the reaction mixture to reach 100 nM HD-pantothenic acid (as an internal standard) and 1% TFA. Assay plates are centrifuged for 2 minutes and the formation of pantothenic acid is detected by RapidFire Mass Spectrometry (mobile phase A: 0.1% formic acid and 0.01% trifluoroacetic acid in water; mobile phase B: 47.5% acetonitrile, 47.5% methanol, 0.1% formic acid and 0.01% trifluoroacetic acid in water) using a C18, 12 µL cartridge (Agilent Cat #G9205A).

The values given in Table I result from measurements of one or more samples. In case of multiple measurements the geometric mean values are given.

Human Whole Blood assay: Pantetheinase (vanin) converts panteheine into pantothenic acid and cysteamine. Accordingly, in the described protocol vanin activity is quantified by formation of pantothenic acid after pantetheine supplementation via pantethine. The assay is applicable to identify vanin inhibitors. Compound stocks are dissolved in DMSO at 10 mM. Further dilutions are performed in RPMI 1640 medium (Gibco, #A-10491-01) and final concentrations in the assay are 0.032 nM-500 nM.

Human blood is drawn into a blood bag (1% heparin, 50 I.E./mL). Blood is aliquoted into cavities of 96-deep-well plates at 290 µL and mixed with 10 µL compound solution or vehicle (30 sec at 1400 rpm on a shaker). Equilibration follows at room temperature, 250 rpm and for 30 min. The assay is started by adding 10 µL of substrate solution (2 µM pantethine in 1 mM DTT, 0.0025% Brij-35, 50 mM HEPES, pH7.5) to each well, except for some blank wells which receive 10 mL substrate buffer (1 mM DTT, 0.0025% Brij-35, 50 mM HEPES, pH7.5) only. Samples are thoroughly shaken (30 sec, 1400 rpm) and reaction is allowed to take place at room temperature, 250 rpm and for 5 min. The reaction is stopped by addition of a vanin tool inhibitor in excess (BI-1 total conc. 10 µM). Centrifugation of the plate follows at 4° C., 665 G for 10 min. Then the blood plasma samples (100 µL) are transferred into another 96-deep-well plate and proteins are precipitated (5 min on ice) by adding 100 µL of ice cold precipitation solution (1 µM labelled pantothenic acid (di-β-alanine-13C6,15N2 calcium salt, Sigma, #705837) in acetonitrile).

Afterwards the plate is centrifuged (4° C., 3220 G, 10 min) and supernatants (50 µL) are collected into another 96-deep-well plate and mixed (10 sec, 1400 rpm) with 150 µL ice cold formic acid (0.1%, Carl Roth GmbH+Co.KG, #CP03.1). The formation of pantothenic acid is detected by RapidFire Mass Spectrometry. A TripleQuad 6500+(AB-Sciex, Germany) is equipped with an LC-1290 system, a RapidFire autosampler (Agilent, Germany) and a C18 cartridge Type C 12 µL (Agilent Cat #G9526-80000). Mobile phase A is consisting of 0.09% formic acid and 0.01% trifluoroacetic acid in water and mobile phase B of 0.09% formic acid and 0.01% trifluoroacetic acid in acetonitrile/methanol/water=47.5/47.5/5.

Synthesis of Tool Inhibitor BI-1:

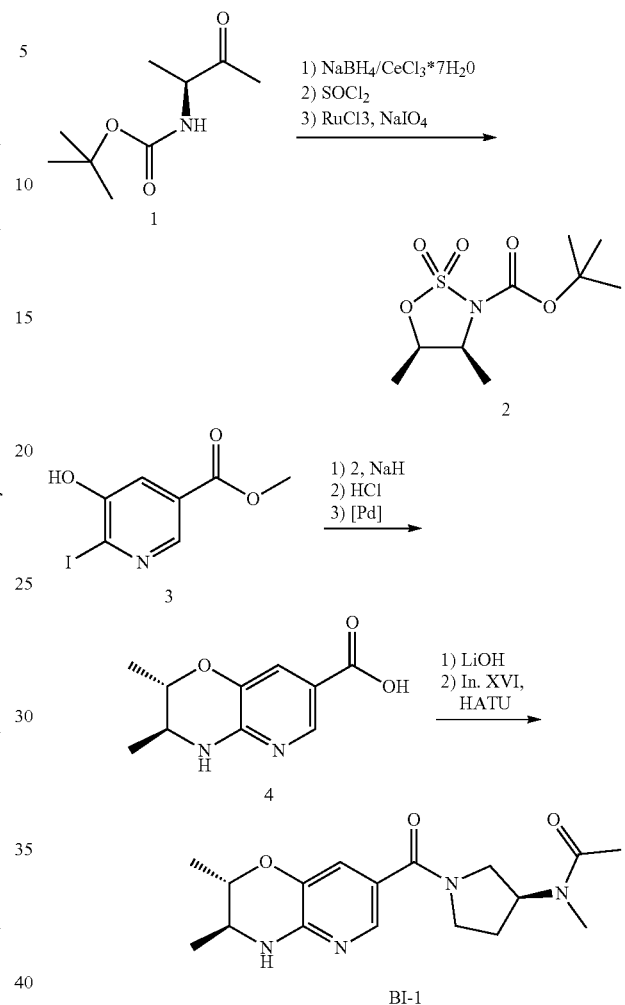

To 70 mL MeOH are added 5.40 g (28.8 mmol) ketone 1 (synthesis described in Angew. Chem. Int. Ed. 2010, 49, 6856) and 12.9 g (34.6 mmol) CeCl$_3$*7 H$_2$O. The reaction mixture is cooled to −15° C. before 2.18 g (57.7 mmol) NaBH$_4$ are added portion wise. The reaction mixture is stirred for 3 h at 0° C. The reaction is quenched by the addition of saturated aq. NH$_4$Cl solution and extracted with EtOAc. The organic layers are combined, dried over Na$_2$SO$_4$ and the solvent is removed in vacuo.

A stirred solution of 6.29 g (52.8 mmol) thionyl chloride in 50 mL acetonitrile is cooled to the −50° C. and a solution of 4 g (21.1 mmol) in ACN of the above mentioned product is added drop wise. When addition completed then 258 mg (2.11 mmol) DMAP are added in one portion. The mixture is stirred for 15 min, keeping temperature below −40° C., and then 8.36 g (106 mmol) dry pyridine are added, keeping external temperature at −40° C. Stirring is continued for 1 h. EtOAc is added, stirred for 5 mins, suspension appeared (pyridine salt) which is filtered and washed with EtOAc. To the filtrate is added 12 mL saturated Na$_2$HPO$_4$ slowly. The resulting solution is stirred for 40 mins. Two layers are separated. The organic layer is washed with 10 mL 1M NaHSO$_4$ aqueous, dried over Na$_2$SO$_4$ and concentrated under reduced pressure. The crude compound is purified by column chromatography (silica gel, 8% EtOAc in hexane).

C₉H₁₇NO₄S (M=235.3 g/mol)
ESI-MS: 258 [M+Na]⁺
R$_f$ (TLC, silica gel) 0.4 (PE/EtOAc 3/1)

To a solution of 1.00 g (0.004 mol) of the above described product in 10,000 ml EtOAc are added 1.36 g (0,006 mol) NaIO₄ in 10 mL H₂O Then 44 mg (0.2 mmol) RuCl₃ are added and the mixture is stirred at 0 to 15° C. for 12 h. The mixture is quenched with H₂O (20 mL) and extracted with EtOAc. Then the organic phase is washed with brine (20 mL), dried over Na₂SO₄, filtered and concentrated to dryness. The residue is purified by column chromatography (silica gel, PE/EtOAc=10:1 to 3:1).

C₉H₁₇NO₅S (M=251.3 g/mol)
ESI-MS: 252 [M+H]⁺
R$_f$ (TLC, silica gel) 0.55 (PE/EtOAc 3/1)

4.00 g (14.3 mmol) methyl 5-hydroxy-6-iodopyridine-3-carboxylate are added to 40 ml of DMF. To this are added 602 mg (15.1 mmol) sodium hydride. After gas evolution, 5.40 g (21.5 mmol) are added and the reaction mixture is stirred at 75 C for 1.5 h. After cooling down to RT, the reaction mixture is diluted with EtOAc and rinsed with water. The organics are dried, filtered, and evaporated.

The residue is purified by column chromatography (silica gel, 0-5% MeOH/CH₂Cl₂).

C₁₆H₂₃IN₂O₅ (M=450.3 g/mol)
ESI-MS: 451 [M+H]⁺

5.00 g (11.1 mmol) of the above mentioned product are added to in 50 ml of MeOH and 10 ml of CH₂Cl₂. To this are added 50 ml of 4 M HCl in dioxane. After 3 h the volatiles are removed in vacuo and the residue used without further purification.

3.28 g (9.37 mmol) of the above mentioned product, 105 mg (0.47 mmol) Pd(OAc)₂, 0.33 g (0.56 mmol), 9,9-dimethyl-4,5-bis(diphenylphosphino)xanthene (0.33 g; 0.56 mmol; 6.00 mol %) and 9.16 g (28.1 mmol) cesium carbonate are added to 100 ml dioxane and the mixture is degassed thoroughly. The reaction mixture is stirred at 90° C. under argon for 4 h. The solids are filtered through a plug of Celite® and evaporated. The residue is purified by column chromatography (silica gel, 0-5% MeOH/CH₂Cl₂).

1.50 g (6.75 mmol) of the above mentioned product are added to 5 ml of MeOH and 70 ml of water. To this are added 323 mg (13.5 mmol) LiOH and the reaction mixture is stirred at 50° C. for 1 h. The reaction is filtered and the MeOH is removed in vacuo. The aqueous layer is neutralized with 1 M HCl. The solids are filtered and allowed to dry and used without further purification.

C₁₀H₁₂N₂O₃ (M=208.2 g/mol)
ESI-MS: 209 [M+H]⁺
Rt (HPLC): 0.60 min (method A)

915 mg (4.39 mmol) of the above mentioned product are dissolved in 20 ml of DMF. To this are added 0.86 g (4.83 mmol) of intermediate XVI and 1.84 ml (13.2 mmol) TEA) followed by 1.84 g (4.83 mmol) HATU. The reaction mixture is stirred at RT for 16 h.

Volatiles are removed in vacuo and the residue is purified by column chromatography (Biotage KP-Nh cartridge, 0-10% MeOH/EtOAc).

C₁₇H₂₄N₄O₃ (M=332.4 g/mol)
ESI-MS: 333 [M+H]⁺
R$_t$ (HPLC): 0.63 min (method A)

Other features and advantages of the present invention will become apparent from the following more detailed Examples which illustrate, by way of example, the principles of the invention

TABLE I

Biological properties of representatives of the present invention

| Example | VNN-1 IC50 (nM) | HWB IC50 (nM) |
|---|---|---|
| 1.1 | 0.24 | 3.49 |
| 1.2 | 0.09 | 1.94 |
| 1.3 | 0.10 | 3.05 |
| 1.4 | 0.10 | 2.07 |
| 1.5 | 0.11 | 1.58 |
| 1.6 | 0.12 | 6.38 |
| 1.7 | 0.13 | 1.70 |
| 1.8 | 0.14 | |
| 1.9 | 0.15 | 1.89 |
| 1.10 | 0.16 | 2.78 |
| 1.11 | 0.20 | |
| 1.12 | 0.10 | 1.48 |
| 1.13 | 0.15 | 3.03 |
| 1.14 | 0.18 | 2.59 |
| 1.15 | 0.19 | 4.82 |
| 1.16 | 0.20 | 2.78 |
| 1.17 | 0.83 | 10.43 |
| 1.18 | 0.41 | 3.67 |
| 1.19 | 0.30 | 3.78 |
| 2.1 | 0.23 | 5.03 |
| 2.2 | 0.14 | |
| 2.3 | 0.21 | |
| 2.4 | 0.29 | 1.39 |
| 2.5 | 0.67 | |
| 2.6 | 2.05 | |
| 3.1 | 0.41 | 7.21 |
| 4.1 | 0.10 | 1.63 |
| 5.1 | 0.04 | 1.17 |
| 5.2 | 0.07 | 1.68 |
| 5.3 | 0.09 | 11.25 |
| 5.4 | 0.12 | 1.59 |
| 5.5 | 0.13 | |
| 5.6 | 0.13 | 2.10 |
| 5.7 | 0.14 | 4.49 |
| 5.8 | 0.16 | 1.71 |
| 5.9 | 0.18 | 10.33 |
| 5.10 | 0.18 | 1.41 |
| 5.11 | 0.21 | |
| 5.12 | 0.23 | 3.91 |
| 5.13 | 0.28 | 1.71 |
| 5.14 | 0.36 | 1.69 |
| 5.15 | 0.60 | 7.52 |
| 5.16 | 0.62 | 4.39 |
| 5.17 | 0.64 | |
| 5.18 | 0.69 | |
| 5.19 | 0.75 | 3.69 |
| 5.20 | 0.76 | |
| 5.21 | 0.79 | 3.40 |
| 5.22 | 0.82 | 3.35 |
| 5.23 | 1.43 | 4.10 |
| 5.24 | 1.23 | 3.88 |
| 5.25 | 1.43 | |
| 5.26 | 1.62 | |
| 5.27 | 2.25 | |
| 5.28 | 2.65 | |
| 5.29 | 2.74 | |
| 5.30 | 3.02 | |
| 5.31 | 4.62 | |
| 5.32 | 9.06 | |
| 5.33 | 9.33 | |
| 5.34 | 9.43 | |
| 5.35 | 0.12 | 1.39 |
| 5.36 | 0.22 | 4.86 |
| 5.37 | 0.24 | |
| 5.38 | 0.36 | 1.37 |
| 5.39 | 0.29 | 26.22 |
| 5.40 | 0.54 | 1.06 |
| 6.1 | 0.14 | |
| 7.1 | 0.33 | 7.66 |
| 8.1 | 0.20 | |
| 8.2 | 0.21 | |
| 9.1 | 0.26 | |
| 9.2 | 1.14 | |

Ex. 5.40
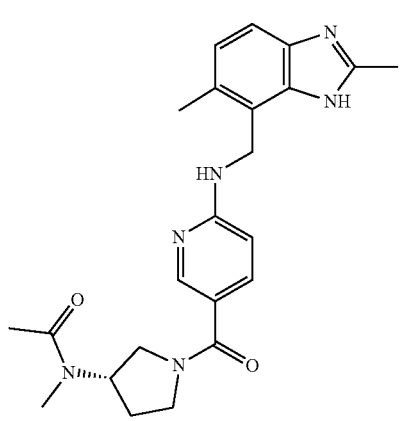

The invention claimed is:
1. A compound of the formula I,

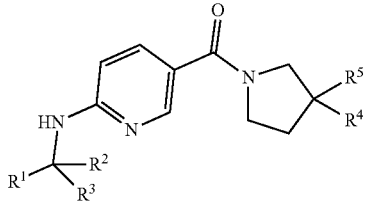

wherein
R$^1$ denotes naphthalenyl substituted with R$^{1.1}$ and R$^{1.2}$ or
  8-10 membered heteroaryl containing 1 to 3 heteroatoms selected from the group consisting of S, N and O substituted with R$^{1.1}$ and R$^{1.2}$,
R$^{1.1}$ is selected from the group consisting of H, C$_{1-4}$-alkyl, C$_{1-2}$-alkyl-O—, CF$_3$, C$_{3-5}$-cycloalkyl, H$_2$N—, Br, Cl and F;
R$^{1.2}$ is selected from the group consisting of H, C$_{1-4}$-alkyl, CF$_3$, H$_2$N—, Br, Cl and F;
wherein the alkyl of R$^{1.1}$ and R$^{1.2}$ are each independently optionally substituted by 1-3 F-atoms
R$^2$ and R$^3$ are independently from each other selected from the group consisting of H and methyl,
R$^4$ denotes R$^{4.1}$R$^{4.2}$N— or NC;
or
R$^4$ denotes a group of formula R$^{4.a}$

wherein the asterisk (*) denotes the point of attachment of the R$^{4a}$ group to the pyrrolidinyl ring of the compound of formula I, wherein
X denotes CH$_2$ or O;
R$^{4.1}$ is selected from the group consisting of C$_{1-4}$-alkyl-CO—, 6-membered heteroaryl containing 1-2 N-atoms, C$_{3-5}$-cycloalkyl-CO— substituted by R$^{4.1.1}$ and R$^{4.1.2}$, Phenyl-CO— optionally substituted by 1-2 halogen atoms, C$_{1-4}$-alkyl- or CH$_3$—O— and 5 to 6 membered heteroaryl-CO-optionally substituted by C$_{1-4}$-alkyl- or CH$_3$—O—,
wherein
  R$^{4.1.1}$, R$^{4.1.2}$ independently from each other are selected from the group consisting of H, —CH$_3$, F, and —CN;
R$^{4.2}$ denotes H or C$_{1-3}$-alkyl, and
R$^5$ denotes H or methyl;
or a pharmaceutically acceptable salt thereof.
2. The compound according to claim 1, wherein
R$^1$ denotes naphthalenyl,
  8-10 membered heteroaryl containing 1 to 3 heteroatoms selected from the group consisting of N and S substituted with R$^{1.1}$ and R$^{1.2}$,
  or
  8-10 membered heteroaryl containing 1 to 3 heteroatoms selected from the group consisting of N and O substituted with R$^{1.1}$ and R$^{1.2}$,
or a pharmaceutically acceptable salt thereof.
3. The compound according to claim 1, wherein
R$^{1.1}$ is selected from the group consisting of H, methyl, H$_2$N—, Br, Cl and F;
or a pharmaceutically acceptable salt thereof.
4. The compound according to claim 1, wherein
R$^{1.2}$ is selected from the group consisting of H, methyl and Cl;
or a pharmaceutically acceptable salt thereof.
5. The compound according to claim 1, wherein
R$^2$ denotes H,
and
R$^3$ denotes methyl;
or a pharmaceutically acceptable salt thereof.
6. The compound according to claim 1, wherein
R$^2$ and R$^3$ denote H;
or a pharmaceutically acceptable salt thereof.
7. The compound according to claim 1, wherein
R$^4$ denotes R$^{4.1}$R$^{4.2}$N—;
or a pharmaceutically acceptable salt thereof.
8. The compound according to claim 1, wherein
R$^{4.1}$ is selected from the group consisting of CH$_3$—CO—, C$_{3-4}$-cycloalkyl-CO-substituted with R$^{4.1.1}$ and R$^{4.1.2}$, wherein
  R$^{4.1.1}$ and R$^{4.1.2}$ independently from each other are selected from the group consisting of H, —CH$_3$, F and —CN;
R$^{4.2}$ denotes methyl;
or a pharmaceutically acceptable salt thereof.
9. The compound according to claim 1, wherein
R$^5$ denotes H;
or a pharmaceutically acceptable salt thereof.
10. The compound according to claim 1, wherein
R$^1$ denotes naphthalenyl or
  8-10 membered heteroaryl containing 1 to 3 heteroatoms selected from the group consisting of S, N and O substituted with R$^{1.1}$ and R$^{1.2}$,
R$^{1.1}$ is selected from the group consisting of H, methyl, H$_2$N—, Br, Cl and F;
R$^{1.2}$ is selected from the group consisting of H, methyl and Cl;
R$^2$ and R$^3$ independently from each other denote H or methyl;
R$^4$ denotes R$^{4.1}$R$^{4.2}$N— or NC—;
or R$^4$ denotes a group of formula R$^{4.a}$

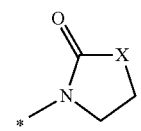

wherein
X denotes CH$_2$ or O;
R$^{4.1}$ is selected from the group consisting of C$_{1-4}$-alkyl-CO, C$_{3-4}$-cycloalkyl-CO— substituted with R$^{4.1.1}$ and R$^{4.1.2}$,
wherein
  R$^{4.1.1}$, R$^{4.1.2}$ independently from each other are selected from the group consisting of H, —CH$_3$, F and —CN;
R$^{4.2}$ denotes methyl; and
R$^5$ denotes H or methyl;
or a pharmaceutically acceptable salt thereof.

11. The compound of formula I according to claim 1 selected from the group consisting of examples 2.1, 3.1, 4.1, 5.2, 5.3, 5.4, 5.7, 5.13, 5.14, 5.22, 5.24, 5.38 and 5.40;
Ex. 2.1
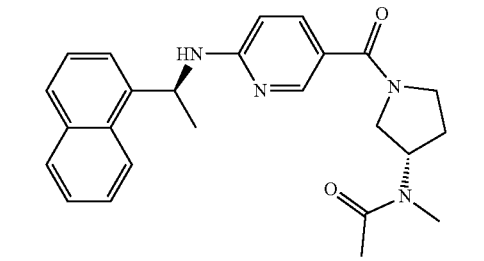
Ex. 3.1
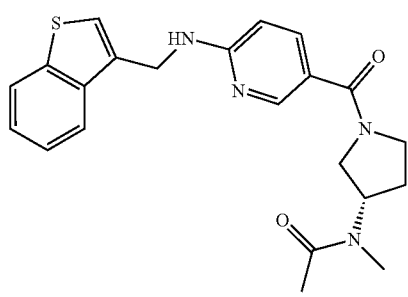
Ex. 4.1
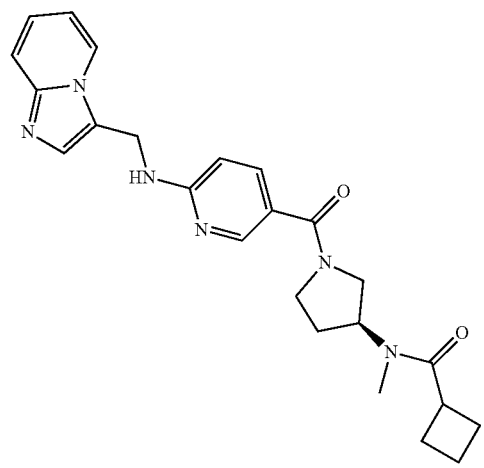
Ex. 5.2
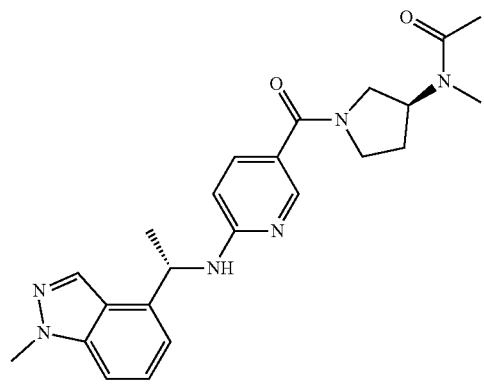
Ex. 5.4
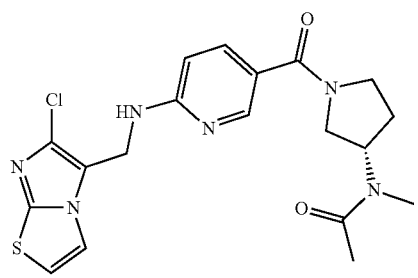
Ex. 5.7
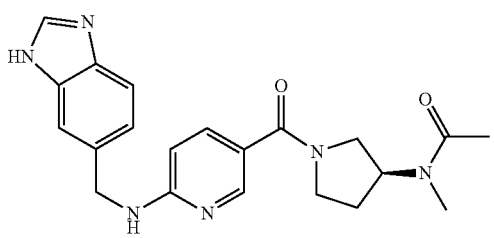
Ex. 5.13
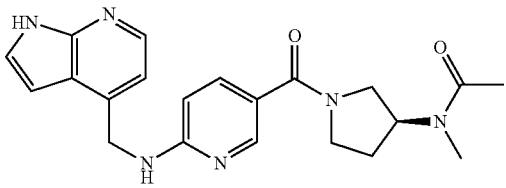
Ex. 5.14
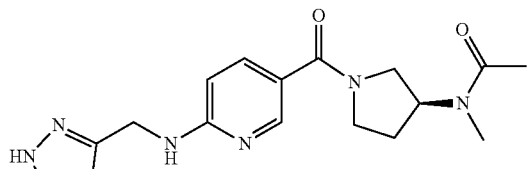
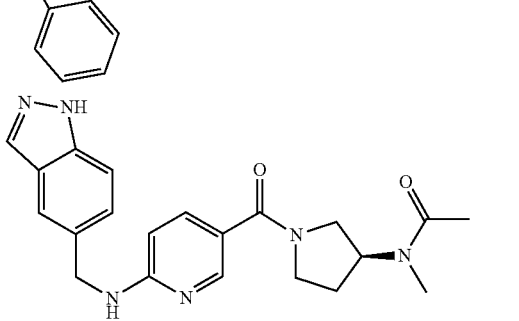
Ex. 5.24
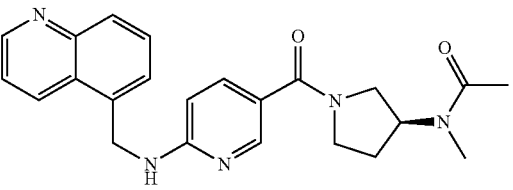

-continued

Ex. 5.38
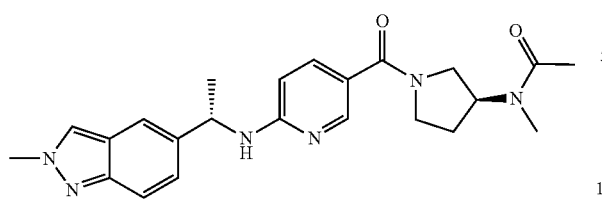

-continued

Ex. 5.3
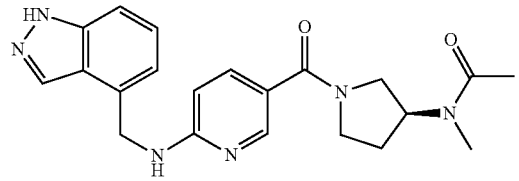

or a pharmaceutically acceptable salt thereof.

12. A pharmaceutical composition comprising a therapeutically effective amount of at least one compound of formula I according to claim 1 or a pharmaceutically acceptable salt thereof and one or more pharmaceutically acceptable excipients.

13. A method of treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, hyperlipidemia, colorectal cancer- or pancreatic cancer-related new-onset diabetes, said method comprising administering to the patient a therapeutically effective amount the compound according to claim 1.

14. A pharmaceutical composition comprising the compound of formula I according to claim 1, and additionally a pharmaceutically active compound selected from the group consisting of an immunomodulatory agent, anti-inflammatory agent or a chemotherapeutic agent.

\* \* \* \* \*